US012728170B2

(12) United States Patent
Juen et al.

(10) Patent No.: US 12,728,170 B2
(45) Date of Patent: Sep. 8, 2026

(54) COMPOUNDS CAPABLE OF BINDING TO PROTEINS AND CONJUGATES OBTAINED FROM THESE COMPOUNDS

(71) Applicant: MC SAF, Tours (FR)

(72) Inventors: Ludovic Juen, Tours (FR); Camille Gely, Severac-d'Aveyron (FR); Estelle Huet, Mayet (FR)

(73) Assignee: MC SAF, Tours (FR)

( * ) Notice: Subject to any disclaimer, the term of this patent is extended or adjusted under 35 U.S.C. 154(b) by 709 days.

(21) Appl. No.: 18/006,070

(22) PCT Filed: Jul. 19, 2021

(86) PCT No.: PCT/FR2021/051345

§ 371 (c)(1),
(2) Date: Jan. 19, 2023

(87) PCT Pub. No.: WO2022/018371

PCT Pub. Date: Jan. 27, 2022

(65) Prior Publication Data

US 2023/0277678 A1 Sep. 7, 2023

(30) Foreign Application Priority Data

Jul. 20, 2020 (FR) ....................................... 2007589

(51) Int. Cl.
*A61K 47/68* (2017.01)
*C07D 401/12* (2006.01)

(52) U.S. Cl.
CPC ...... *A61K 47/6889* (2017.08); *A61K 47/6803* (2017.08); *A61K 47/68031* (2023.08); *A61K 47/6851* (2017.08); *A61K 47/6863* (2017.08); *C07D 401/12* (2013.01)

(58) Field of Classification Search
CPC ............ A61K 47/6889; A61K 47/6851; A61K 47/6803; A61K 47/6863; A61K 47/68031; C07D 401/12
See application file for complete search history.

(56) References Cited

FOREIGN PATENT DOCUMENTS

| | | | |
|---|---|---|---|
| CA | 3106493 | A1 | 6/2020 |
| WO | 2015004400 | A1 | 1/2015 |
| WO | 2016064749 | A2 | 4/2016 |
| WO | 2016123412 | A1 | 8/2016 |
| WO | 2016123412 | A9 | 8/2016 |
| WO | 2020234541 | A1 | 11/2020 |

OTHER PUBLICATIONS

Ishi (J. Org. Chem. 1999, 64, 984-990) (Year: 1999).*
Villard, Anne-Laure (Authorized Officer), International Search Report and Written Opinion of the International Searching Authority for International Application No. PCT/FR2021/051345 with English language translation dated Nov. 5, 2021, 13 pages.
Hao et al., "Effect of Macromonomer Branching on Structural Features and Solution Properties of Long-Subchain Hyperbranched Polymers: The Case of Four-Arm Star Macromonomers," Macromolecules, 2019, vol. 52, No. 17, pp. 6566-6577.
Lüning et al., "Concave Benzoic Acids," Chemische Berichte, 1991, vol. 124, pp. 397-402.

* cited by examiner

*Primary Examiner* — Kortney L. Klinkel
*Assistant Examiner* — Richard Grant Peckham
(74) *Attorney, Agent, or Firm* — MH2 Technology Law Group, LLP

(57) ABSTRACT

The disclosure relates to a compound of formula (I):

(I)

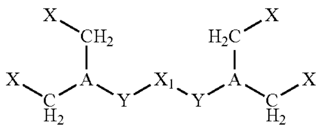

wherein X, A, Y and $X_1$ are as defined in the description. The disclosure also relates to a conjugate between a protein comprising at least two disulfide bridges and a compound of formula (I).

13 Claims, No Drawings

COMPOUNDS CAPABLE OF BINDING TO PROTEINS AND CONJUGATES OBTAINED FROM THESE COMPOUNDS

CROSS REFERENCE TO RELATED APPLICATIONS

This application is a U.S. National Stage Application of PCT/FR2021/051345 filed 19 Jul. 2021, which claims priority to French Patent Application No. 2007589 filed 20 Jul. 2020, the entire disclosures of which are hereby incorporated by reference in their entireties.

TECHNICAL FIELD

The present disclosure relates to compounds capable of binding to proteins, and the use of these compounds to prepare conjugates with proteins, said conjugates being able to further comprise an active ingredient.

STATE OF THE ART

The beginning of the 2000s saw an intensification of research on conjugates between a protein, in particular an antibody, and a molecule of interest, in particular an active drug ingredient, these conjugates potentially representing an alternative or a complement to "conventional" therapies to selectively deliver an active ingredient. In particular, an antibody drug conjugate (or "ADC") constitutes a means for selectively delivering a drug, in particular a cytotoxic drug. The antibody drug conjugate therefore allows to combine the specificity of the targeting by the antibodies with new powerful effector functions by the agents which are conjugated to them.

The structure of an antibody drug conjugate typically consists of an antibody bound to the drug by a molecule one part of which will bind the antibody and another part will be coupled to the drug, usually via a spacer arm (or linker) of variable length and nature.

After binding to its target antigen, the antibody is most often internalized in the cell by receptor-mediated endocytosis. The vesicles fuse with lysosomes where the drug is released from the antibody via different mechanisms. The active drug then acts directly on the cell by inducing its death and sometimes on neighboring cancer cells by transport or diffusion in the environment. The antibody is therefore mainly used as a vector and brings the drug to the targeted cell.

In the context of obtaining ADC by bioconjugation on disulfide bridges, the stability of antibody drug conjugates depends in particular on the capacity of the molecule which fixes the antibody to reconstruct the reduced disulfide bridges between the heavy chains and the light chains of the antibody.

It is however desirable to be able to limit the toxicity of the conjugates between a protein and a molecule of interest such as an active ingredient of a medicine, in particular in the context of a therapeutic use of these conjugates. In this context, the inventors set out to develop compounds (also called hereafter "attachment heads") which, when they are conjugated to proteins, in particular antibodies, allow to obtain a "structure" such that, on average, the number of conjugated attachment heads per protein (antibody) is controlled: the targeted majority conjugate bearing either 1 molecule per antibody or 2 molecules per antibody.

There is also a need to optimize the reconstruction of the antibodies, in particular with a view to preparing antibody drug conjugates having improved homogeneity and stability due to the reduced presence of unequally reconstructed species.

It is with this "specification" in mind that the inventors have developed the present disclosure.

BRIEF SUMMARY

The present disclosure relates to a compound of formula (I):

(I)

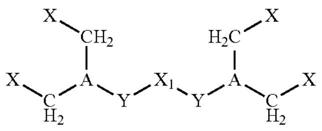

wherein X, A, Y and $X_1$ have the meaning given below in the detailed description.

The present disclosure also relates to a compound of formula (II):

(II)

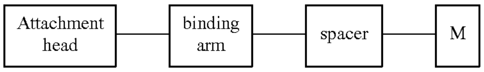

wherein the attachment head, the binding arm, the spacer and M have the meaning given below in the detailed description.

The present disclosure also relates to a conjugate obtainable by conjugation between a protein comprising at least two disulfide bridges and a compound of formula (I) or a compound of formula (II).

The present disclosure also relates to a composition comprising at least one aforementioned conjugate.

DETAILED DESCRIPTION

According to a first aspect, the disclosure relates to a compound of formula (I):

(I)

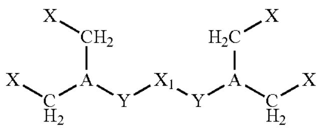

wherein:

each A is the residue of a phenyl or a pyridyl;

each X is a leaving group;

each Y is a direct bond, $-CH_2-$, $-O-$, $-S-$, $-CO-$, $-NH-$ or $-C(=NR_1)-$;

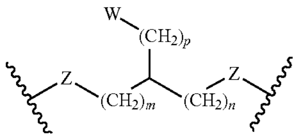 and 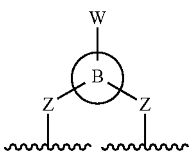 ;

each Z is independently a direct bond, —CH—, —O—, —S—, —CO—, —NH— or $C(=NR_1)$—;

W is —$OR_a$, —$COR_2$, —$CONR_3R_4$ or —$NR_3COR_4$;

$R_a$ is —($C_1$-$C_6$)alkyl, —$(CH_2CH_2O)_qR_5$, —$(CR_cR_d)_rR_5$, —$COR_b$, —$(CR_cR_d)_r$—NHCO—$(CH_2CH_2O)_qR_5$, —$(CR_cR_d)_r$—CONH—$(CH_2CH_2O)_qR_5$, —$(CH_2CH_2O)_q$—$(CH_2)_r$—NHCO—$(CR_cR_d)_r$—$R_5$ or —$(CH_2CH_2O)_q$ $(CH_2)_r$—CONH—$(CR_cR_d)_r$—$R_5$;

$R_b$ is —($C_1$-$C_6$)alkyl, —($C_1$-$C_6$)alkoxy, —$(CH_2CH_2O)_q$ $R_5$, —O$(CH_2CH_2O)_qR_5$, —$(CR_cR_d)_rR_5$, —O$(CR_cR_d)_r$ $R_5$, —$(CR_cR_d)_r$—NHCO—$(CH_2CH_2O)_q$—$R_5$, —$(CR_c$ $R_d)_r$—CONH—$(CH_2CH_2O)_qR_5$, —$(CH_2CH_2O)_q$—$(CH_2)_r$—NHCO—$(CR_cR_d)_r$—$R_5$ or —$(CH_2CH_2O)_q$—$(CH_2)_r$—CONH—$(CR_cR_d)_r$—$R_5$;

$R_1$ is —H, —OH or —($C_1$-$C_6$)alkyl;

$R_2$ is —OH, —($C_1$-$C_6$)alkyl, —($C_1$-$C_6$)alkoxy, —$(CH_2CH_2O)_qR_5$, —$(CR_cR_d)_rR_5$, —O$(CH_2CH_2O)_q$ $R_5$, —O$(CR_cR_d)_rR_5$, —O$(CR_cR_d)_r$—NHCO—$(CH_2CH_2O)_q$—$R_5$, —O$(CR_cR_d)_r$—CONH—$(CH_2CH_2O)_q$—$R_5$, —O$(CH_2CH_2O)_q$—$(CH_2)_r$—NHCO—$(CR_cR_d)_rR_5$ or —O$(CH_2CH_2O)_q(CH_2)_r$—CONH—$(CR_cR_d)_rR_5$;

$R_3$ is —H, —($C_1$-$C_6$)alkyl or —$(CH_2)_u$—$SO_3H$, preferably $R_3$ is —H or —($C_1$-$C_6$)alkyl;

$R_4$ is —H, —($C_1$-$C_6$)alkyl, —$(CH_2CH_2O)_qR_5$, —$(CR_c$ $R_d)_rR_5$, —$(CR_cR_d)_r$—NHCO—$(CH_2CH_2O)_q$—$R_5$, —$(CR_cR_d)_r$—CONH—$(CH_2CH_2O)_q$—$R_5$, —$(CH_2CH_2O)_q$—$(CH_2)_r$—NHCO—$(CR_cR_d)_rR_5$, —$(CH_2CH_2O)_q$—$(CH_2)_r$—CONH—$(CR_cR_d)_rR_5$, —CH—[$(CR_cR_d)_r$—CONH—$(CR_cR_d)_r(OCH_2CH_2)_q$ —$R_5]_2$, —CH—[$(CR_cR_d)_r$ NHCO—$(CR_cR_d)_r$—$(OCH_2CH_2)_qR_5$]2, —CH—[$(CR_cR_d)_r$—CONH—$(CR_c$ $R_d)_rR_5$]2, or —CH—[$(CR_cR_d)_r$ NHCO—$(CR_cR_d)_r$ $R_5]_2$, preferably $R_4$ is —H, —($C_1$-$C_6$)alkyl, —$(CH_2CH_2O)_qR_5$, —$(CR_cR_d)_rR_5$, —$(CR_cR_d)_r$—NHCO—$(CH_2CH_2O)_q$—$R_5$, —$(CR_cR_d)_r$—CONH—$(CH_2CH_2O)_qR_5$, —$(CH_2CH_2O)_q$—$(CH_2)_r$ NHCO—$(CR_cR_d)_rR_5$, or —$(CH_2CH_2O)_q$—$(CH_2)_r$—CONH—$(CR_cR_d)_r$—$R_5$;

$R_5$ is —$(CH_2)_5R_6$ or —$(CH_2)_5R_7$;

$R_6$ is —$COOR_8$, —$COSR_8$, —$CONR_8R_9$ or —$NR_8COR_9$;

$R_7$ is selected from:

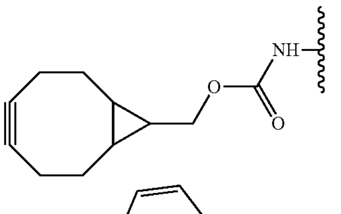

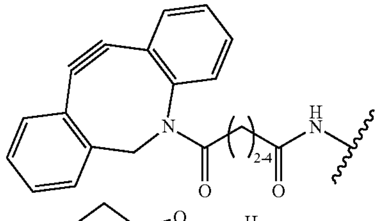

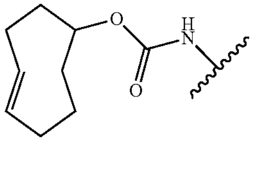

-continued

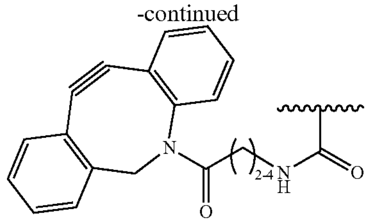

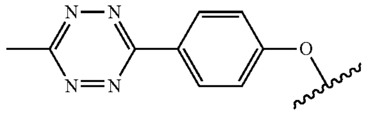

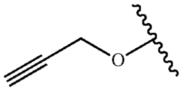

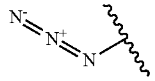

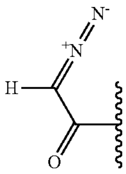

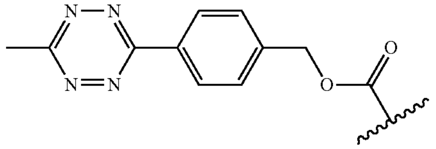

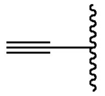

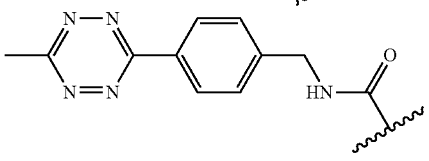
;

$R_c$ is —H;

each $R_d$ is —H or —$SO_3H$ or —$CH_2$—$SO_3H$, preferably each $R_d$ is —H or —$SO_3H$;

$R_8$ is —H or —($C_1$-$C_6$)alkyl;

$R_9$ is —H or —($C_1$-$C_6$)alkyl;

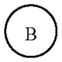

is a ($C_3$-$C_6$) cycloalkyl, a ($C_6$-$C_{10}$)aryl or a saturated, unsaturated or partially unsaturated heterocycle, having from 5 to 15 members and comprising from 1 to 4 heteroatoms selected from nitrogen, oxygen and sulfur;

m, n and p are each independently of one another an integer ranging from 0 to 8;

each q is an integer ranging from 1 to 24;

each r is an integer ranging from 1 to 8;

each s is an integer ranging from 0 to 6;

each u is an integer ranging from 1 to 6;

with the exception of the following compounds:

2,6-bis[2,6-bis(bromomethyl)phenyl]benzoic acid, and 1,3-bis[[3,5-bis(bromomethyl)phenoxy]methyl]-5-prop-2-ynoxy-benzene.

Definitions

"Aryl" means a phenyl or naphthyl group.

"Saturated, unsaturated or partially unsaturated heterocycle, having from 5 to 15 members, and comprising from 1 to 4 heteroatoms selected from nitrogen, oxygen and sulfur" means a monocyclic, bicyclic or tricyclic group, optionally fused, saturated, unsaturated or partially unsaturated, comprising from 1 to 4 heteroatoms, preferably from 1 to 3 heteroatoms, and more preferably 1 or 2 heteroatoms, selected from nitrogen, oxygen and sulfur.

As examples of unsaturated monocycles mention may be made of pyrrolyl, pyrazolyl, imidazolyl, oxazolyl, isoxazolyl, triazolyl, oxadiazolyl, furanyl, thienyl, thiazolyl, isothiazolyl, thiadiazolyl, pyridyl, pyridazinyl, pyrimidinyl, pyrazinyl, triazinyl, azepinyl, oxepinyl or thiepinyl.

As an example of a saturated monocycle, mention may be made of the pyrrolidinyl, tetrahydrofuryl, tetrahydrothienyl, pyrrolidinyl, imidazolidinyl, thiazolidinyl, isoxazolidinyl, piperidinyl, piperazinyl, morpholinyl, thiomorpholinyl or hexahydroazepinyl groups.

As an example of a partially unsaturated monocycle, mention may be made of the dihydro (is)oxazole group.

As an example of an unsaturated or partially unsaturated, optionally fused bicycle or tricycle, mention may be made of isoquinolyl, quinolyl, 1,4-dihydroquinolinyl, 2,4-dihydroquinolinyl, 1,2,3,4-tetrahydroquinolinyl, 1/pyrrolo[3,2-b] pyridinyl, benzimidazolyl, benzopyrazinyl, indolyl, 2,3-dihydroindolyl, indolynyl, benzofuranyl, 2,3-dihydrobenzofuranyl, benzothiazolyl, benzothiadiazolyl, benzisoxazolyl, 3,4-dihydro-1,4-benzoxazinyl, 2,4-dihydro-1,4-benzoxazinyl, 1,3-benzodioxolyl, 2,3-dihydrobenzodioxinyl, imidazothiazolyl, benzoxazolyl, benzoxazinyl, 4,5-dihydro-1,5-benzoxazepinyl, 2,3-dihydropyrido[4,3-b][1,4] oxazinyl, 3,4-dihydropyrido[3,2-b][1,4]oxazinyl, spiro [benzoxazine-2,1'-cyclobutane]-yl, chromanyl, chromenyl, spiro[chroman-2,1'-cyclobutane], spiro[chromene-2,1'-cyclobutane], spiro[cyclopentane-1,3'-indoline]-yl, spiro[indoline-3,3'-tetrahydrofuran]-yl, spiro[indoline-3,3'-tetrahydropyran]-yl, dihydro cyclopropa[b]indol-2-yl, hexahydrocarbazolyl, tetrahydrocarbazolyl, dihydrocarbazolyl or tetrahydrocyclopenta[b]indol-4-yl.

The different embodiments which appear in the present description can be combined with one another.

In one embodiment each leaving group X is a halogen, tosylate or mesylate, preferably each X is a halogen. Advantageously, each X is Br.

In one embodiment, each A is the residue of a pyridyl.

In one embodiment, each Y is selected from a direct bond, —CO— and —NH—. In this embodiment, one of the groups Y and Z is advantageously —CO— and the other is advantageously —NH—.

In one embodiment, $X_1$ is

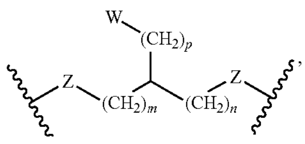

W is $—COR_2$ or $—CONR_3R_4$;

Z is —CO— or —NH—;

$R_2$ is —OH or $—(C_1\text{-}C_6)$alkoxy;

$R_4$ is —H, $—(C_1\text{-}C_6)$alkyl, $—(CH_2CH_2O)_q—R_5$, or $—(CR_cR_d)_rR_5$;

$R_5$ is $—(CH_2),R_6$ or $—(CH_2)_5R_7$;

$R_6$ is $—COOR_6$, $—CONR_8R_9$ or $—NR_8COR_9$;

$R_7$ is selected from:

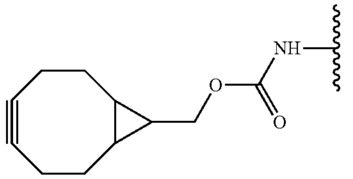

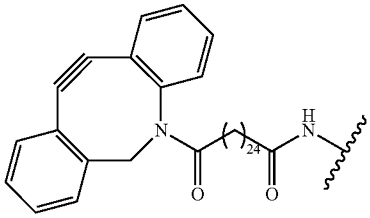

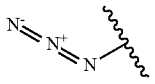

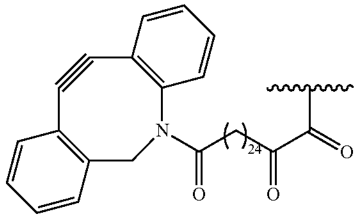

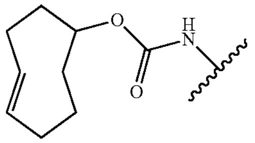

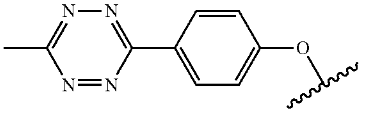

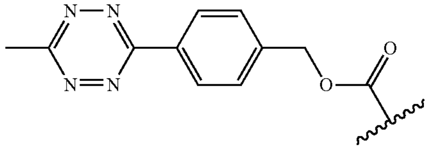

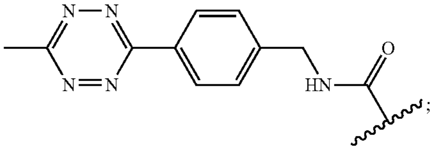;

$R_c$, $R_d$, $R_3$, $R_8$ and $R_9$ are as defined above;

m and n are each independently of one another an integer ranging from 0 to 3;

p is equal to 0, 1 or 2;

each q is an integer ranging from 1 to 12;

each r is an integer ranging from 1 to 6;

each s is an integer ranging from 0 to 4.

In one embodiment, $X_1$ is a group:

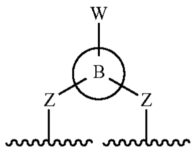

selected from:
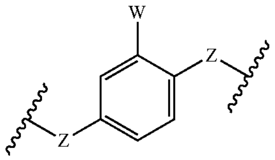
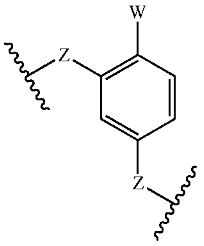
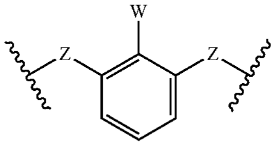
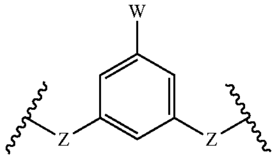
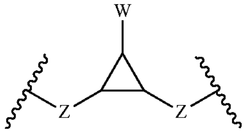
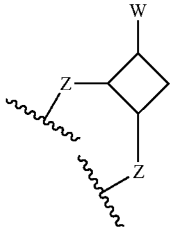
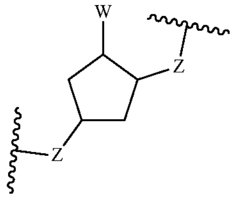
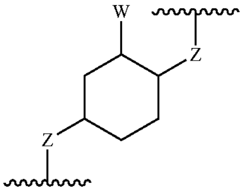
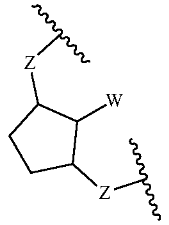
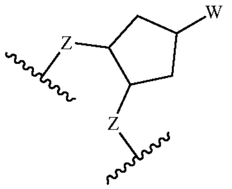
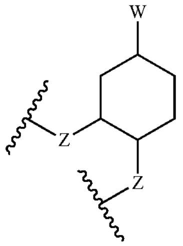
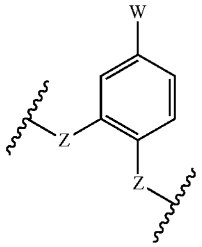
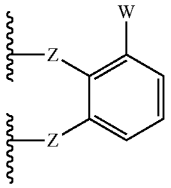
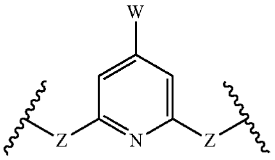
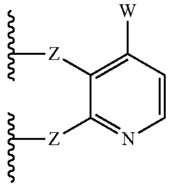
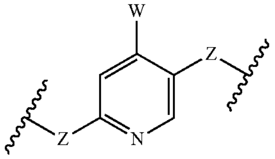
-continued
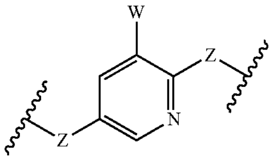
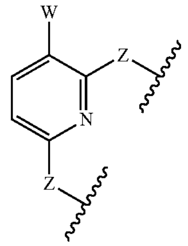
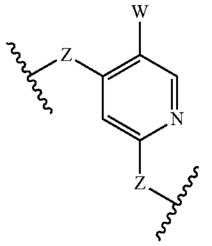
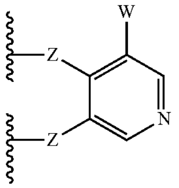
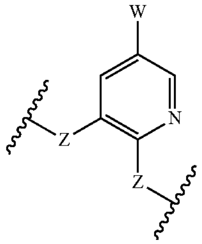
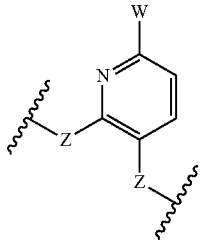
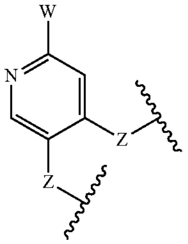
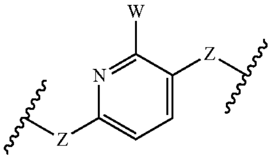
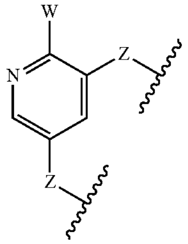
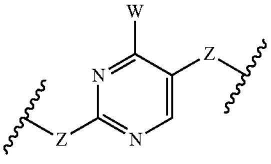
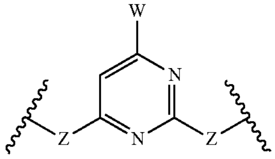
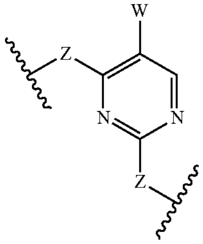
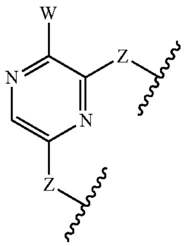
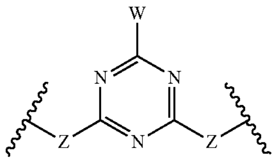

-continued

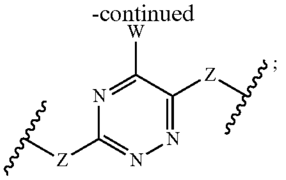

W is $-COR_2$ or $-CONR_3R_4$;

Z is —CO— or —NH—;

$R_2$ is —OH or $-(C_1\text{-}C_6)$alkoxy;

$R_3$ is —H or $-(C_1\text{-}C_6)$alkyl;

$R_4$ is —H, $-(C_1\text{-}C_6)$alkyl, $-(CR_cR_d)_rR_5$, or $-(CH_2CH_2O)_qR_5$;

$R_5$ is $-(CH_2)_5R_6$ or $-(CH_2),R_7$;

$R_6$ is $-COOR_8$, $-CONR_8R_9$ or $-NR_8COR_9$;

$R_7$ is selected from:

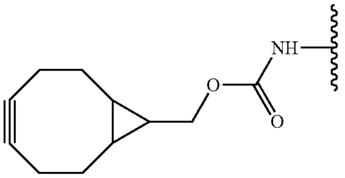

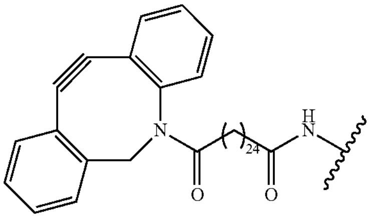

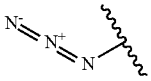

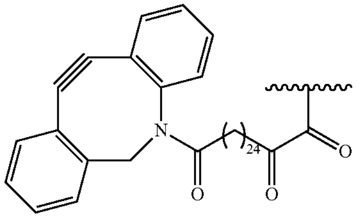

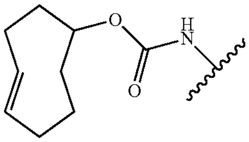

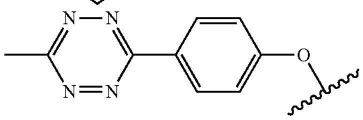

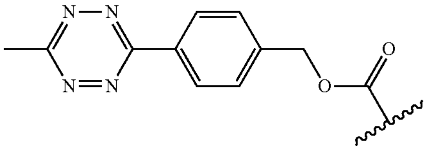

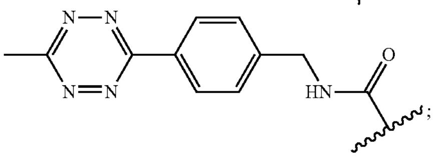

$R_c$, $R_d$, $R_8$ and $R_9$ are as defined above;

each q is an integer ranging from 1 to 12;

each r is an integer ranging from 1 to 6;

each s is an integer ranging from 0 to 4.

In this embodiment, $X_1$ is advantageously selected from:

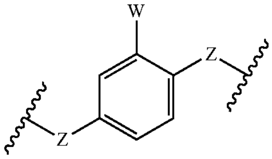

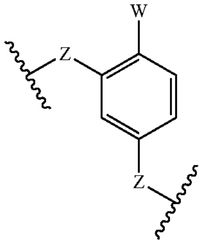

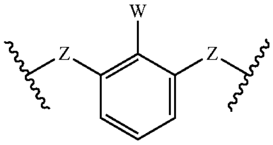

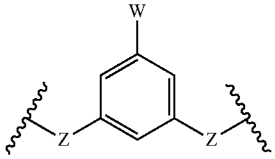

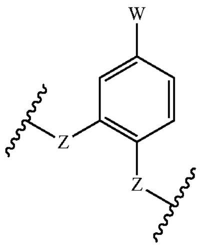

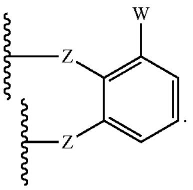

Preferably $X_1$ is:

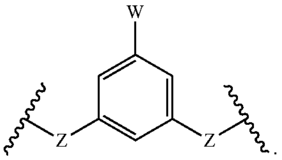

In one embodiment, the compound of formula (I) is a compound of formula (Ia), (Ib) or (Ic):

(Ia)

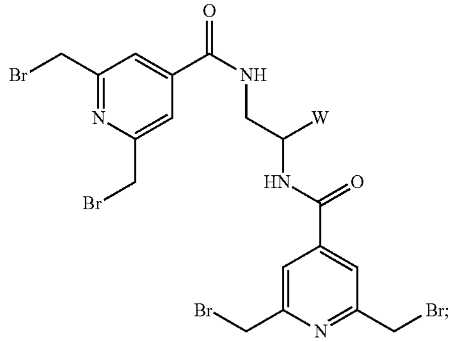

-continued (Ib)

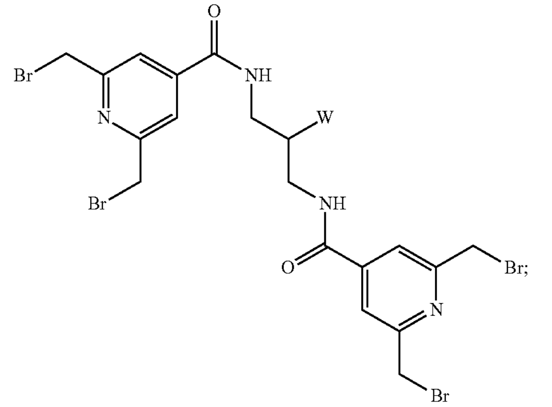

(Ic)

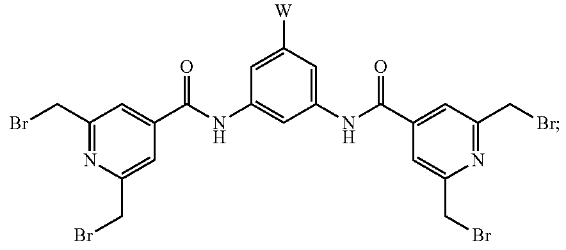

in each of these formulas W is as defined above. Advantageously, W is —$COR_2$ or —$CONR_3R_4$; $R_2$ is —OH or —($C_1$-$C_6$)alkoxy; $R_3$ is —H or —($C_1$-$C_6$)alkyl; $R_4$ is —$(CH_2CH_2O)_qR_5$, or —$(CR_cR_d)_rR_5$; $R_5$ is —$(CH_2)_sR_6$ or —$(CH_2)_rR_7$; $R_6$ is —$COOR_8$; $R_7$ is selected from:

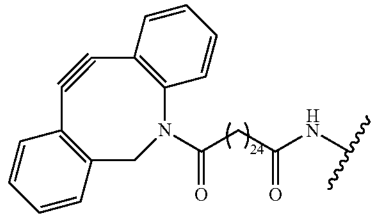

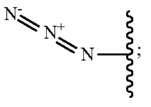

$R_8$ is —H or —($C_1$-$C_6$)alkyl; $R_c$ is —H and each $R_d$ is —H or —$SO_3H$; each q is an integer ranging from 1 to 12; each r is an integer ranging from 1 to 6; each s is an integer ranging from 0 to 4.

The compounds of formula (I) are particularly adapted for the homogeneous conjugation and the reconstruction of proteins comprising at least two disulfide bridges, in particular for the reconstruction of antibodies.

The terms "antibody" and "immunoglobulin" designate a heterotetramer consisting of two heavy chains of approximately 50-70 kDa each (called the H chains for Heavy) and two light chains of approximately 25 kDa each (called the L chains for Light), bound together by interchain disulfide bridges. Each chain is made up, in the N-terminal position, of a region or variable domain, called VL for the light chain, VH for the heavy chain, and in the C-terminal position, of a constant region, made up of a single domain called CL for the light chain and three or four domains called CH1, CH2, CH3, CH4, for the heavy chain.

"Antibody fragment" means any part of an immunoglobulin obtained by enzymatic digestion, bioproduction or protein engineering comprising at least two disulfide bridges, for example, $F(ab')_2$.

Enzymatic digestion of immunoglobulins with pepsin generates an $F(ab')_2$ fragment and an Fc fragment split into several peptides. $F(ab')_2$ is formed of two Fab' fragments bound by interchain disulfide bridges. The Fab parts consist of the variable regions and the CH1 and CL domains. The Fab' fragment consists of the Fab region and a hinge region.

The ability of the compounds of formula (I) to reconstruct proteins comprising at least two disulfide bridges allows to consider their use for preparing conjugates between such proteins and a molecule of interest, where appropriate via a spacer arm.

Thus, according to another aspect, the present disclosure relates to a compound of formula (II):

(II)

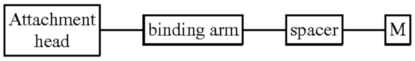

wherein:

the attachment head is a compound of formula (I) as defined above (it being understood that within the framework of the definition of the compound of formula (II) the acid compounds 2,6-bis[2,6-bis(bromomethyl)phenyl]benzoic acid and 1,3-bis[[3,5-bis(bromomethyl)phenoxy]-methyl]-5-prop-2-ynoxy-benzene are an integral part of formula (I));

the binding arm is a direct bond; an amino acid residue; a peptide residue; a sugar; a glucuronide; an —S—S-bridge; —$NHCH[CH_2COR_{10}]_2$—; or a group of formula:

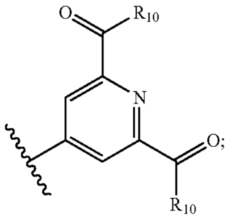

wherein $R_{10}$ is a direct bond, a peptide residue (preferably a dipeptide residue), —$(CR_cR_d)_rR_5$, or —$(CH_2CH_2O)_qR_5$, $R_c$, $R_d$, $R_5$, q and r being as defined above for the compound of formula (I); preferably $R_{10}$ is a direct bond or a peptide residue, preferably a dipeptide residue;

the spacer is a direct bond or a group of formula:

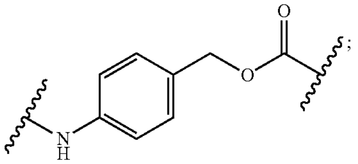 [SMILES: *Nc1ccc(COC(*)=O)cc1]

M is a molecule of interest.

The bond between each of the different parts of the compound of formula (II), namely attachment head, binding arm, spacer and molecule of interest, is performed via a bond of the amide, ester, ether, carbamate or carbonate type. The person skilled in the art will realize that the definition given for the attachment head in formula (II) is not strictly speaking correct and that in reality it should be read "residue of compound of formula (I)", one of the reactive groups carried by the compound of formula (I) having reacted to form the aforementioned bond of the amide, ester, ether, carbamate or carbonate type. For example, an acid or ester group carried by the compound of formula (I) has reacted with an amino group to form an amide-type bond between the attachment head and the binding arm (if present) or the spacer (if present) or the molecule of interest. In the same way, it is understood that the expression "molecule of interest" given in the definition of formula (II) must in fact be understood as meaning "residue of molecule of interest".

In one embodiment, the part of formula (II) consisting of the binding arm and the spacer is represented by one of the formulas (III) or (IV):

(III)

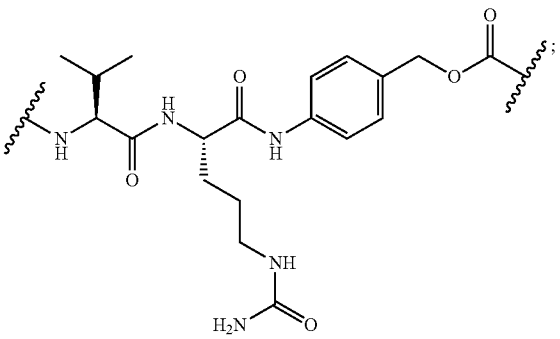

;

(IV)

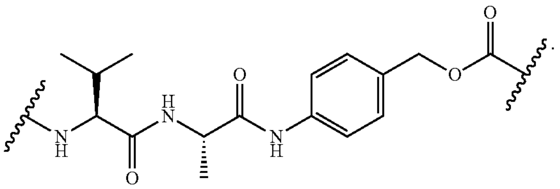

.

In one embodiment, the molecule of interest is an active ingredient, a fluorophore or a cage for radioelements. By way of active ingredient capable of being used in the context of the disclosure, mention may be made of the active ingredients of medicinal products already authorized and the molecules undergoing therapeutic evaluation, in particular:

- alkylating agents such as: chlorambucil, chlornaphazine, cyclophosphamide, dacarbazine, estramustine, ifosfamide, mechlorethamine, mechlorethamine oxide hydrochloride, mannomustine, mitobronitol, melphalan, mitolactol, pipobroman, novembichine, phenesterine, prednimustine, thiotepa, trofosfamide, uracil mustard, CC-1065 (including its synthetic analogs adozelesin, carzelesin, and bizelesin), duocarmycin (including the synthetic analogs KW-2189 and CBI-TMI), benzodiazepine dimers (for example, pyrrolobenzodiazepine (PBD) dimers or tomaymycin, indolinobenzodiazepines, imidazobenzothiadiazepines, or oxazolidino-benzodiazepines), nitroureas (carmustine, lomustine, chlorozotocin, fotemustine, nimustine, ranimustine), alkylsulfonates (busulfan, treosulfan, improsulfan, and piposulfan), triazenes (dacarbazine), platinum-based compounds (carboplatin, cisplatin, oxaliplatin), aziridines (benzodopa, carboquone, meturedopa, and uredopa), ethyleneimines and melamines (including altretamine, triethylenemelamine, triethylenephosphoramide, triethylenethio-phosphaoramide and trimethylolomelamine);
- plant alkaloids such as: Vinca alkaloids (vincristine, vinblastine, vindesine, vinorelbine, navelbine), taxoids (paclitaxel, docetaxol) and their analogues, Maytansinoids (DM1, DM2, DM3, DM4, maytansine and ansamitocins) and their analogues, cryptophycins (in particular cryptophycin 1 and cryptophycin 8), epothilones, eleutherobin, discodermolide, bryostatins, dolastatins, auristatins, tubulysins, cephalostatins, pancratistatins, sarcodictyin, spongistatins;
- DNA topoisomerase inhibitors such as: epipodophyllin (9-aminocamptothecin, camptothecin, crisnatol, daunomycin, etoposide, etoposide phosphate, irinotecan, mitoxantrone, novantrone, retinoic acids (retinols), teniposide, topotecan, 9-nitrocamptothecin (RFS 2000), mitomycins (mitomycin C), bortezomib;
- anti-metabolites such as: anti-folates (DHFR inhibitors (methotrexate, trimetrexate, denopterin, pteropterin, aminopterin (4-aminopteroic acid) and other analogues of folic acid), inhibitors of IMP dehydrogenase (mycophenolic acid, tiazofurin, ribavirin, EICAR), ribonucleotide reductase inhibitors (hydroxyurea, deferoxamine), pyrimidine analogs such as: uracil analogs (ancitabine, azacitidine, 6-azauridine, capecitabine, carmofur, cytarabine, dideoxyuridine, doxifluridine, enocitabine, 5-fluorouracil, floxuridine, ratitrexed), cytosine analogs (cytarabine, cytosine arabinoside, fludarabine), purine analogs (azathioprine, fludarabine, mercaptopurine, thamiprine, thioguanine), folinic acid;
- hormonal agents such as: anti-estrogens (megestrol, raloxifene, tamoxifen), LHRH agonists (goserelin, leuprolide acetate), anti-androgens (bicalutamide, flutamide, calusterone, dromostanolone propionate, epitiostanol, goserelin, leuprolide, mepitiostane, nilutamide, testolactone, trilostane), vitamin D3 analogues (CB 1093, EB 1089, KH 1060, cholecalciferol, ergocalciferol), photodynamic therapies (verteporfin, phthalocyanine, photosensitizer Pc4), cytokines (interferon-alpha, interferon-gamma, tumor necrosis (TNF), human proteins containing a TNF domain);
- kinase inhibitors such as: BIBW 2992, CYT387, E7080, axitinib, bafetinib, bosutinib, cabozantinib, dasatinib, erlotinib, gefitinib, imatinib, iniparib, ispinesib, lapatinib, masitinib, mubritinib, nilotinib, pazopanib, pegaptanib, ponatinib, ruxolitinib, sorafenib, sunitinib, tivozanib, vandetanib, vismodegib;
- poly(ADP-ribose)polymerase (PARP) inhibitors such as: BGB-290, CEP 9722, E7016, 3-aminobenzamide, niraparib, olaparib, talazoparib, veliparib;
- immunomodulators such as: thalidomide, lenalidomide, pomalidomide.

According to a particular embodiment of the disclosure, the active ingredient is selected from duocarmycin and its analogues, dolastatins, combretastatin and its analogues, calicheamicin, N-acetyl-y-calicheamycin (CMC), a derivative of calicheamycin, maytansin and its analogues, such as a maytansinoid-type derivative, for example DM1 and DM4, auristatins and their derivatives, such as auristatin E, auristatin EB (AEB), auristatin EFP (AEFP), monomethyl auristatin E (MMAE), monomethyl auristatin F (MMAF), tubulysin, disorazole, epothilones, echinomycin, estramustine, cemadotin, eleutherobin, methopterin, actinomycin, mitomycin C, camptothecin, a derivative of camptothecin, SN38, TK1, amanitine and its analogs, a pyrrolobenzodiazepine, a pyrrolobenzodiazepine dimer, a pyrrolopyridodiazepine, a pyrrolopyridodiazepine dimer, a DNA intercalator, a histone deacetylase inhibitor, or a (tyrosine) kinase inhibitor.

In another particular embodiment of the disclosure, the active ingredient is selected from pseudomonas exotoxin (PE), deBouganin, Bouganin, diphtheria toxin (DT) and ricin.

In a particular embodiment, the active ingredient is selected from methotrexate, an immunomodulator, duocarmycin, combretastatin, calicheamicin, monomethyl auristatin E (MMAE), monomethyl auristatin F (MMAF), maytansine, DM1, DM4, SN38, amanitine and its analogues, pyrrolobenzodiazepine, a pyrrolobenzodiazepine dimer, pyrrolopyridodiazepine, a pyrrolopyridodiazepine dimer, a histone deacetylase inhibitor, a (tyrosine) kinase inhibitor, and ricin, preferably the active ingredient is amanitine or MMAE, represented by the following formula:

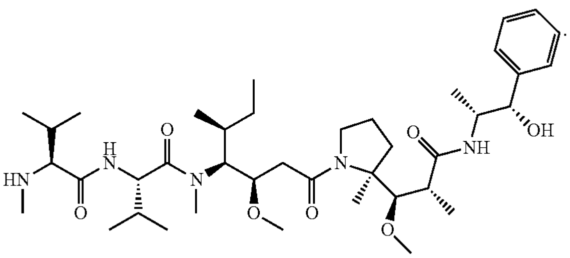 [SMILES: CC[C@H](C)[C@@H]([C@@H](CC(=O)N1CCC[C@@]1(C)[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

According to another aspect, the disclosure relates to a conjugate obtainable:

(c1) by conjugation between a protein comprising at least two disulfide bridges and a compound of formula (I) as defined above, or (c2) by conjugation between a protein comprising at least two disulfide bridges and a compound of formula (II) as defined above, or (c3) by reaction between a protein comprising at least two disulfide bridges, a compound of formula (I) and a compound of formula (V):

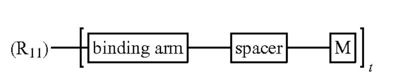

(V)

wherein:

$R_{11}$ is $R_7$—$(CH_2)_s$—CO—, $R_7$—$(CH_2)_s$—CONHCH$[CH_2CO\text{-}]_2$, $R_7$—$(CH_2)_s$—$(O—CH_2CH_2)_q$—CO—, $R_7$—$(CH_2)_s$—$(O—CH_2CH_2)_q$ —CONHCH$[CH_2CO\text{-}]_2$, or a compound of formula:

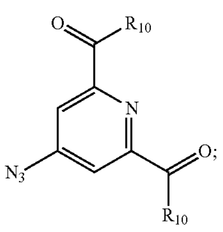

$R_7$ is as defined above;

$R_{10}$ is a direct bond, a peptide residue (preferably a dipeptide residue), —$(CR_cR_d)_rR_5$, or —$(CH_2CH_2O)_qR_5$, $R_c$, $R_d$, $R_5$, q and r being as defined above for the compound of formula (I); preferably $R_{10}$ is a direct bond or a peptide residue, preferably a dipeptide residue;

each q is an integer ranging from 1 to 12;

each s is an integer ranging from 0 to 6;

t is 1 or 2, preferably t is 1;

the binding arm, the spacer and M are as defined above.

In the context of the conjugate definition above, the compounds 2,6-bis[2,6-bis(bromomethyl)phenyl]benzoic acid and 1,3-bis[[3,5-bis(bromomethyl)phenoxy]-methyl]-5-prop-2-ynoxy-benzene are an integral part of formula (I) for alternatives (c1) and (c3).

In the reaction described in alternative (c3), the compounds of formula (I) and of formula (V) react with each other by carrying out a reaction called "click" reaction. More specifically, the click reaction between the compound of formula (I) and the compound of formula (V) takes place between a diene (for example an azide or a diazo) and a dienophile (for example an alkene or an alkyne), each of these species being respectively provided by $R_7$ on the one hand in the compound of formula (I), by $R_{11}$, on the other hand in the compound of formula (V).

It is therefore understood that the click reaction can occur:

between a diene carried by the $R_7$ originating from the compound of formula (I) and a dienophile carried by the $R_{11}$ originating from the compound of formula (V); or between a dienophile carried by the $R_7$ originating from the compound of formula (I) and a diene carried by the $R_{11}$ originating from the compound of formula (V).

Click reactions are well known to the person skilled in the art, and include for example a cycloaddition reaction between a dienophile and a diene. Examples of click reactions are shown in the following scheme:

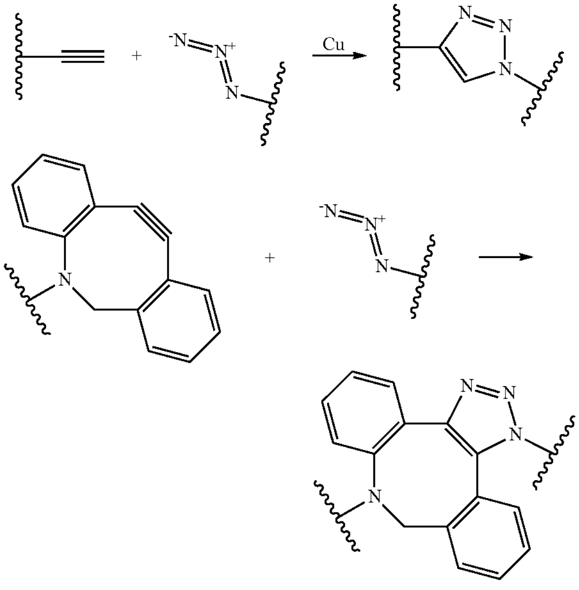

-continued

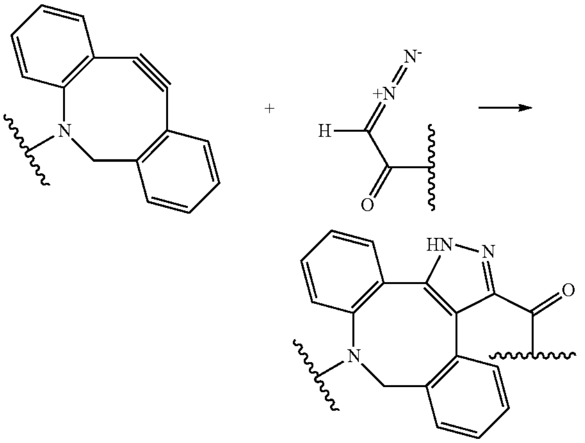

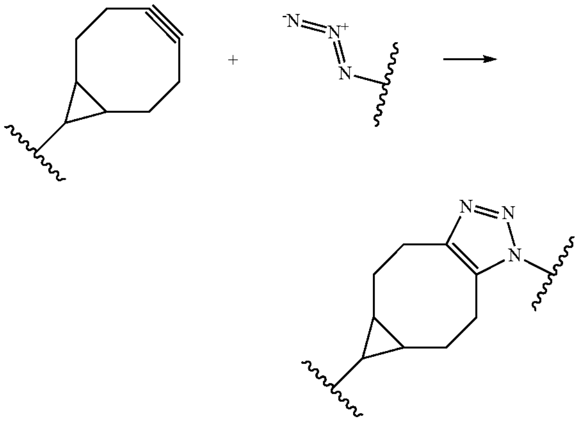

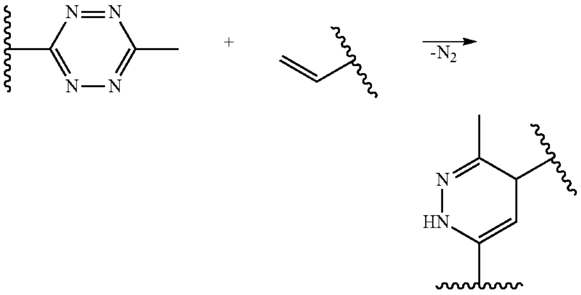

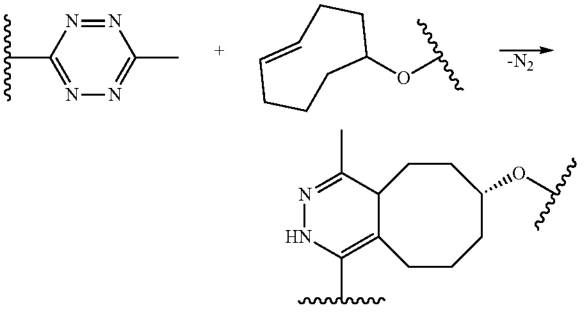

In these examples, a single regio-isomer per reaction has been represented, it being understood that the cycloaddition reactions can generate several regio-isomers.

In one embodiment, the click reaction is carried out between a compound of formula (I) and a compound of formula (V) wherein $R_{11}$ is $N_3$—$(CH_2)_5$—CO—, t=1 and the binding arm is represented by the formula (VI):

(VI)

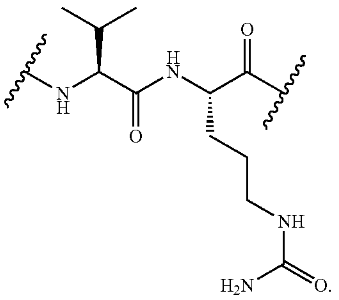

In one embodiment, the protein comprising at least two disulfide bridges is an antibody or an antibody fragment as defined above. In this embodiment, the antibody or antibody fragment binds to the attachment head by substitution of the leaving groups represented by the substituent X in formula (I). Still in this embodiment, the reactions (c1) to (c3) described above lead to the reconstruction of the antibody, after reduction of the interchain disulfide bridges. In the context of the present disclosure, the reconstruction of an antibody is defined as obtaining a majority of whole LHHL antibodies. The proportion of whole LHHL antibodies and of the other species (LHH, HH, LH, H, L) is determined using the optical density measured by analysis on SDS-PAGE gel under denaturing reducing conditions. A good reconstruction is achieved when the proportion of LHHL exceeds 50%.

In one embodiment, the various reactions (c1) to (c3) allow to obtain a "molecule-to-antibody ratio" (MAR) (or ratio of "attached" or "conjugated" molecules per antibody) comprised in the range from about 0.50 to about 2.50. In one embodiment, the antibody or antibody fragment is conjugated on average to 1.00±0.50 (that is to say any value from 0.50 to 1.50, for example 0.50; 0.51; . . . ; 1.49; 1.50) molecule, preferably 1.00±0.30 molecule. In one embodiment, the antibody or antibody fragment is conjugated on average to 2.00±0.50 (that is to say any value from 1.50 to 2.50, for example 1.50; 1.51; . . . ; 2.49; 2.50) molecule(s), preferably 2.00±0.30 molecule(s). In the context of the present disclosure, the term "molecule" should be understood either as a compound of formula (I), or a compound of formula (II), or the product of the (click) reaction between a compound of formula (I) and a compound of formula (V).

The conjugate formed at the end of reactions (c1), (c2) or (c3) can be represented schematically by the following structure:

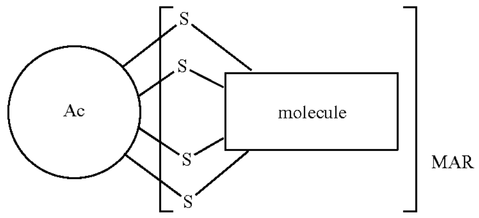

wherein Ac is an antibody or antibody fragment; the molecule is as defined above (it being understood that the antibody or the antibody fragment binds to the attachment head of the molecule by substitution of the leaving groups X); and MAR represents the average number of molecule(s) bound to the antibody or the antibody fragment.

The MAR is determined for each species (LHHL, LH, L, H, HH, LHH) by HRMS (High Resolution Mass Spectrometry) analysis under denaturing conditions. The average MAR is obtained from the MAR per weighted species by the proportions of the species observed in analysis on SDS-PAGE gel under denaturing non-reducing conditions. Only the majority LHHL and LH species were considered for this calculation, the sum of the proportions of the other species (L, H, HH and LHH) being less than 18%. The sum of the proportions of the LHHL and LH species was therefore reduced to 100% by not taking into account the other species.

The "half-antibody" LH species is observed under denaturing conditions. In solution (in native conditions) this species is not present in isolation, the weak interactions keep the two LH together. This is why the MAR of the non-reconstructed LH-LH species corresponds to 2 times the MAR observed on the LH species.

The average MAR was therefore calculated using the following formula:

$$\text{Average } MAR = \frac{\%\ LHHL * MAR\ LHHL + \%\ LH * MAR\ LH * 2}{100}. \quad \text{[Math 1]}$$

According to another aspect, the disclosure relates to a composition comprising one or more conjugates as defined above. The composition can be a pharmaceutical composition containing one or more pharmaceutically acceptable excipients and/or carriers.

The compounds of formulas (I), (II) and (V) can be prepared according to techniques described in the literature and/or in the examples below.

The bioconjugation reaction (c1) or (c2) can be implemented by reaction of the protein comprising at least two disulfide bridges with the compound of formula (I) or (II) to be conjugated, in the presence of a reducer. In one embodiment the protein is in solution in a buffer. In one embodiment, the reducer is added before the compound to be conjugated.

In another embodiment, the reducer and the compound to be conjugated are added simultaneously.

The reaction (c3) can be carried out by (i) reaction, in the presence of a reducer, of the protein comprising at least two disulfide bridges with the compound of formula (I) then addition of the compound of formula (V) and click reaction or by (ii) reaction, in the presence of a reducing agent, of the protein comprising at least two disulfide bridges with a compound resulting from a prior click reaction between the compounds of formula (I) and (V). In one embodiment the protein is in solution in a buffer.

The disclosure is illustrated by the examples below, given purely by way of illustration. In these examples, the following abbreviations are used:

AcOEt=ethyl acetate
APS=ammonium persulfate
BSA=bovine serum albumin
BnOH=benzyl alcohol
$CHCl_3$=chloroform
DBCO=dibenzylcyclooctyne
DCM=dichloromethane
DIPEA=N,N-diisopropylethylamine
DMF=N,N-dimethylformamide
DMSO=dimethylsulfoxide
EDTA=ethylenediaminetetraacetic acid
EEDQ=N-ethoxycarbonyl-2-ethoxy-1,2-dihydroquinoline
EtOH=ethanol
FmocCl=fluorenylmethoxycarbonyl chloride
HATU=O-(7-azabenzotriazol-1-yl)-N,N,N,N'tetramethyluronium hexafluorophosphate
HCl=hydrochloric acid
LiOH=lithium hydroxide
MeCN=acetonitrile
MeOH=methanol
$MgSO_4$=magnesium sulfate
NaCl=sodium chloride
$Na_2CO_3$=sodium carbonate
$NaHCO_3$=sodium hydrogen carbonate
$NaN_3$=sodium azide
$PBr_3$=phosphorus tribromide
Pd/C=palladium on charcoal
$Pd(OH)_2/C$=palladium hydroxide on charcoal
$SiO_2$=silica
$SOCl_2$=thionyl chloride
RT=room temperature (20° C. unless otherwise specified)
TBAF: tetrabutylammonium fluoride
TBDMSOTf=tert-butyldimethylsilyl trifluoromethanesulfonate
TFA=trifluoroacetic acid
THF=tetrahydrofuran
Tr=Retention time
v/v=volume to volume ratio Analytical Methods Nuclear Magnetic Resonance (NMR) Spectroscopy The nuclear magnetic resonance (NMR) spectra of proton $^1H$, carbon $^{13}C$ and fluorine $^{19}F$ were carried out on a Bruker device Ultrashield 300 (300 MHz ($^1H$), 75 MHz ($^{13}C$) and 282 MHz ($^{19}F$)). The analyzes were carried out in deuterated chloroform ($CDCl_3$), in deuterated dimethyl sulfoxide (DMSO-$d_6$), in heavy water ($D_2O$) or in deuterated methanol ($MD_3OD$).

The chemical shifts (δ) are measured in parts per million (ppm) relative to the residual signal of deuterated chloroform ($CDCl_3$) ($\delta^1H$=7.2 ppm, $\delta^{13}C$=77.1 ppm), to the residual signal of the deuterated dimethyl sulfoxide (DMSO-de) ($\delta^1H$=2.50 ppm, $\delta^{13}C$=39.5 ppm), to the residual signal of heavy water ($\delta^1H$=4.79 ppm), or to the residual signal of deuterated methanol ($\delta^1H$=3.31 ppm, $\delta^{13}C$=49.0 ppm).

The coupling constants (J) are expressed in Hertz (Hz) and the multiplicity is described as follows: d=doublet, dd=doublet of doublet, dt=doublet of triplet, m=multiplet, p=pentuplet, s=singlet, t=triplet. In order to clarify the reading of the NMR analyses, the numbering of the atoms for the attribution of the signals was fixed arbitrarily.

High Resolution Mass Spectrometry (HRMS)

The exact mass of the synthesized compounds was determined by high resolution mass spectrometry (HRMS) in positive or negative mode with the ESI electrospray ionization technique, either on a Bruker maXis mass spectrometer coupled with a Dionex Ultimate 3000 RSLC system from the "Research Federation" platform from the ICOA/CBM (FR2708), or on a Waters Vion IMS QTof mass spectrometer coupled to a Waters Acquity UPLC H-Class system from the GICC (EA7501).

Denaturing High Resolution Mass Spectrometry (HRMS)

Method 1: The analysis of the conjugates was carried out on a sample previously deglycosylated or not. In the case of a deglycosylated sample, it was diluted to a concentration of 1 µg/µL then N-glycosidase F (0.02 units/µg of sample) was added and the sample was incubated at 37° C. for at least 16 h.

The analysis was performed on a Vion IMS Qtof mass spectrometer coupled to an Acquity UPLC H-Class system from Waters (Wilmslow, UK). Before the analysis, the samples (800 ng) were injected on an XBridge BEH300 C4 2.1×50 mm, 1.7 μm column, or on an XBridge BEH300 C4 2.1×30 mm, 5 μm column heated to 90° C. A desalting step was carried out with an isocratic gradient of 95% solvent A ($H_2O$+0.1% formic acid) and 5% solvent B (MeCN+0.1% formic acid) for 1.5-2 min at 0.5 mL/min. Then, the elution of the sample was carried out with a gradient of 20% to 35% of solvent B over 7 min, from 50% to 90% of solvent B over 3 min, and an isocratic of 1 min at 90% of B, that is to say with a gradient of 5% to 50% of solvent B over 2.9 min, from 50% to 90% of solvent B over 0.5 min, an isocratic of 0.5 min at 90% of B, with a flow rate of 0.4 mL/min. A bypass valve was programmed to allow the solvent to enter the spectrometer between 3 and 7.5 min only. Mass spectrometry data were acquired in positive mode with an ESI source over an m/z range of 500 to 4000 at a scan rate of 1 Hz and analyzed using UNIFI 1.9.4 software and the MaxEnt algorithm for deconvolution. The average MAR per species (=average number of conjugated molecules to the antibody used for the bioconjugation reaction) was determined using the intensity of the peaks of the species observed.

Method Z: Spectrometric analysis of some conjugates was performed on a Bruker maXis mass spectrometer coupled with a Dionex Ultimate 3000 RSLC system. Prior to MS analysis, samples (5 μg) were desalted on a MassPREP desalting column (2.1×10 mm, Waters), heated to 80° C. using a 0.1% aqueous formic acid solution as solvent A and a 0.1% solution of formic acid in acetonitrile as solvent B at 500 μL/min. After 1 min, a linear gradient from 5 to 90% B in 1.5 min was applied. MS data was acquired in positive mode with an ESI source over an m/z range of 900 to 5000 at 1 Hz and analyzed using DataAnalysis 4.4 software (Bruker) and the MaxEnt algorithm for deconvolution. The average MAR per species (=average number of molecules conjugated to the antibody used for the bioconjugation reaction) was determined using the intensity of the peaks of the species observed.

SDS-PAGE Gel Under Denaturing, Non-Reducing or Reducing Conditions

The samples were analyzed by SDS-PAGE tris-HCl acrylamide gel. A 4% acrylamide stacking gel on a 6-7% acrylamide running gel were used. 4× Laemmli buffer (0.3 mM bromophenol blue; 2 M glycerol, 20 mM TrisBase; 0.04% sodium dodecyl sulfate) was added to the samples (1.6 μg). Under reducing conditions, the samples were reduced using a 10% solution of dithiothreitol (DTT) in water (10% v/v). Then the samples were incubated at 95° C. for 10 min. A high amplitude molecular weight marker (Invitrogen SeeBlue® Plus2 Prestained Standard) and the native antibody were used to estimate protein molecular weights. The gel was run at 100 V for 10 min then at 140 V for 35 min, in NuPAGE running buffer (50 mM MOPS; 50 mM TrisBase; 0.1% SDS (v/v); 1 mM EDTA, pH 7.3). After washing with water, the gel was stained with Coomassie blue (Thermo Scientific Imperial™ Protein Stain). Densitometric analysis was performed using ImageJ software and a Windows Vanilla filter was applied for black and white analysis. Under denaturing non-reducing conditions, the relative optical density of LHHL and LH species was used to determine the average MAR of the conjugate. Under denaturing reducing conditions, the relative optical density measured for the LHHL species determined the reconstruction of the antibody (in %).

Bioconjugation Reactions

Preparation of Solutions

Bioconjugation buffer 1: 1× phosphate buffer at pH 8.3, with a final NaCl concentration of 180 mM and a final EDTA concentration of 1 mM.

Bioconjugation buffer 2: 1× borate buffer at pH 8.3, with a final NaCl concentration of 25 mM and a final EDTA concentration of 1 mM.

Reducer 1: Solution of tris(2-carboxyethyl)phosphine hydrochloride (TCEP·HCl) at a concentration of 1 mM in the bioconjugation buffer.

Reducer 2: Solution of dithiothreitol (DTT) at a concentration of 1 mM in the bioconjugation buffer.

Bioconjugation Reaction 1:

The antibody solution in bioconjugation buffer (1.0 eq) was placed under argon. The reducing agent (8.0-12.0 eq) was then added and the reaction medium was incubated at 37° C. for 2 h. Then the solution of compound to be conjugated (5.0-15.0 eq, preferably 5.0-12.0 eq or 10.0-15.0 eq)) was added under argon and the reaction medium was stirred at 37° C. for 2 h 30.

Bioconjugation Reaction 2:

The antibody solution in bioconjugation buffer (1.0 eq) was placed under argon. The solutions of compound to be conjugated (1.0-15.0 eq, preferably 8.0-12.0 eq) then of reducing agent (7.0-12.0 eq) were added and the reaction medium was stirred under argon at 37° C. for 2 h 30.

Bioconjugation Reaction 3:

The antibody solution in bioconjugation buffer (1.0 eq) was placed under argon. The solutions of the compound of formula (I) (1.0-15.0 eq, preferably 8.0-12.0 eq or 10.6-12.0 eq) then of reducing agent (7.0 eq) were added and the reaction medium was stirred under argon at 37° C. for 2 h 30. The solution of the compound of formula (V) (1.0-15.0 eq, preferably 8.8-14.4 eq, for example 11.7 eq) was then added and the reaction medium was stirred at 25° C. for 17 h.

Bioconjugation Reaction 4:

The antibody solution in bioconjugation buffer (1.0 eq) was placed under argon. The reducing agent (8.0-12.0 eq) was then added and the reaction medium was incubated at 37° C. for 2 h. Then the solution of compound to be conjugated (10.0-15.0 eq) was added under argon and the reaction medium was stirred at 37° C. for 2 h 30. The solution of the compound of formula (V) (11, 0-30.0 eq) was then added and the reaction medium was stirred at 25° C. for 17 h.

EXAMPLES

Preparation 1: benzyl isonicotinate (1)

(1)

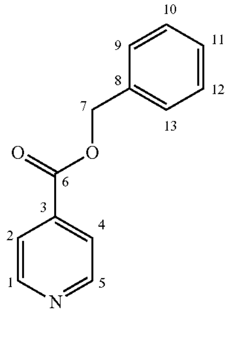

Isonicotinic acid (5.00 g; 40.614 mmol; 1.0 eq) was dissolved in $SOCl_2$ (15 mL; 206.775 mmol; 5.1 eq) and heated at reflux for 15 h. After returning to RT, the excess $SOCl_2$ was removed by evaporation under reduced pressure, then the residue obtained was dissolved in anhydrous DCM (55 mL). BnOH was added (4.2 mL; 40.614 mmol; 1.0 eq) and the mixture was stirred at reflux for 10 h. After returning to RT, the reaction medium was neutralized with a saturated solution of $NaHCO_3$ and extracted with DCM (3×100 mL). The organic phases were combined, washed with a saturated NaCl solution, dried on $MgSO_4$ and concentrated under reduced pressure. The product obtained was purified by flash chromatography ($SiO_2$, cyclohexane/AcOEt 50:50) to give (1) (6.97 g; 80%) in the form of a colorless oil.

$^1H$ NMR (300 MHz, DMSO) δ 8.80 (dd; 1=6.1; 1.6 Hz; $2H_{1,5}$); 7.86 (dd; J=6.1; 1.6 Hz, $2H_{2,4}$); 7.56-7.29 (m; $5H_{9\text{-}13}$); 5.39 (s; $2H_7$).

$^{13}C$ NMR (75 MHz, DMSO) δ 165.0 ($1C_6$); 151.3 ($2C_{1,5}$); 137.2 ($1C_3$); 136.1 ($1C_8$); 129.0 ($2C_{10,12}$); 128.8 ($1C_{11}$); 128.6 ($2C_{9,13}$); 123.0 ($2C_{2,4}$); 67.4 ($1C_7$).

HRMS (ESI): neutral mass calculated for $C_{13}H_{11}NO_2$ [M]: 213.0790; observed 213.0796.

Preparation 2: Benzyl 2,6-bis(hydroxymethyl) isonicotinate (2)

(2)

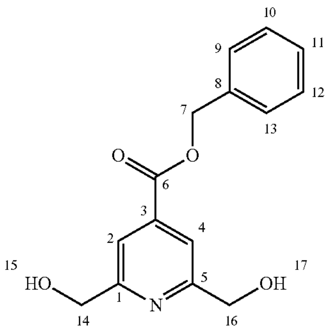

Benzyl isonicotinate (1) (2.48 g; 11.630 mmol; 1.0 eq) was dissolved in MeOH (43 mL), stirred at 50° C. and concentrated $H_2SO_4$ (320 μL; 6.016 mmol; 0.5 eq) was added. A solution of APS (26.500 g; 116.126 mmol; 10.0 eq) in water (43 mL) was added in two steps: a first rapid addition of 30 drops, a white suspension is formed, then fast dropwise for 5 min. The reaction ran up to 75° C., then the resulting yellow solution was stirred at 50° C. for an additional 1 h. After returning to RT, MeOH was evaporated under reduced pressure. 50 mL of AcOEt were added and the medium was neutralized by adding a saturated solution of $NaHCO_3$. The aqueous phase was extracted with AcOEt (3×100 mL) and the combined organic phases were washed with saturated NaCl solution, dried on $MgSO_4$, then concentrated under reduced pressure. The crude was purified by flash chromatography ($SiO_2$, DCM/MeOH, 95:5) to give (2) (1.56 g; 49%) in the form of a beige solid.

$^1H$ NMR (300 MHz, DMSO) δ 7.81 (s; $2H_{2,4}$); 7.55-7.32 (m; $5H_{9\text{-}13}$); 5.60 (t; 3=5.9 Hz; $2H_{15,17}$); 5.40 (s; $2H_7$); 4.59 (d; J=5.9 Hz; $4H_{14,16}$). 13C NMR (75 MHz, DMSO) δ 165.0 ($1C_6$); 162.8 ($2C_{1,5}$); 138.0 ($1C_3$); 135.7 ($1C_8$); 128.6 ($2C_{10,12}$); 128.4 ($1C_{11}$); 128.3 ($2C_{9,13}$); 117.0 ($2C_{2,4}$); 66.9 ($1C_7$); 63.9 ($2C_{14,16}$). HRMS (ESI): neutral mass calculated for $C_{15}H_{15}NO_4$ [M]: 273.1001; observed 273.1001.

Preparation 3: Benzyl 2,6-bis(((tert-butyldimethylsilyl)oxy)methyl)-isonicotinate (3)

(3)

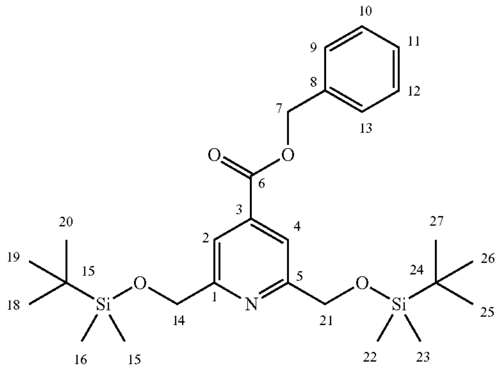

Benzyl 2,6-bis(hydroxymethyl) isonicotinate (2) (1.56 g; 5.708 mmol; 1.0 eq) was dissolved in anhydrous DCM (12 mL), 2,6-lutidine (3.6 mL; 28.542 mmol; 5.0 eq) was added and the solution was cooled to 0° C. TBDMSOTf (5.5 mL; 23.974 mmol; 4.2 eq) was added dropwise over 10 min, then the reaction medium was stirred under argon at RT for 19 h. The medium was cooled to 0° C. then neutralized by adding a saturated solution of $NaHCO_3$. The aqueous phase was extracted with DCM (3×100 mL) and the combined organic phases were washed with saturated NaCl solution, dried on $MgSO_4$, filtered, then concentrated under reduced pressure. The crude was purified by flash chromatography ($SiO_2$, cyclohexane/AcOEt, 90:10) to give (3) (2.50 g; 87%) in the form of a beige solid.

$^1H$ NMR (300 MHz, $CDCl_3$) δ 7.97 (s; $2H_{2,4}$); 7.57-7.28 (m; $5H_{9,13}$); 5.39 (s; $2H_7$); 4.84 (s; $4H_{14,21}$); 0.95 (s; $18H_{18,20,25,27}$); 0.12 (s; $12H_{15,16,22,23}$).

$^{13}C$ NMR (75 MHz, $CDCl_3$) δ 165.6 ($1C_6$); 161.8 ($2C_{1,5}$); 138.9 ($1C_3$); 135.6 ($1C_8$); 128.8 (2C10,12); 128.5 ($1C_{11}$); 128.2 ($2C_{9,13}$); 117.8 ($2C_{2,4}$); 67.4 ($1C_7$); 65.9 ($2C_{14,21}$); 26.0 ($6C_{18\text{-}20,25\text{-}27}$); 18.5 ($2C_{17,24}$); −5.2 ($4C_{15,16,22,23}$).

HRMS (ESI): m/z calculated for $C_{27}H_{44}NO_4Si_2[M+H]^+$: 502.2803; observed 502.2801.

Preparation 4: 2,6-bis(((tert-buty/dimethylsilyl)-oxy) methyl)isonicotinic acid (4)

(4)

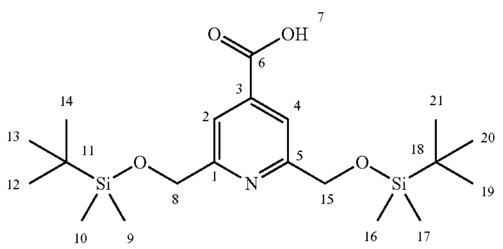

Benzyl 2,6-bis(((tert-butyldimethylsilyl)oxy)methyl) isonicotinate (3) (2.50 g; 4.982 mmol; 1.0 eq) was dissolved in 60 mL of a MeOH/AcOEt mixture (5:1) and the solution was degassed with argon for 15 min. Pd/C at 10% by mass (250 mg; 10% m/m) was added and the reaction medium was stirred at RT under a hydrogen atmosphere for 5 h. The reaction medium was filtered through Dicalite™ (MeOH rinsing). The filtrate was concentrated under reduced pressure to give (4) (1.93 g; 94%) in the form of a white solid.

$^1$H NMR (300 MHz, $CDCl_3$) δ 8.01 (s; $2H_{2,4}$); 4.90 (s; $4H_{8,15}$); 0.97 (s; $18H_{12\text{-}14,19\text{-}21}$); 0.13 (s; $12H_{9,10,16,17}$).

$^{13}$C NMR (75 MHz, $CDCl_3$) δ 170.2 ($1C_6$); 161.8 ($2C_{1,5}$); 139.3 ($1C_3$); 118.4 ($2C_{2,4}$); 65.7 ($2C_{8,15}$); 26.1 ($6C_{12\text{-}14,19\text{-}21}$); 18.6 ($2C_{1,18}$); −5.2 ($4C_{9,10,16,17}$).

HRMS (ESI): neutral mass calculated for $C_{20}H_{37}NO_4Si_2$ [M]: 411.2261; observed 411.2257.

Preparation 5: 6-(Fmoc-amino)hexanoic acid (5)

(5)

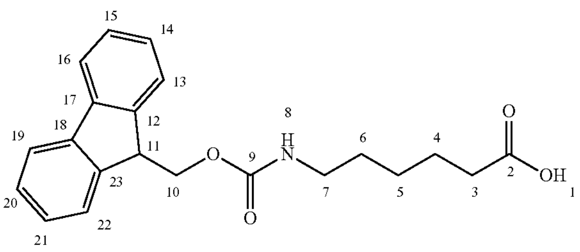

6-aminohexanoic acid (1.00 g; 7.623 mmol; 1.0 eq) was dissolved in a water/1,4-dioxane mixture (1:1; 38 mL) at 0° C. $Na_2CO_3$ (2.42 g; 22.832 mmol; 3.0 eq) was added and the reaction medium was stirred at 0° C. for 10 min. FmocCl (1.97 g; 7.623 mmol; 1.0 eq) was added and the reaction medium was stirred at RT for 5 h. The medium was acidified by adding a 1M HCl solution until a pH of 6 was reached and the precipitate formed was filtered and rinsed with water (3×20 mL). The solid was purified by flash chromatography ($SiO_2$, DCM/MeOH, 95:5) to give (5) (2.32 g; 86%) in the form of a white solid.

$^1$H NMR (300 MHz; DMSO) δ 7.89 (d; 3=7.4 Hz; $2H_{16,19}$); 7.68 (d; J=7.4 Hz; $2H_{13,22}$); 7.48-7.38 (m; $2H_{15,20}$); 7.37-7.29 (m; $2H_{14,21}$); 7.26 (t; J=5.6 Hz; $1H_8$); 4.35-4.25 (m; $2H_{10}$); 4.25-4.13 (m; $1H_{11}$); 3.04-2.87 (m; $2H_7$); 2.18 (t; 3=7.3 Hz; $2H_3$); 1.58-1.31 (m; $4H_{4,6}$); 1.31-1.18 (m; $1H_5$).

$^{13}$C NMR (75 MHz, DMSO) δ 174.5 ($1C_2$); 156.1 (1C9); 144.0 ($2C_{12,23}$); 140.8 ($2C_{17,18}$); 127.6 ($2C_{15,20}$); 127.1 ($2C_{14,21}$); 125.2 ($2C_{13,22}$); 120.1 ($2C_{16,19}$); 65.2 ($1C_{10}$); 46.8 ($1C_{11}$); 39.7 under DMSO ($1C_7$); 33.7 ($1C_3$); 29.1 ($1C_6$); 25.8 ($1C_5$); 24.2 ($1C_4$).

HRMS (ESI): neutral mass calculated for $C_{21}H_{23}NO_4$ [M]: 353.1627; observed 353.1633.

Preparation 6: MMAE 6-aminohexanamide-valine-citrulline-p-aminobenzoyl carbamate, salt of TFA (6)

(6)

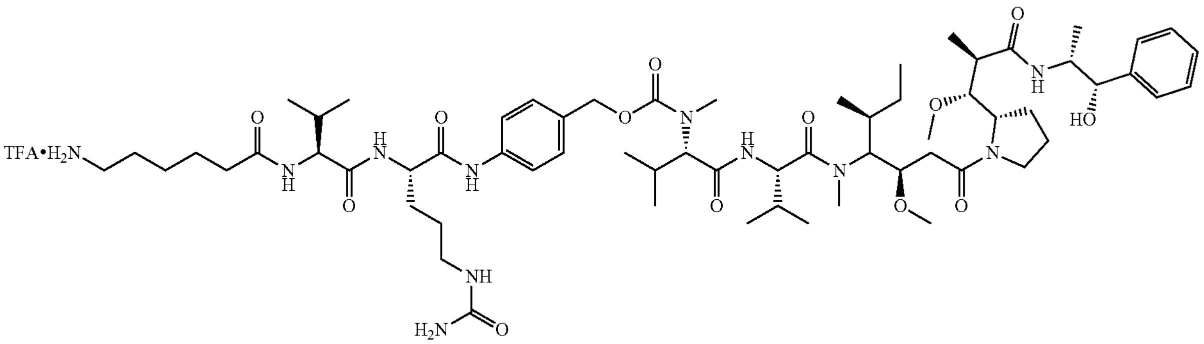

6-(Fmoc-amino)hexanoic acid (5) (11.8 mg; 0.034 mmol; 2.0 eq) was dissolved in anhydrous DMF (300 μL), the solution was cooled to 0° C., then HATU (25.5 mg; 0.067 mmol; 4.0 eq) and 2,6-lutidine (5.8 μL; 0.050 mmol; 3.0 eq) were added. The activation solution was stirred under argon at 0° C. for 15 min. A solution of MMAE valine-citrulline-p-aminobenzoyl carbamate trifluoroacetic acid salt (20.7 mg; 0.017 mmol; 1.0 eq), dissolved in anhydrous DMF (300 μL) in the presence of 2,6-lutidine (5.8 μL; 0.050 mmol; 3.0 eq), was added in the middle of activation. The reaction medium obtained was stirred under argon at RT for 21 h. Piperidine (120 μL, 20% v/v) was added and the reaction medium was stirred under argon at RT for 2 h. The mixture was diluted by 2 with MeOH and purified by semi-preparative high-pressure liquid chromatography ($t_R$=15.8 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and acetonitrile (solvent B); gradient 20 to 100% B over 32 min then 100% B over 6 min at 17.1 mL/min) to give (6) (17.2 mg; 76%) in the form of a white lyophilisate.

$^1$H NMR (300 MHz, DMSO) δ (ppm) 10.14-9.95 (m; 1H); 8.41-8.26 (m; 1H); 8.19-8.06 (m; 1H); 7.91 (d; J=8.7 Hz; 1H); 7.83 (d; J=8.7 Hz; 1H); 7.76-7.53 (m; 5H); 7.40-7.22 (m; 5H); 7.21-7.12 (m; 1H); 6.01 (s; 1H); 5.43 (s; 3H); 5.18-4.91 (m; 3H); 4.82-4.56 (m; 2H); 4.52-4.34 (m; 3H); 4.32-4.15 (m; 3H); 4.08-3.89 (m; 4H); 3.35-3.27 (m; 1H); 3.27-3.08 (m; 8H); 3.08-2.92 (m; 4H); 2.91-2.82 (m; 3H); 2.82-2.71 (m; 3H); 2.47-2.34 (m; 3H); 2.33-2.22 (m; 2H); 2.22-2.06 (m; 4H); 2.05-1.87 (m; 2H); 1.87-1.63 (m; 4H); 1.62-1.42 (m; 6H); 1.39-1.21 (m; 4H); 1.08-0.94 (m; 6H); 0.94-0.52 (m; 21H).

HRMS (ESI): neutral mass calculated for $C_{64}H_{105}N_{11}O_{13}$ [M]: 1235.7893; observed 1235.7889.

Example 1: Methyl 2,3-bis(2,6-bis(bromomethyl) isonicotinamido)propanoate (11)

General reaction scheme

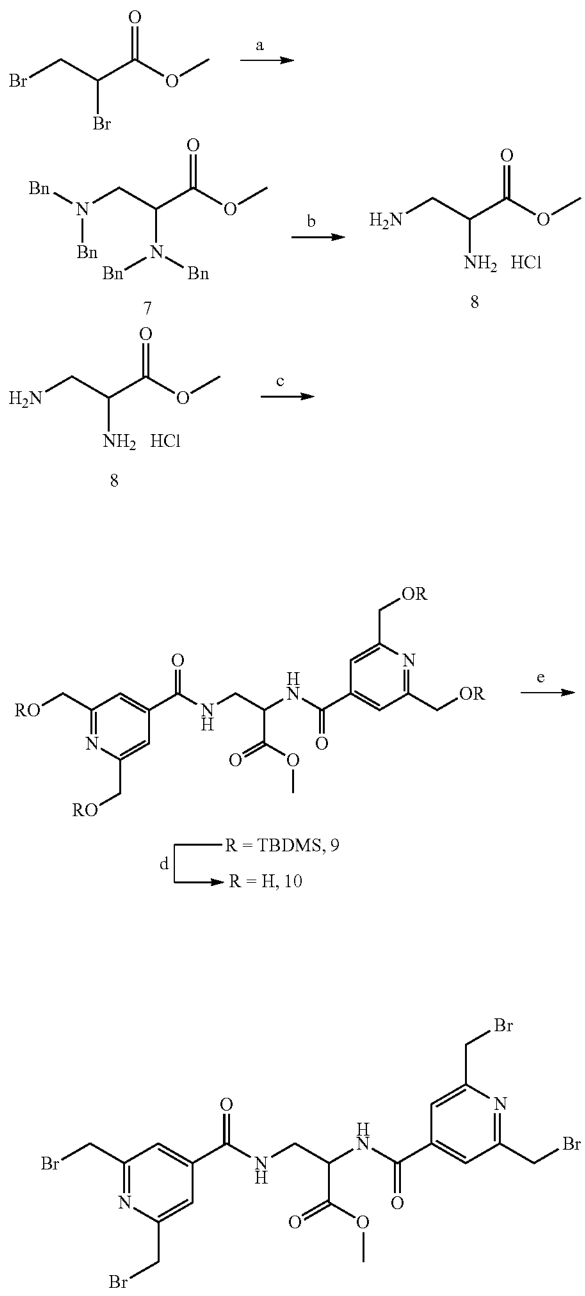

7

8

8

R = TBDMS, 9

R = H, 10

11 a $Bn_2NH$, EtOH, 1 h 30, 71° C.;
b $H_2$, $Pd(OH)_2/C$, 1,1,2-trichloroethane, MeOH, 64 h, RT;
c HATU, 2,6-lutidine, DIPEA, DMF, compound 4, 22 h 20, RT;
d TBAF, THF, 5 h 30, RT;
e $PBr_3$, MeCN, 2 h 15, 45° C.

(a) $Bn_2NH$, EtOH, 1 h30, 71° C.; (b) $H_2$, $Pd(OH)_2/C$, 1,1,2-trichloroethane, MeOH, 64 h, RT; (c) HATU, 2,6-lutidine, DIPEA, DMF, compound 4, 22 h 20, RT; (d) TBAF, THF, 5 h 30, RT; (e) $PBr_3$, MeCN, 2 h15, 45° C.

Step 1: methyl 2,3-bis(dibenzylamino) propanoate (7)

(7)

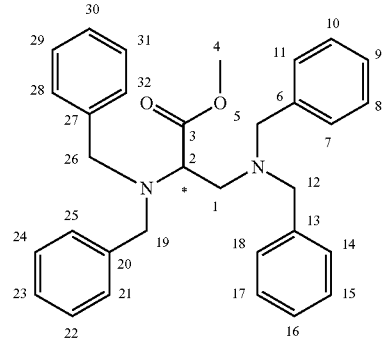

Racemic methyl 2,3-dibromopropanoate (154.4 µL; 1.22 mmol; 1.0 eq) was dissolved in 6 mL of absolute EtOH. Then $Bn_2NH$ (939 µL; 4.88 mmol; 4.0 eq) was added slowly with stirring, a precipitate formed after approximately 1 min. The reaction medium was stirred under argon at reflux (71° C.) for 1 h30. The amine salts were filtered on a frit. Then the filtrate was evaporated under reduced pressure. The beige solid obtained was taken up in DCM (20 mL) then washed with water (2×20 mL) and saturated NaCl solution (1×20 mL).

The organic phase was then dried on $MgSO_4$ and concentrated under reduced pressure. The product was purified by flash chromatography ($SiO_2$, cyclohexane/AcOEt 80:20) to give (7) (471 mg; 81%) in the form of a colorless oil.

$^1H$ NMR (300 MHz, $CDCl_3$) δ 7.38-7.14 (m; $20H_{7-11,14-18,21-25,28-32}$); 3.82 (d; J=14.0 Hz; $2H_{5,12,19,26}$); 3.73 (s; $3H_4$); 3.68 (dd; 3=8.6, 5.3 Hz; $1H_2$); 3.55-3.37 (m; $6H_{5,12,19,26}$); 3.01 (dd; J=12.8; 8.6 Hz; $1H_1$); 2.72 (dd; J=12.8; 5.3 Hz; $1H_1$).

$^{13}C$ NMR (75 MHz, $CDCl_3$) δ 172.7 ($1C_3$); 139.7 ($2C_{6,13,20,27}$); 139.0 ($2C_{6,13,20,27}$) 129.1 ($4C_{7,11,14,15,21,25,28,32}$); 129.0 ($4C_{7,11,14,18,21,25,28,32}$); 128.3 ($4C_{8,10,15,17,22,24,29,31}$); 128.2 ($4C_{8,10,15,17,22,24,29,31}$); 127.1 ($2C_{9,16,23,30}$); 127.0 ($2C_{9,16,23,30}$); 60.1 ($1C_2$); 58.4 ($4C_{5,12,19,26}$); 55.1 ($4C_{5,12,19,26}$); 54.3 ($1C_1$); 51.2 ($1C_4$).

HRMS (ESI): m/z calculated for $C_{32}H_{35}N_2O_2[M+H]^+$: 479.2693; observed 479.2693.

Step 2: methyl 2,3-diaminopropanoate hydrochloride (8)

(8)

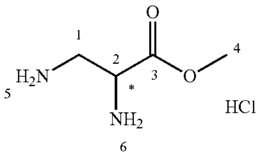

Methyl 2,3-bis(dibenzylamino) propanoate (7) (219.6 mg; 0.459 mmol; 1.0 eq) was dissolved in MeOH (3.5 mL).

1,1,2-trichloroethane (119.6 μL; 1.29 mmol, 2.8 eq) was added and the solution was degassed with argon for 15 min. Then $Pd(OH)_2/C$ at 20% by mass (87.8 mg, 40% m/m) was added. The reaction medium was stirred under a hydrogen atmosphere at RT for 64 h. $Pd(OH)_2/C$ was filtered on Dicalite™ then the filtrate was concentrated under reduced pressure. The product (8) (89.8 mg, quantitative yield) was obtained in the form of a yellow heterogeneous oil.

$^1H$ NMR (300 MHz, $D_2O$) δ 4.38 (dd; J=7.9; 5.5 Hz; $1H_2$); 3.75 (s; $3H_4$); 3.57-3.30 (m; 2H1).

$^1H$ NMR (300 MHz, DMSO) δ 8.69 (s; $5H_{5,6}$); 4.40 (t; J=6.1 Hz; $1H_2$); 3.79 (s; $3H_4$); 3.34-3.25 (m, 2H1; under the $H_2O$ of DMSO).

$^{13}C$ NMR (75 MHz, $D_2O$) δ 167.2 ($1C_3$); 54.2 ($1C_4$); 49.5 ($1C_2$); 37.8 (1C1).

HRMS (ESI): m/z calculated for $C_4H_{11}N_2O_2$ $[M+H]^+$: 119.0815; observed 119.0815.

Step 3: Methyl 2,3-bis(2,6-bis(((tert-butyldimethylsilyl)oxy)-methyl)isonicotinamido)propanoate (9)

(9)

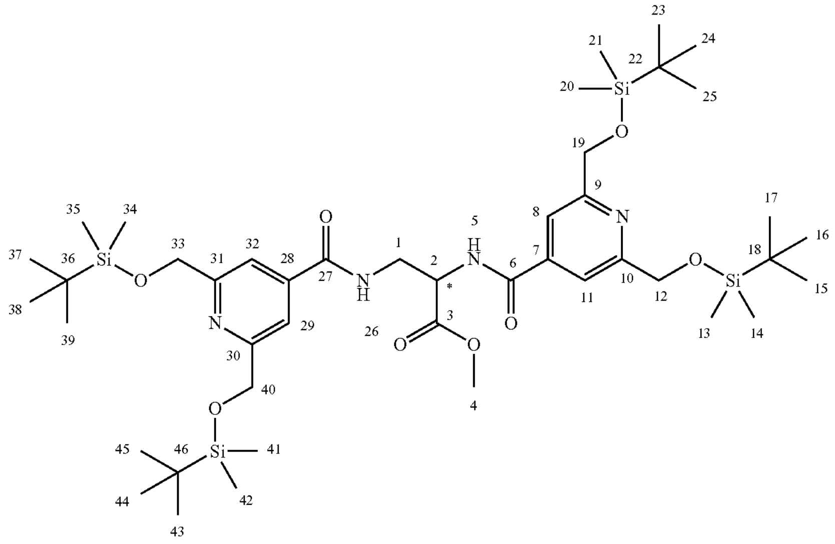

Methyl 2,3-diaminopropanoate hydrochloride (8) (99.7 mg; 0.645 mmol; 1.0 eq) was dissolved in anhydrous DMF (2.4 mL) and anhydrous DIPEA (381.7 μL; 2.19 mmol; 3.4 eq) was added. The reaction medium was stirred under argon at RT for 2 h20. Then the mixture 2,6-bis(((tert-butyldimethylsilyl)oxy)methyl) isonicotinic acid (4) (434.5 mg; 1.06 mmol; 1.6 eq) previously activated with HATU (603.4 mg; 1.59 mmol; 2.5 eq) and 2,6-lutidine (184.4 μL; 1.59 mmol; 2.5 eq) in anhydrous DMF (4.8 mL) with stirring and under argon at RT for 2 h 20, was added to the reaction medium. The reaction medium was stirred under argon at RT for 20 h. The DMF was evaporated under reduced pressure. Then the product was purified by flash chromatography ($SiO_2$, cyclohexane/acetone, 80:20) to give (9) (116.8 mg; 20%) in the form of a colorless oil.

$^1H$ NMR (300 MHz, DMSO) δ 9.13 (d; 3=7.3 Hz; $1H_5$); 8.96 (t; 3=5.7 Hz; $1H_{26}$); 7.67 (s; $2H_{8,11,29,32}$); 7.59 (s; $2H_{8,11,29,32}$); 4.75 (s; $4H_{12,19,33,40}$); 4.74 (s; $4H_{12,19,33,40}$); 4.73-4.66 (m; $1H_2$); 3.85-3.69 (m; $2H_1$); 3.64 (s; $3H_4$); 0.87 (s; $36H_{15-17,23-25,37-39,43-45}$); 0.06 (s; $24H_{13,14,20,21,34,35,41,42}$).

$^{13}C$ NMR (75 MHz, DMSO) δ 175.8 ($1C_3$); 171.8 ($1C_{6,27}$); 171.0 ($1C_{6,27}$); 166.1 ($2C_{9,10,30,31}$); 166.0 ($2C_{9,10,30,31}$); 148.6 ($1C_{7,28}$); 147.9 (1C7,28); 121.6 ($2C_{8,11,29,32}$); 121.4 ($2C_{8,11,29,32}$); 71.0 ($4C_{12,19,33,40}$); 58.1 ($1C_2$); 57.5 ($1C_4$); 39.7 under DMSO (1C1); 31.2 ($12C_{15-17,23-25,37-39,43-45}$); 23.4 ($4C_1$8,22,36,46); 0.0 ($8C_{13,14,20,21,34,35,41,42}$).

HRMS (ESI): m/z calculated for $C_{44}H_{11}N_4O_8Si_4[M+H]^+$: 905.5125; observed 905.5123.

Step 4: methyl 2,3-bis(2,6-bis(hydroxymethyl)isonicotinamido)propanoate (10)

(10)

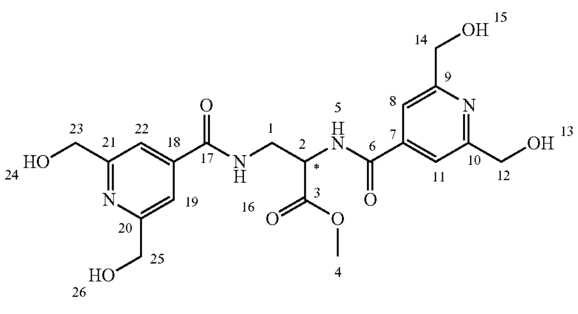

Methyl 2,3-bis(2,6-bis(((tert-butyldimethylsilyl)oxy) methyl)isonicotinamido)propanoate (9) (26.5 mg; 0.029 mmol; 1.0 eq) was dissolved in the THF (310 μL) and a solution of 1 M TBAF in THF (164 μL; 0.164 mmol; 5.6 eq) was added. The reaction medium was stirred under argon at RT (23° C.) for 5 h30. The THF was evaporated under reduced pressure. The crude was dissolved in a mixture of MeCN (1 mL), water (0.1 mL), DMF (0.1 mL) and DMSO (0.1 mL) and purified by semi-preparative high-pressure liquid chromatography ($t_R$=7.1 min; on the Gilson PLC 2050 system [ARMEN V2 (pump), ECOM TOYDAD600 (UV detector), SEDEX FP SAGA (DEDL detector)] UV detection at 254 nm at 25° C. and DEDL at 60° C.; Waters XBridge™ C-18 column; 5 μm (250 mm×19.00 mm); elution carried out with 0.1% trifluoroacetic acid (by volume) in water (solvent A), and acetonitrile (solvent B); gradient 5 to 60% B over 40 min then from 60 to 100% B over 5 min then 100% B over 5 min at 17.1 mL/min) to give (10) (10.7 mg; 80%) in the form of a white solid.

$^1$H NMR (300 MHz, $CD_3OD$) δ 7.90 (s; $2H_{8,11,19,22}$); 7.86 (s; $2H_{8,11,19,22}$); 5.00-4.91 (m; $1H_2$); 4.81 (s; $4H_{12,14,23,25}$); 4.79 (s; $4H_{12,14,23,25}$); 4.09-3.85 (m; 2H1); 3.80 (s; $3H_4$).

$^{13}$C NMR (75 MHz, $CD_3OD$) δ 171.57 ($1C_3$); 168.78 ($1C_{6,17}$); 167.89 (1C6,17); 162.27 ($2C_{9,10,20,21}$); 162.23 ($1C_{9,10,20,21}$); 145.99 ($1C_{7,18}$); 145.65 ($1C_{7,18}$); 118.63 ($2C_{8,11,19,22}$); 118.53 ($2C_{8,11,19,22}$); 64.55 ($2C_{12,14,23,25}$); 64.53 ($2C_{12,14,23,25}$); 54.68 ($1C_2$); 53.20 ($1C_4$); 41.90 ($1C_1$).

HRMS (ESI): neutral mass calculated for $C_{20}H_{24}N_4O_8$ [M]: 448.1594; observed 448.1589.

Step 5: methyl 2,3-bis(2,6-bis(bromomethyl) isonicotinamido) propanoate (11)

(11)

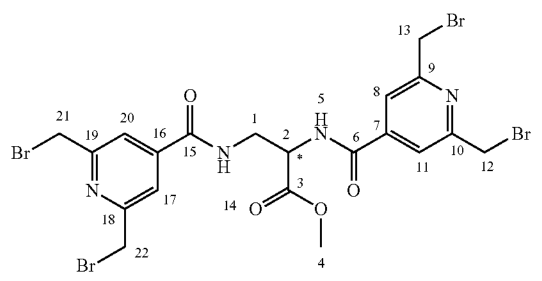

Methyl 2,3-bis(2,6-bis(hydroxymethyl)isonicotinamido) propanoate (10) (5.8 mg; 0.013 mmol; 1.0 eq) was dissolved in anhydrous MeCN (500 μL) then $PBr_3$ (12.1 μL; 0.13 mmol; 10.0 eq) was added slowly. The reaction medium was stirred at 45° C. for 2 h 15. The solution was cooled to 0° C., neutralized with water (1 mL) and extracted with AcOEt (3×5 mL). The combined organic phases were washed with a saturated NaCl solution, dried on $MgSO_4$ and concentrated under reduced pressure. The product (11) (7.1 mg; 79%) was obtained in the form of a white solid.

$^1$H NMR (300 MHz, $CD_3OD$) δ 7.82 (s; $2H_{8,11,17,20}$); 7.78 (s; $2H_{8,11,17,20}$); 4.93 (dd; J=7.7; 5.0 Hz; $1H_2$); 4.65 (s; $4H_{12,13,21,22}$); 4.63 (s; $4H_{2,13,21,22}$); 3.99 (dd; J=13.9; 5.0 Hz; 1H1); 3.90 (dd; J=13.9; 7.7 Hz; 1H1); 3.80 (s; $3H_4$). $^{13}$C NMR (75 MHz, $CD_3OD$) δ 171.54 ($1C_3$); 168.12 ($1C_{6,15}$); 167.25 ($1C_{6,15}$); 159.55 ($2C_{9,10,18,19}$); 159.52 ($2C_{9,10,18,19}$); 145.57 ($1C_{7,16}$); 145.19 ($1C_{7,16}$); 121.98 ($2C_{8,11,17,20}$); 121.87 ($2C_{8,11,17,20}$); 54.57 ($1C_2$); 53.22 ($1C_4$); 41.89 ($1C_1$); 33.27 ($2C_{12,13,21,22}$); 33.26 ($2C_{12,13,21,22}$).

HRMS (ESI): neutral mass calculated for $C_{20}H_{20}Br_4N_4O_4$[M]: 695.8218; observed 695.8194.

Example 2: Trastuzumab—Compound (11) Conjugate Reagents

Bioconjugation buffer 1, 5 mg/mL trastuzumab in bioconjugation buffer, reducing agent 1 (8.0 eq), compound (11) (12.0 eq) at a concentration of 1 mM in a mixture of 20% DMF and 80% MeOH.

Method

Bioconjugation reaction 1.

Denaturing HRMS analysis according to method 1

The results are shown in Table 1 below.

TABLE 1

| | LHHL | | | LH | | |
|---|---|---|---|---|---|---|
| | Intensity (%) | MM (Da)[1] | mass deviation from expected (Da) | Intensity (%) | MM (Da)[1] | mass deviation from expected (Da) |
| MAR 0 | | n.o.[2] | | | n.o.[2] | |
| MAR 1 | | n.o.[2] | | 100 | 72956 | −9 |
| MAR 2 | 100 | 145916 | −15 | | n.o.[2] | |
| MAR 3 | | n.o.[2] | | | n.o.[2] | |
| Average MAR | | 2.00 | | | 1.00 | |

[1]molecular mass of the deglycosylated species
[2]not observed

HRMS analysis allowed determining an average MAR of 2.00 for LHHL species and an average MAR of 1.00 for LH species. LHH, HH, H and L species were not observed.

SDS-PAGE Gel Analysis Under Denaturing Non-Reducing and Reducing Conditions

The results are shown in Table 2 below.

TABLE 2

| | | Species | | | | | |
|---|---|---|---|---|---|---|---|
| | DTT | LHHL | LHH | HH | LH | H | L |
| Optical density | — | 54 | n.o.[1] | n.o.[1] | 46 | n.o.[1] | n.o.[1] |
| (%) | + | 55 | n.o.[1] | n.o.[1] | 45 | n.o.[1] | n.o.[1] |

[1]not observed

Analysis on SDS-PAGE gel allowed determining under reducing conditions a reconstruction of 55% and under non-reducing conditions an average MAR of 2.00.

Example 3: methyl 3-(2,6-bis(bromomethyl)isonicotinamido)-2-((2,6-bis(bromomethyl)isonicotinamido) methyl)propanoate (16) and 3-(2,6-bis(bromomethyl)isonicotinamido)-2-((2,6-bis(bromomethyl)-isonicotinamido)methyl)propanoic acid (17)

General reaction scheme

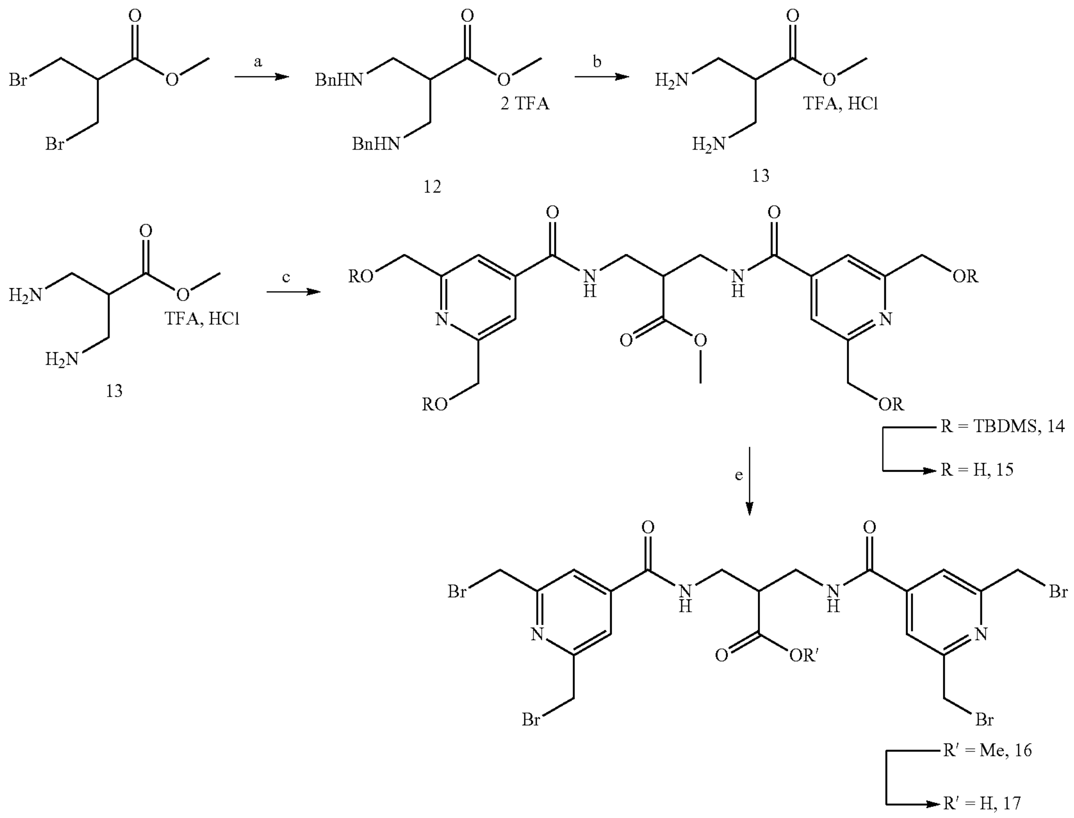

a $BnNH_2$, DIPEA, $CHCl_3$, 16 h 25, 0° C. then RT;
b $H_2$, $Pd(OH)_2/C$, 1,1,2-trichloroethane, MeOH, 62 h, RT;
c HATU, 2,6-lutidine, DMF, compound 4, 5 h, RT;
d TBAF, THF, 7 h 30, RT;
e $PBr_3$, MeCN, 2 h 30, 45° C.;
f LiOH, THF, $H_2O$, 2 h 10, RT.

Step 1: methyl 3-(benzylamino)-2-((benzylamino) methyl)propanoate (12), double salt of TFA (12)

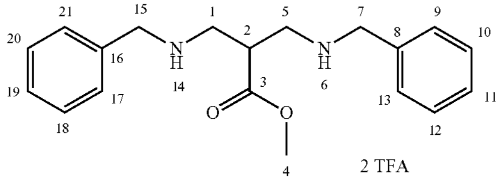

Methyl 3-bromo-2-(bromomethyl)propanoate (549 μL; 3.85 mmol; 1.0 eq) was dissolved in anhydrous $CHCl_3$ (9.6 mL). Then benzylamine (1.68 mL; 15.4 mmol; 4.0 eq) was added dropwise with stirring at 0° C. A precipitate was observed. The reaction medium was stirred under argon at 0° C. for 25 min. Then anhydrous DIPEA (1.41 mL; 8.1 mmol; 2.1 eq) was added dropwise to the reaction medium, the disappearance of the precipitate was observed. The reaction medium was stirred under argon at RT for 16 h. The $CHCl_3$ was evaporated under reduced pressure. The residue was taken up in AcOEt (15 mL), then washing was carried out with water (5×15 mL) and saturated NaCl solution (1×20 mL). The organic phase was then dried on $MgSO_4$ and concentrated under reduced pressure. The product was then salified into the hydrochloride: it was dissolved in MeOH (38 mL), then a solution of 1.25 M HCl in EtOH (9.23 mL; 11.5 mmol, 3.0 eq) was added with stirring at 0° C. The MeOH was evaporated under reduced pressure. The crude was dissolved in a mixture of MeOH (9 mL) and DMF (100 μL) and purified by semi-preparative high-pressure liquid chromatography ($t_R$=14.5 min; on the Gilson PLC 2050 system [ARMEN V2 (pump), ECOM TOYDAD600 (UV detector), UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 5 to 60% of B over 40 min then from 60 to 100% of B over 5 min then 100% of B over 5 min at 17.1 mL/min) to give (12) (875 mg; 42%) in the form of a colorless oil.

$^1H$ NMR (300 MHz, $CDCl_3$) δ 7.39 (s; $10H_{9-13,17-21}$); 4.13 (d; J=13.1 Hz; $2H_{7,15}$); 4.07 (d; J=13.0 Hz; $2H_{7,15}$); 3.64 (s; $3H_4$); 3.63-3.57 (m; $1H_2$); 3.41-3.22 (m; $4H_{1,5}$)

$^{13}C$ NMR (75 MHz, $CDCl_3$) δ 170.4 ($1C_3$); 130.1 ($4C_{9,10,12,13,17,18,20,21}$); 130.1 ($2C_{11,19}$); 129.6 ($2C_{8,16}$); 129.5 ($4C_{9,10,12,13,17,18,20,21}$); 53.5 ($1C_4$); 52.5 ($2C_{7,15}$); 45.7 ($2C_{1,5}$); 40.0 ($1C_2$).

$^{19}F$ NMR (282 MHz, $CDCl_3$) δ −75.75 (s, TFA).

HRMS (ESI): neutral mass calculated for $C_{19}H_{24}N_2O_2$ [M]: 312.1838; observed 312.1834.

Step 2: methyl 3-amino-2-(aminomethyl) propanoate, double salt of TFA (0.6) and HCl (1.4) (13)

(13)

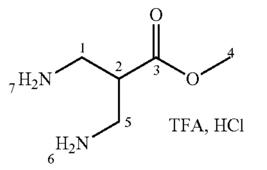

Methyl 3-(benzylamino)-2-((benzylamino)methyl) propanoate (12) (814.5 mg; 1.51 mmol; 1.0 eq) was dissolved in MeOH (16 mL). 1,1,2-trichloroethane (393 μL; 4.23 mmol, 2.8 eq) was added and the solution was degassed with argon for 15 min. Then $Pd(OH)_2/C$ at 20% by mass (327.2 mg, 40% m/m) was added. The reaction medium was stirred under a hydrogen atmosphere at RT for 62 h. The $Pd(OH)_2/C$ was filtered through Dicalite™ then the filtrate was concentrated under reduced pressure. The salified product (13) (376.1 mg, 99%) (1.4 HCl; 0.6 TFA, NMR assay) was obtained in the form of a brown heterogeneous oil.

$^1H$ NMR (300 MHz, $D_2O$) δ 3.72 (s; $3H_4$); 3.35-3.09 (m; $5H_{1,2,5}$).

$^1H$ NMR (300 MHz, DMSO) δ 8.16 (s; $6H_{6,7}$); 3.71 (s; $3H_4$); 3.16 (s; $1H_2$); 3.14 (s; $4H_{1,5}$).

$^{19}F$ NMR (282 MHz, $D_2O$) δ −75.68 (s; TFA).

$^{13}C$ NMR (75 MHz, $D_2O$) δ 171.64 ($1C_3$); 53.46 ($1C_4$); 40.25 ($1C_2$); 38.09 (2C1,5).

HRMS (ESI): m/z calculated for $C_5H_{13}N_2O_2$ $[M+H]^+$: 133.0972; observed 133.0973.

Step 3: 3-(2,6-bis(((tert-butyldimethylsilyl)oxy) methyl)isonicotinamido)-2-((2,6-bis(((tert-butyldimethylsilyl)oxy)methyl)isonicotinamido)methyl)-methyl propanoate (14)

(14)

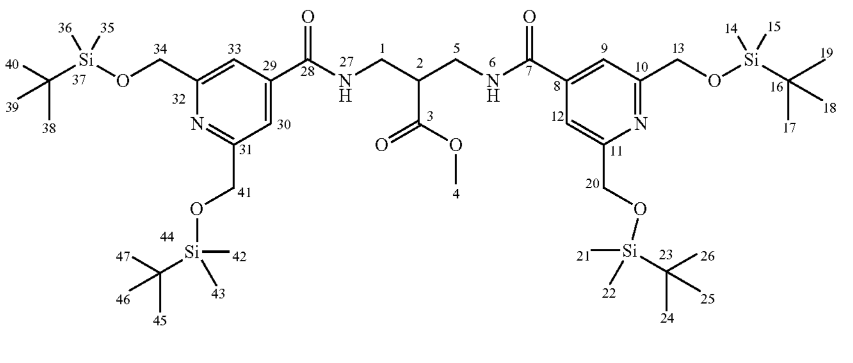

2,6-Bis(((tert-butyldimethylsilyl)oxy)methyl)isonicotinic acid (4) (291.1 mg; 0.707 mmol; 2.5 eq) was activated with HATU (323.6 mg; 0.851 mmol; 3.0 eq) and 2,6-lutidine (231 μL; 1.98 mmol; 7.0 eq) in anhydrous DMF (2.7 mL) with stirring and under argon at RT (24° C.) for 1 h15. Then salified methyl 3-amino-2-(aminomethyl) propanoate (0.6 TFA; 1.4 HCl) (71 mg, 0.282 mmol, 1.0 eq) dissolved in anhydrous DMF (0.8 mL) was added to the reaction medium. The reaction medium was stirred under argon at RT for 3 h 45. The DMF was evaporated under reduced pressure. Then the product was purified by flash chromatography ($SiO_2$, cyclohexane/AcOEt, 70:30) to give (14) (112.9 mg; 44%) in the form of a colorless lacquer.

$^1H$ NMR (300 MHz, DMSO) δ 8.89 (t; J=5.8 Hz, $2H_{6,27}$); 7.61 (s; $4H_{9,12,30,33}$); 4.76 (s; $8H_{13,20,34,41}$); 3.58 (s; $3H_4$); 3.55-3.42 (m; $4H_{1,5}$); 3.03 (p; 3=7.6 Hz; $1H_2$); 0.91 (s; $36H_{17\text{-}19,24\text{-}26,38\text{-}40,45\text{-}47}$); 0.09 (s; $24H_{14,15,21,22,35,36,42,43}$)

$^{13}C$ NMR (75 MHz, DMSO) δ 172.5 ($1C_3$); 165.8 (2C7, 28); 160.6 ($4C_{10,11,31,32}$); 143.3 ($2C_{8,29}$); 116.0 ($4C_{9,12,30,33}$); 65.5 ($4C_{13,20,34,41}$); 51.6 ($1C_4$); 44.7 ($1C_2$); 38.7 under DMSO ($2C_{1,5}$); 25.8 ($12C_{17\text{-}19,24\text{-}26,38\text{-}40,45\text{-}47}$); 18.0 ($4C_{16,23,37,44}$); −5.4 ($8C_{14,15,21,22,36,35,42,43}$).

HRMS (ESI): neutral ground calculated for $C_{45}H_{82}N_4O_8Si_4$ [M]: 919.5282; observed 919.5288.

Step 4: Methyl 3-(2,6-bis(hydroxymethyl)isonicotinamido)-2-((2,6-bis(hydroxymethyl)isonicotinamido)methyl)propanoate (15)

(15)

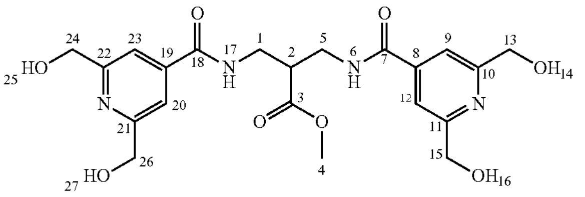

Methyl 3-(2,6-bis(((tert-butyldimethylsilyl)oxy)methyl) isonicotinamido)-2-((2,6-bis(((tert-butyldimethylsilyl)oxy) methyl)isonicotinamido)methyl)propanoate (14) (260.9 mg; 0.284 mmol; 1.0 eq) was dissolved in THF (2.0 mL) and a solution of 1 M TBAF in THF (1.30 mL; 1.31 mmol; 4.6 eq) was added. The reaction medium was stirred under argon at RT (25° C.) for 7 h 30. The THF was evaporated under reduced pressure. The crude was dissolved in MeOH (4 mL) and purified by semi-preparative high-pressure liquid chromatography ($t_R$=9.1 min; on the Gilson PLC 2050 system

[ARMEN V2 (pump), ECOM TOYDAD600 (UV detector), SEDEX FP SAGA (DEDL detector)] UV detection at 254 nm at 25° C. and DEDL at 60° C.; Waters XBridge™ C-18 column; 5 μm (250 mm×19.00 mm); elution carried out with 0.1% of TFA (by volume) in water (solvent A), and MeCN (solvent B); gradient 5 to 60% of B over 40 min then from 60 to 100% of B over 5 min then 100% of B over 5 min at 17.1 mL/min) to give (15) (95.1 mg; 72%) in the form of a white solid.

$^1$H NMR (300 MHz, DMSO) δ 9.00 (t; J=5.7 Hz; $2H_{5,7}$); 7.77 (s; $4H_{9,12,20,23}$); 4.62 (s; $8H_{13,15,24,26}$); 3.60 (s; $3H_4$); 3.58-3.43 (m; $4H_{1,5}$); 3.06 (p; J=6.6 Hz; $1H_2$).

$^{13}$C NMR (75 MHz, DMSO) δ 172.6 ($1C_3$); 165.3 ($2C_{7,18}$); 161.4 ($4C_{10,11,21,22}$); 143.3 ($2C_{8,19}$); 116.4 ($4C_{9,12,23,20}$); 63.5 ($4C_{13,15,24,26}$); 51.8 ($1C_4$); 44.7 ($1C_2$); 39.2 under DMSO ($2C_{1,5}$).

HRMS (ESI): m/z calculated for $C_{21}H_{27}N_4O_8[M+H]^+$: 463.1823; observed 463.1819.

Step 5: Methyl 3-(2,6-bis(bromomethyl)isonicotinamido)-2-((2,6-bis(bromomethyl)-isonicotinamido)methyl)propanoate (16)

(16)

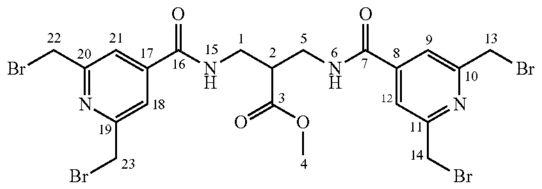

Methyl 3-(2,6-bis(hydroxymethyl)isonicotinamido)-2-((2,6-bis(hydroxymethyl)-isonicotinamido)-methyl)propanoate (15) (86.3 mg; 0.187 mmol; 1.0 eq) was suspended in anhydrous MeCN (4.3 mL) then $PBr_3$ (105 μL; 1.12 mmol; 6.0 eq) was added dropwise. The reaction medium was stirred at 45° C. for 2 h 30. The solution was cooled to 0° C., neutralized with water (6 mL) and extracted with AcOEt (3×20 mL). The combined organic phases were washed with a saturated NaCl solution, dried on $MgSO_4$ and concentrated under reduced pressure. The crude was dissolved in a mixture of MeOH (2.9 mL) and DMF (1.2 mL) and purified by semi-preparative high-pressure liquid chromatography ($t_R$=30.26 min; on the Gilson PLC 2050 system [ARMEN V2 (pump), ECOM TOYDAD600 (UV detector)] UV detection at 254 nm at 25° C.; Waters XBridge™ C-18 column; 5 μm (250 mm×19.00 mm); elution carried out with 0.1% of TFA (by volume) in water (solvent A), and MeCN (solvent B); gradient 30 to 80% of B over 49 min then from 80 to 100% of B over 2 min then 100% of B over 3 min at 17.1 mL/min) to give the product (16) (64.7 mg; 49%) in the form of a slightly bluish solid.

$^1$H NMR (300 MHz, $CD_3OD$) δ 8.93 (t; J=5.8 Hz; $2H_{6,15}$); 7.81 (s; $4H_{9,12,18,21}$); 4.65 (s; $8H_{13,14,22,23}$); 3.74 (s; $3H_4$); 3.73-3.67 (m; $4H_{1,5}$); 3.13 (p; J=6.7 Hz; $1H_2$).

$^{13}$C NMR (75 MHz, $CD_3OD$) δ 159.5 ($4Cu_{1,10,19,20}$); 145.7 (2C8,7); 121.8 ($4C_{9,12,19,21}$); 52.8 ($1C_4$); 46.3 ($1C_2$); 40.3 ($2C_{1,5}$); 33.2 ($4C_{13,14,22,23}$); $C_3$, $C_7$ and $C_{16}$ not observed.

HRMS (ESI): neutral mass calculated for $C_{21}H_{22}N_4O_4Br_4$ [M]: 709.8374; observed 709.8349.

Step 6: 3-(2,6-bis(bromomethyl)isonicotinamido)-2-((2,6-bis(bromomethyl)isonicotinamido)methyl) propanoic acid (17)

(17)

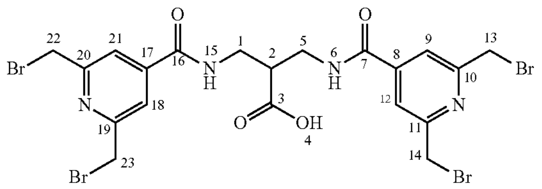

Methyl 3-(2,6-bis(bromomethyl)isonicotinamido)-2-((2,6-bis(bromomethyl)-isonicotinamido)-methyl)propanoate (16) (56.8 mg; 0.080 mmol; 1.0 eq) was dissolved in THF (4.4 mL) and a solution of hydrated LiOH (4.8 mg; 0.199 mmol; 2.5 eq) in water (1.99 mL) was added slowly. The reaction medium was stirred at AT (25° C.) for 2 h 10. The reaction medium was acidified at 0° C. with an aqueous solution of 0.1 N HCl then extracted with AcOEt (4×10 mL). The combined organic phases were washed with a saturated NaCl solution, dried on $MgSO_4$ and concentrated under reduced pressure. The crude was dissolved in a mixture of MeOH (1.7 mL) and DMF (0.7 mL) and purified by semi-preparative high-pressure liquid chromatography ($t_R$=31.13 min; on the Gilson PLC 2050 system [ARMEN V2 (pump), ECOM TOYDAD600 (UV detector)] UV detection at 254 nm at 25° C.; Waters XBridge™ C-18 column; 5 μm (250 mm×19.00 mm); elution carried out with 0.1% of TFA (by volume) in water (solvent A), and MeCN (solvent B); gradient 20 to 60% of B over 33 min then from 60 to 100% of B over 2 min then 100% of B over 2 min at 17.1 mL/min) to give the product (17) (33.6 mg; 60%) was obtained in the form of a white lyophilisate.

$^1$H NMR (300 MHz, $CD_3OD$) δ 8.96 (t; J=5.7 Hz; $2H_{6,15}$); 7.83 (s; $4H_{9,12,15,21}$); 4.65 (s; $8H_{13,14,22,23}$); 3.82-3.61 (m; $4H_{1,5}$); 3.18-3.04 (m; $1H_2$).

$^{13}$C NMR (75 MHz, $CD_3OD$) δ 175.6 ($1C_3$); 167.5 ($1C_{7,16}$); 159.5 ($4C_{11,10,19,20}$); 145.7 ($2C_{8,17}$); 121.9 ($4C_{9,12,18,21}$); 46.1 ($1C_2$); 40.4 (2C1,5); 33.2 (4C13,14,22,23).

HRMS (ESI): neutral mass calculated for $C_{20}H_{20}N_4O_4Br_4$ [M]: 695.8290; observed 695.8218.

Example 4: Trastuzumab—Compound (16) Conjugate

Reagents

Bioconjugation buffer 1, 5 mg/mL trastuzumab in bioconjugation buffer, reducing agent 2 (8.0 eq), compound (16) (12.0 eq) at a concentration of 3 mM in a mixture of 20% DMF and 80% MeOH.

Method

Bioconjugation reaction 1. In this case, the reducing agent 2 was removed by purification on a membrane (10 kDa) before the addition of the compound (16).

Denaturing HRMS analysis according to method 1 The results are shown in Table 3 below.

TABLE 3

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 96 | 72979 |
| MAR 2 | 100 | 145958 | 4 | 73370 |
| MAR 3 | n.o.[2] | | n.o.[2] | |
| Average MAR | 2.00 | | 1.06 | |

[1]molecular mass of the deglycosylated species

[2]not observed

HRMS analysis allowed determining an average MAR of 2.00 for the LHHL species and an average MAR of 1.06 for the LH species. LHH, HH, H and L species were not observed.

SDS-PAGE Gel Analysis Under Denaturing Non-Reducing Conditions

The results are shown in Table 4 below.

TABLE 4

| | Species | | | | | |
|---|---|---|---|---|---|---|
| | LHHL | LHH | HH | LH | H | L |
| Optical density (%) | 75 | n.o.[1] | n.o.[1] | 25 | n.o.[1] | n.o.[1] |

[1]not observed

Analysis on SDS-PAGE gel allowed determining under non-reducing conditions an average MAR of 2.03.

Example 5: Nivolumab—Compound (16) Conjugate

Reagents

Bioconjugation buffer 1, 5 mg/mL nivolumab in bioconjugation buffer, reducing agent 2 (8.0 eq), compound (16) (6.0 eq) at a concentration of 1 mM in a mixture of 20% DMF and 80% MeOH.

Method

Bioconjugation reaction 1. In this case, the reducing agent 2 was removed by purification on a membrane (10 kDa) before the addition of the compound (16).

Denaturing HRMS Analysis According to Method 1

The results are shown in Table 5 below.

TABLE 5

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | n.o.[2] | | n.o.[2] | | 100 | 23337 |
| MAR 1 | 36 | 143735 | 99 | 72064 | n.o.[2] | |
| MAR 2 | 64 | 144132 | 1 | 72455 | n.o.[2] | |
| MAR 3 | n.o.[2] | | n.o.[2] | | n.o.[2] | |
| Average MAR | 1.64 | | 1.01 | | 0.00 | |

[1]molecular mass of the deglycosylated species
[2]not observed

HRMS analysis allowed determining an average MAR of 1.64 for the LHHL species and an average MAR of 1.01 for the LH species. LHH, HH and H species were not observed.

SDS-PAGE Gel Analysis Under Denaturing Non-Reducing and Reducing Conditions

The results are shown in Table 6 below.

TABLE 6

| | Species | | | | | | |
|---|---|---|---|---|---|---|---|
| | DTT | LHHL | LHH | HH | LH | H | L |
| Optical density | – | 70 | n.o.[1] | n.o.[1] | 30 | n.o.[1] | n.o.[1] |
| (%) | + | 79 | n.o.[1] | n.o.[1] | 21 | n.o.[1] | n.o.[1] |

[1]not observed

The analysis on SDS-PAGE gel allowed determining under reducing conditions a reconstruction of 79% and under non-reducing conditions an average MAR of 1.75.

Example 6: Trastuzumab—Compound (16) Conjugate

Reagents

Bioconjugation buffer 1, 10 mg/mL trastuzumab in bioconjugation buffer, reducing agent 1 (7.0 eq), compound (16) (10.6 eq) at a concentration of 3 mM in a mixture of 20% DMF and 80% MeOH.

Method

Bioconjugation reaction 2.

Denaturing HRMS Analysis According to Method 1

The results are shown in Table 7 below.

TABLE 7

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | n.o.[2] | | n.o.[2] | | 100 | 23439 |
| MAR 1 | 71 | 145564 | 100 | 72979 | n.o.[2] | |
| MAR 2 | 29 | 145957 | n.o.[2] | | n.o.[2] | |
| MAR 3 | n.o.[2] | | n.o.[2] | | n.o.[2] | |
| Average MAR | 1.29 | | 1.00 | | 0.00 | |

[1]molecular mass of the deglycosylated species

[2]not observed

HRMS analysis allowed determining an average MAR of 1.29 for LHHL species and an average MAR of 1.00 for LH species. LHH, HH and H species were not observed.

SDS-PAGE Gel Analysis Under Denaturing Non-Reducing and Reducing Conditions

The results are shown in Table 8 below.

TABLE 8

| | Species | | | | | | |
|---|---|---|---|---|---|---|---|
| | DTT | LHHL | LHH | HH | LH | H | L |
| Optical density | – | 100 | n.o.[1] | n.o.[1] | n.o.[1] | n.o.[1] | n.o.[1] |
| (%) | + | 100 | n.o.[1] | n.o.[1] | n.o.[1] | n.o.[1] | n.o.[1] |

[1]not observed

Analysis on SDS-PAGE gel allowed determining under reducing conditions a reconstruction of 100% and under non-reducing conditions an average MAR of 1.29.

Example 7: Trastuzumab—Compound (17) Conjugate

Reagents

Bioconjugation buffer 1, 5 mg/mL trastuzumab in bioconjugation buffer, reducing agent 1 (8.0 eq), compound (17) (12.0 eq) at a concentration of 3 mM in a mixture of 20% DMF and 80% MeOH.

Method Bioconjugation reaction 1.

Denaturing HRMS Analysis According to Method 1

The results are shown in Table 9 below.

TABLE 9

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 96 | 72967 |
| MAR 2 | 75 | 145934 | 4 | 73344 |
| MAR 3 | 25 | 146315 | n.o.[2] | |
| Average MAR | 2.25 | | 1.04 | |

[1]molecular mass of the deglycosylated species

[2]not observed

HRMS analysis allowed determining an average MAR of 2.25 for the LHHL species and an average MAR of 1.04 for the LH species. LHH, HH, H and L species were not observed.

SDS-PAGE Gel Analysis Under Denaturing Non-Reducing and Reducing Conditions

The results are shown in Table 10 below.

TABLE 10

| | Species | | | | | | |
|---|---|---|---|---|---|---|---|
| | DTT | LHHL | LHH | HH | LH | H | L |
| Optical density | – | 48 | n.o.[1] | n.o.[1] | 52 | n.o.[1] | n.o.[1] |
| (%) | + | 54 | n.o.[1] | n.o.[1] | 46 | n.o.[1] | n.o.[1] |

[1]not observed

Analysis on SDS-PAGE gel allowed determining under reducing conditions a reconstruction of 54% and under non-reducing conditions an average MAR of 2.16.

Example 8: N-(2-((((2,6-bis(bromomethyl)pyridin-4-yl)carbonyl)amino)-methyl)-19-(11,12-didehydrodibenzo[b,f]azocin-5(6H)-yl)-3,14,19-trioxo-7,10-dioxa-4,13-diazanonadec-1-yl)-2,6-bis(bromomethyl)pyridine-4-carboxamide (20) and MMAE 6-azidohexanamido-N-hexanamide-valine-citrulline-p-aminobenzoyl carbamate (22)

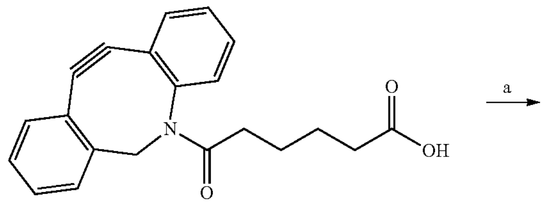

-continued
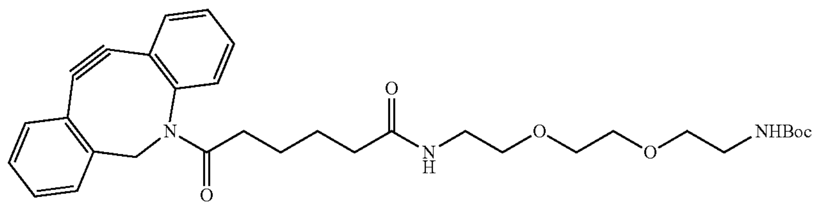
18
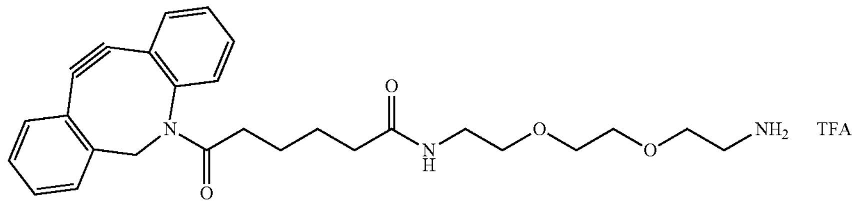
19
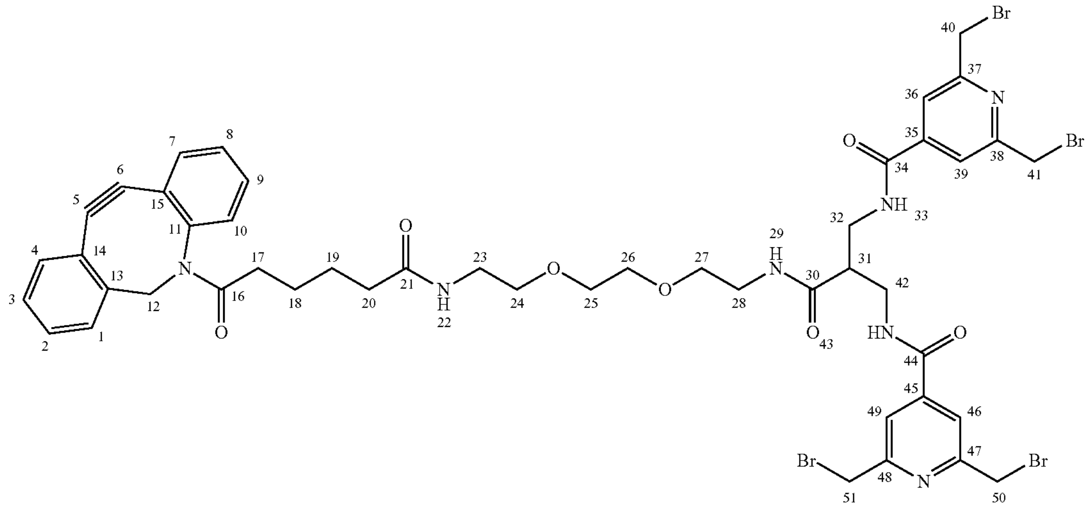
(20)
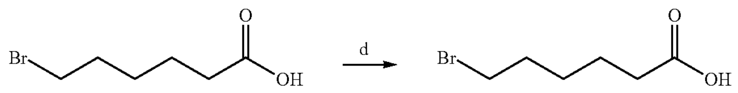
21

-continued

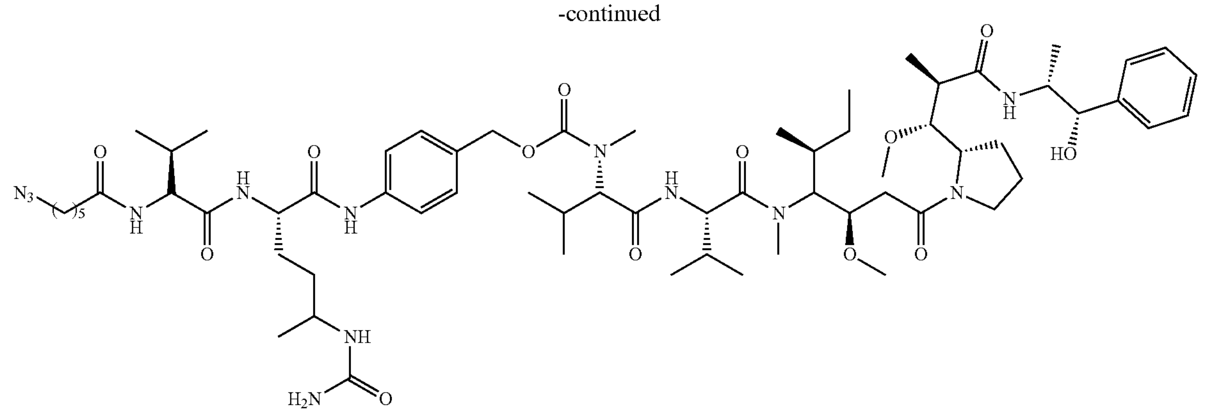

22

(a) $NH_2$-PEG$_2$-$(CH_2)_2NH_2$, HATU, 2,6-lutidine, DMF, 1 h 40, RT; (b) TFA, DCM, 2 h 20, RT; (c) compound (17), EEDQ, DIPEA, DMF, MeCN, 2 h, 25° C.; (d) $NaN_3$, DMF, 16 h, 100° C.; (e) TFA•$NH_2$-val-cit-PABC-MMAE, HATU, 2,6-lutidine, DMF, 15 h, 0° C. to RT.

Step 1: tert-butyl (2-(2-(2-((6-(11,12-didehydrodibenzo[b,f]azocin-5(6H)-yl)-6-oxohexanoyl)amino)ethoxy)ethoxy)ethyl)carbamate (18)

(18)

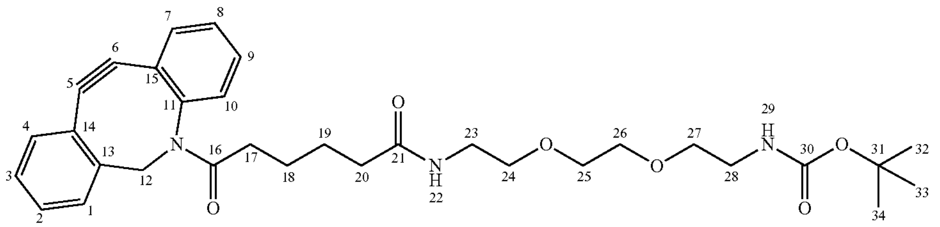

6-(11,12-didehydrodibenzo[b,f]azocin-5(6H)-yl)-6-oxohexanoic acid (32.1 mg; 0.104 mmol; 1.2 eq) was suspended in anhydrous DMF (750 μL). Then HATU (66.6 mg; 0.175 mmol; 2.0 eq) and 2,6-lutidine (26.2 μL; 0.225 mmol; 2.6 eq) were added. The activation solution was stirred under argon at RT (19° C.) for 10 min. Then tert-butyl (2-(2-(2-aminoethoxy)ethoxy)ethyl)carbamate (20.6 μL; 0.087 mmol; 1.0 eq) was added to the activation medium slowly. The reaction medium obtained was stirred under argon at RT for 1 h30. The DMF was evaporated under reduced pressure. Then the product was purified by flash chromatography ($SiO_2$, DCM/MeOH, 95:5) to give (18) (55.6 mg; 100% conversion, $P_{NMR}$: 81%) in the form of a yellow oil.

$^1$H NMR (300 MHz, $CD_3OD$) δ 7.67-7.61 (m; $1H_{ar}$); 7.51-7.42 (m; $4H_{ar}$); 7.39-7.27 (m; $2H_{ar}$); 7.26-7.21 (m; $1H_{ar}$); 5.12 (d; J=13.9 Hz; $1H_{12}$); 3.68 (d; J=13.9 Hz; $1H_{12}$); 3.56 (s; $4H_{25,26}$); 3.51-3.43 (m; $4H_24$,27); 3.26 (t; J=4.7 Hz; $2H_{23}$); 3.19 (t; J=5.6 Hz; $2H_{28}$); 2.26-2.12 (m; $1H_{17,20}$); 2.01-1.88 (m; $3H_{17,20}$); 1.41 (s; $9H_{32-34}$); 1.36-1.19 (m; $4H_{18-19}$).

$^{13}$C NMR (75 MHz, $CD_3OD$) δ 175.8 ($1C_{21}$); 175.3 ($1C_{16}$); 153.0 ($1C_{11,13,14,15}$); 149.5 ($1C_{11,13,14,15}$); 133.5 ($1C_{ar}$); 130.4 ($1C_{ar}$); 129.9 ($1C_{ar}$); 129.7 ($1C_{30}$); 129.6 ($1C_{ar}$); 129.2 ($1C_{ar}$); 128.9 ($1C_{ar}$); 128.1 ($1C_{ar}$); 126.5 ($1C_{ar}$); 124.3 ($1C_{11,13,14,15}$); 123.7 ($1C_{11,13,14,15}$); 115.8 ($1C_{5-6}$); 108.9 ($1C_{5-6}$); 71.3 ($2C_{23-26}$); 71.1 ($1C_{31}$); 70.6 ($2C_{24-27}$); 56.6 ($1C_{12}$); 41.2 ($1C_{28}$); 40.3 ($1C_{23}$); 36.5 ($1C_{17-20}$); 35.6 ($1C_{17-20}$); 28.8 ($3C_{32-34}$); 26.2 ($1C_{18-19}$); 25.9 ($1C_{18-19}$).

HRMS (ESI): neutral mass calculated for $C_{32}H_{41}N_3O_6$ [M]: 563.2995; observed 563.5991.

Step 2: NV-(2-(2-(2-aminoethoxy)ethoxy)ethyl)-6-(11,12-didehydro-dibenzo[b,f]azocin-5(6H)-yl)-6-oxohexanamide, TFA salt (19)

(19)

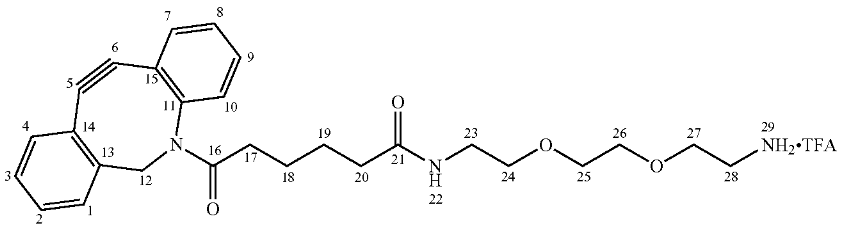

Tert-butyl (2-(2-(2-((6-(11,12-didehydrodibenzo[b,f]azocin-5(6H)-yl)-6-oxohexanoyl)-amino)ethoxy)ethoxy)ethyl) carbamate (52.2 mg; 0.093 mmol; 1.0 eq) was dissolved in DCM (930 μL). Then TFA (93.0 μL; 10% v/v) was added. The reaction medium obtained was stirred at RT for 2 h 20. The reaction medium was concentrated under reduced pressure and purified by semi-preparative high-pressure liquid chromatography ($t_R$=20.06 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% of TFA (by volume) in water (solvent A), and MeCN (solvent B); gradient 20 to 60% B over 33 min then 60 to 100% B over 2 min and 100% B over 2 min at 17.1 mL/min) to give (19) (21.3 mg; 40%) in the form of a slightly pink oil.

$^1$H NMR (300 MHz, $CD_3OD$) δ 7.69-7.63 (m; $1H_{ar}$); 7.54-7.43 (m; $4H_{ar}$); 7.41-7.30 (m; $2H_{ar}$); 7.28-7.23 (m; $1H_{ar}$); 5.13 (d; J=13.9 Hz; $1H_{12}$); 3.71 (d; J=13.9 Hz; $1H_{12}$); 3.68-3.62 (m; $2H_{27}$); 3.63-3.57 (m; $4H_{25,26}$); 3.49 (t; J=5.8 Hz; $3H_{24}$); 3.31-3.26 (m; $2H_{23}$); 3.08 (t; $2H_{28}$); 2.30-2.13 (m; $1H_{17,20}$); 1.98 (t; J=7.0 Hz; $2H_{17,20}$); 1.95-1.87 (m; $1H_{17,20}$); 1.45-1.20 (m; $4H_{18-19}$).

$^{13}$C NMR (75 MHz, $CD_3OD$) δ 175.9 ($1C_{21}$); 175.3 ($1C_{16}$); 152.9 ($1C_{11,13,14,15}$); 149.5 ($1C_{11,13,14,15}$); 133.5 ($1C_{ar}$); 130.4 ($1C_{ar}$); 130.0 ($1C_{ar}$); 129.7 ($1C_{ar}$); 129.2 ($1C_{ar}$); 128.9 ($1C_{ar}$); 128.1 ($1C_{ar}$); 126.5 ($1C_{ar}$); 124.4 (1C1,13,14,15); 123.7 (1C1,1,14,15); 115.7 ($1C_{5-6}$); 108.8 ($1C_{5-6}$); 71.4 ($1C_{25-26}$); 71.3 ($1C_{25-26}$); 70.6 ($1C_{24}$); 67.9 ($1C_{27}$); 56.6 ($1C_{12}$); 40.7 ($1C_{28}$); 40.1 ($1C_{23}$); 36.5 ($1C_{1-20}$); 35.6 ($1C_{17-20}$); 26.2 ($1C_{18-19}$); 25.9 ($1C_{18-19}$).

HRMS (ESI): neutral mass calculated for $C_{27}H_{33}N_3O_4$ [M]: 463.2471; observed 463.2466.

Step 3: N-(2-((((2,6-bis(bromomethyl)pyridin-4-yl) carbonyl)amino)methyl)-19-(11,12-didehydrodibenzo[b,f]azocin-5(6H)-yl)-3,14,19-trioxo-7,10-dioxa-4,13-diazanonadec-1-yl)-2,6-bis (bromomethyl)pyridine-4-carboxamide (20)

propanoic acid (17) (20.4 mg; 0.029 mmol; 1.7 eq) was suspended in anhydrous MeCN (1.98 mL) then EEDQ (56.1 mg; 0.23 mmol; 13.0 eq) was added. The activation medium was stirred under argon at 25° C. for 30 min. A solution of N-(2-(2-(2-aminoethoxy)ethoxy)ethyl)-6-(11,12-didehydrodibenzo[b,f]azocin-5(6H)-yl)-6-oxohexanamide trifluoroacetic acid salt (19) (10.1 mg; 0.018 mmol; 1.0 eq), solubilized in anhydrous DMF (1.68 mL) in the presence of DIPEA (12.18 μL; 0.070 mmol; 4.0 eq), was added to the activation medium. Then DIPEA (12.18 μL; 0.070 mmol; 4.0 eq) was added to the reaction medium. The reaction medium was stirred under argon in the dark and at 25° C. for 1 h40. The mixture was diluted with DMF (800 μL) and purified by semi-preparative high-pressure liquid chromatography ($t_R$=29.25 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% B over 37 min then 100% B over 6 min at 17.1 mL/min) to give (20) (17.2 mg; 86%) in the form of a white solid.

$^1$H NMR (300 MHz, $CD_3OD$) δ 8.88 (t; J=5.9 Hz; $2H_{33,43}$); 8.19 (t; J=5.8 Hz; $1H_{22,29}$); 7.82 (s; $4H_{36,39,46,49}$); 7.82 (s; $1H_{22,29}$); 7.67-7.60 (m; $1H_{ar\ DBCO}$); 7.54-7.40 (m; $4H_{ar\ DBCO}$); 7.38-7.26 (m; $2H_{ar\ DBCO}$); 7.26-7.20 (m; $1H_{ar\ DBCO}$); 5.12 (d; J=13.9 Hz; $1H_{12}$); 4.63 (s; $8H_{40,41,50,51}$); 3.68 (d; J=14.0 Hz; $1H_{12}$); 3.64-3.56 (m; $4H_{32,42}$); 3.55-3.44 (m; $6H_{24,25,26,27}$); 3.44-3.36 (m; $2H_{24,25,26,27}$); 3.32 under MeOH ($2H_{23}$); 3.23 (t; J=5.5 Hz; $2H_{28}$); 3.09-2.97 (m; $1H_{31}$); 2.26-2.13 (m; $1H_{1-20}$); 2.04-1.80 (m; $3H_{7-20}$); 1.45-1.15 (m; $4H_{18-19}$).

$^{13}$C NMR (75 MHz, $CD_3OD$) δ 167.2 ($2C_{34,44}$); 159.5 ($4C_{37,38,47,48}$); 145.7 ($2C_{35,45}$); 133.5 ($1C_{1,4,7-10}$); 130.4 ($1C_{1-4,7-10}$); 130.0 ($1C_{1-4,7-10}$); 129.6 ($1C_{1-4,7-10}$); 129.2 ($1C_{1-4,7-10}$); 128.9 ($1C_{1-4,7-10}$); 128.1 ($1C_{1-4,7-10}$); 126.5 ($1C_{1-4,7-10}$); 121.9 ($4C_{36,39,46,49}$); 71.3 ($1C_{23,24,25,26,27,28}$); 71.0 ($1C_{23,24,25,26,27,28}$); 70.6 ($1C_{23,24,25,26,27,28}$); 70.5 ($1C_{23,24,25,26,27,28}$); 56.6 ($1C_{12}$); 47.3 ($1C_{31}$); 41.2 ($2C_{32,42}$);

(20)

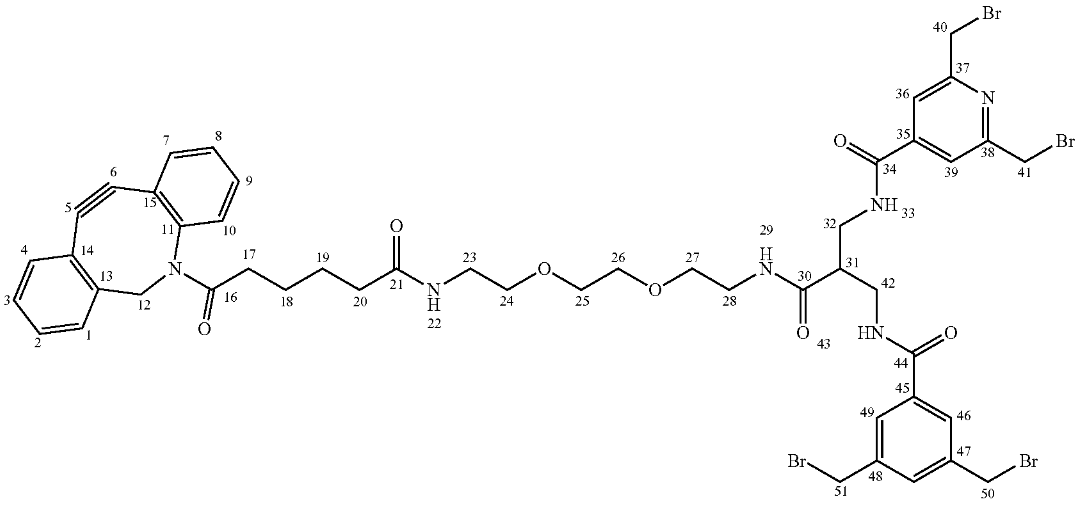

Under an inert atmosphere, in the dark and under anhydrous conditions, 3-(2,6-bis(bromomethyl)isonicotinamido)-2-((2,6-bis(bromomethyl)isonicotinamido)methyl)-

40.2 ($1C_{23,24,25,26,27,28}$); 40.1 ($1C_{23,24,25,26,27,28}$), 36.5 ($1C_{17-20}$); 35.6 ($1C_{17,20}$); 33.3 ($4C_{40,41,50,51}$); 26.2 ($1C_{18-19}$); 26.0 ($1C_{18-19}$).

HRMS (ESI): neutral mass calculated for $C_{47}H_{51}N_7O_7Br_4$ [M]: 1141.0583; observed 1141.0540.

Step 4: 6-azidohexanoic acid (21)

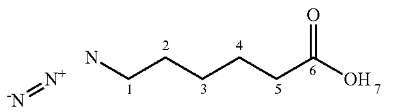
(21)

6-Bromohexanoic acid (100 mg; 0.513 mmol; 1.0 eq) was dissolved in peptide DMF (5 mL) and $NaN_3$ (167 mg; 2.56 mmol; 5.0 eq) was added. The reaction medium was stirred at 100° C. for 16 h. The DMF was evaporated under reduced pressure. The residue was taken up in DCM (20 mL), then washing was carried out with 1×20 mL of an aqueous solution of 0.1 M HCl then 1×20 mL of a saturated NaCl solution. The organic phase was then dried on $MgSO_4$ and concentrated under reduced pressure. The product (21) (81 mg, 100%) was obtained in the form of a white opaque oil.

$^1$H NMR (300 MHz, $CDCl_3$) δ 8.75 (s; $1H_7$); 3.28 (t; J=6.8 Hz; $2H_5$); 2.36 (t; J=7.3 Hz; $2H_1$); 1.76-1.55 (m; $4H_{2,4}$); 1.52-1.34 (m; $2H_3$).

$^{13}$C NMR (75 MHz, $CDCl_3$) b 179.1 ($1C_6$); 51.4 ($1C_1$); 34.1 ($1C_5$); 28.7 ($1C_2$); 26.3 ($1C_3$); 24.4 ($1C_4$).

HRMS (ESI): m/z calculated for $C_6H_{10}N_3O_2$ $[MH]^-$: 156.0779; observed 156.0779.

Step 5: MMAE 6-azidohexanamido-N-hexanamide-valine-citrulline-p-aminobenzoyl carbamate (22)

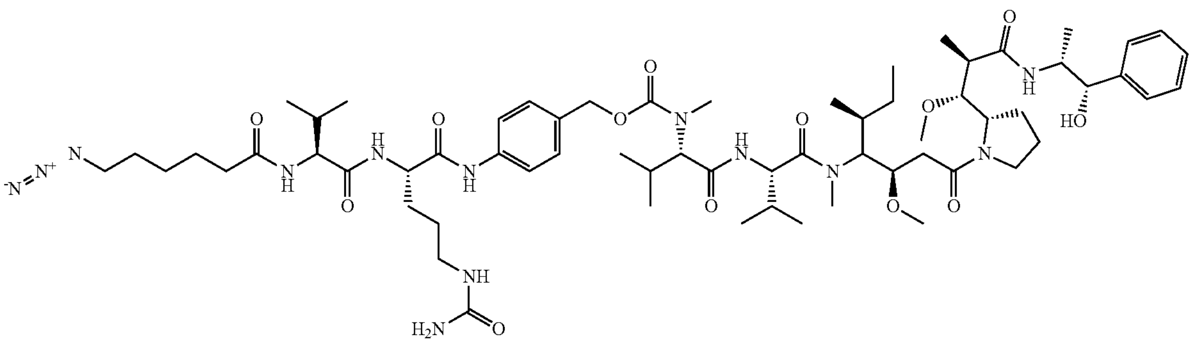
(22)

Azidohexanoic acid (21) (1.3 mg; 0.008 mmol; 2.0 eq) was dissolved in anhydrous DMF (100 μL). The solution was cooled to 0° C., then HATU (6.1 mg; 0.016 mmol; 4.0 eq) and 2,6-lutidine (2.8 μL; 0.024 mmol; 6.0 eq) were added. The activation solution was stirred under argon at 0° C. for 15 min. A solution of MMAE valine-citrulline-p-aminobenzoyl carbamate trifluoroacetic acid salt (5.0 mg; 0.004 mmol; 1.0 eq), solubilized in anhydrous DMF (100 μL), was added to the activation medium. The reaction medium obtained was stirred under argon at RT for 15 h. The mixture was diluted by 4 with anhydrous DMF and purified by semi-preparative high-pressure liquid chromatography ($t_R$=19.3 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% B over 32 min then 100% B over 6 min at 17.1 mL/min) to give (22) (3.8 mg; 75%) in the form of a white solid.

$^1$H NMR (300 MHz, DMSO) δ 9.99 (s; 1H); 8.31 (s; 1H); 8.09 (d; J=7.4 Hz; 2H); 7.87 (dd; J=16.9; 8.7 Hz; 2H); 7.61 (dd; J=15.3; 8.5 Hz; 3H); 7.40-7.21 (m; 7H); 7.22-7.10 (m; 1H); 5.97 (s; 1H); 5.41 (s; 2H); 5.16-4.90 (m; 2H); 4.73 (s; 1H); 4.54-4.31 (m; 3H); 4.30-4.13 (m; 2H); 4.13-3.87 (m; 2H); 3.78 (d; J=11.4 Hz; 1H); 3.29 (t; J=6.9 Hz; 1H); 3.23 (d; J=4.8 Hz; 2H); 3.20 (s; 1H); 3.17 (s; 1H); 3.11 (s; 1H); 2.97 (s; 2H); 2.86 (d; J=11.1 Hz; 2H); 2.27 (dd; 3=10.3; 8.5 Hz; 1H); 2.23-2.05 (m; 3H); 2.05-1.89 (m; 1H); 1.87-1.63 (m; 3H); 1.53 (dd; J=14.1; 6.8 Hz; 6H); 1.41-1.19 (m; 4H); 1.11-0.94 (m; 6H); 0.94-0.68 (m; 26H).

HRMS (ESI): neutral mass calculated for $C_{64}H_{103}N_{13}O_{13}$ [M]: 1261.7798; observed 1261.7758.

Example 9: Trastuzumab—Compound (20) Conjugate

Reagents

Bioconjugation buffer 1, 5 mg/mL trastuzumab in bioconjugation buffer, reducing agent 1 (7.0 eq), compound (20) (10.6 eq) at a concentration of 3 mM in a mixture of 20% DMF and 80% MeOH.

Method

Bioconjugation reaction 2.

The reaction mixture was purified on PD-10 (GE Healthcare) with PBS buffer Gibco® pH 7.4.

Denaturing HRMS Analysis According to Method 1

The results are shown in Table 11 below.

TABLE 11

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | 13 | 145996 | 100 | 73411 |
| MAR 2 | 87 | 146822 | n.o.[2] | |
| MAR 3 | n.o.[2] | | n.o.[2] | |
| Average MAR | 1.87 | | 1.00 | |

[1]molecular mass of the deglycosylated species
[2]not observed

HRMS analysis allowed determining an average MAR of 1.87 for LHHL species and an average MAR of 1.00 for LH species. LHH, HH, H and L species were not observed.

SDS-PAGE Gel Analysis Under Denaturing Non-Reducing and Reducing Conditions

The results are shown in Table 12 below.

TABLE 12

| | DTT | Species | | | | | |
|---|---|---|---|---|---|---|---|
| | | LHHL | LHH | HH | LH | H | L |
| Optical density | − | 92 | n.o.[1] | n.o.[1] | 8 | n.o.[1] | n.o.[1] |
| (%) | + | 96 | n.o.[1] | n.o.[1] | 4 | n.o.[1] | n.o.[1] |

[1]not observed

Analysis on SDS-PAGE gel allowed determining under reducing conditions a reconstruction of 96% and under non-reducing conditions an average MAR of 1.88.

Example 10: Trastuzumab—Compound (20) Conjugate

Reagents

Bioconjugation buffer 1, 5 mg/mL trastuzumab in bioconjugation buffer, reducing agent 1 (7.0 eq), compound (20) (10.6 eq) at a concentration of 1 mM in a mixture of 80% DMF and 20% MeOH.

Method

Bioconjugation reaction 2.

Denaturing HRMS Analysis According to Method 1

The results are shown in Table 13 below.

TABLE 13

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | n.o.[2] | | n.o.[2] | | 3 | 23439 |
| MAR 1 | 81 | 145997 | 100 | 73411 | 97 | 24261 |
| MAR 2 | 19 | 146822 | n.o.[2] | | n.o.[2] | |
| MAR 3 | n.o.[2] | | n.o.[2] | | n.o.[2] | |
| Average MAR | 1.19 | | 1.00 | | 0.97 | |

[1]molecular mass of the deglycosylated species

[2]not observed

HRMS analysis allowed determining an average MAR of 1.19 for the LHHL species and an average MAR of 1.00 for the LH species. LHH, HH and H species were not observed.

SDS-PAGE Gel Analysis Under Denaturing Non-Reducing and Reducing Conditions

The results are shown in Table 14 below.

TABLE 14

| | DTT | Species | | | | | |
|---|---|---|---|---|---|---|---|
| | | LHHL | LHH | HH | LH | H | L |
| Optical density | − | 94 | n.o.[1] | n.o.[1] | 3 | n.o.[1] | 3 |
| (%) | + | 77 | n.o.[1] | 3 | 6 | 7 | 6 |

[1]not observed

Analysis on SDS-PAGE gel allowed determining under reducing conditions a reconstruction of 77% and under non-reducing conditions an average MAR of 1.22.

Example 11: Trastuzumab—Compound (20)—Compound (22) Conjugate

Reagents Bioconjugation buffer 1, 5 mg/mL trastuzumab in bioconjugation buffer, reducing agent 1, compound (20) ($1^{st}$ compound) (10.6 eq) at a concentration of 3 mM in a mixture of 20% DMF and 80% MeOH, compound (22) ($2^{nd}$ compound) (11.7 eq) at a concentration of 10 mM in DMSO.

Method

Bioconjugation reaction 3.

The reaction mixture was purified on PD-10 (GE Healthcare) with PBS buffer Gibco© pH 7.4.

Denaturing HRMS Analysis According to Method 1

The results are shown in Table 15 below.

TABLE 15

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 100 | 74674 |
| MAR 2 | 100 | 149347 | n.o.[2] | |
| MAR 3 | n.o.[2] | | n.o.[2] | |
| Average MAR | 2.00 | | 1.00 | |

[1]molecular mass of the deglycosylated species

[2]not observed

HRMS analysis allowed determining an average MAR of 2.00 for LHHL species and an average MAR of 1.00 for LH species. LHH, HH, H and L species were not observed. No mass increment corresponding to compound (20) is observed: the trastuzumab-compound (20) conjugate has been entirely converted.

SDS-PAGE Gel Analysis Under Denaturing Non-Reducing and Reducing Conditions

The results are shown in Table 16 below.

TABLE 16

| | DTT | Species | | | | | |
|---|---|---|---|---|---|---|---|
| | | LHHL | LHH | HH | LH | H | L |
| Optical density | − | 90 | n.o.[1] | n.o.[1] | 10 | n.o.[1] | n.o.[1] |
| (%) | + | 97 | n.o.[1] | n.o.[1] | 3 | n.o.[1] | n.o.[1] |

[1]not observed

Analysis on SDS-PAGE gel allowed determining under reducing conditions a reconstruction of 97% and under non-reducing conditions an average MAR of 2.00.

Example 12: Trastuzumab—Compound (20)—Compound (22) Conjugate

Reagents

Bioconjugation buffer 1, 5 mg/mL trastuzumab in bioconjugation buffer, reducing agent 1, compound (20) ($1^{st}$ compound) (10.6 eq) at a concentration of 1 mM in a mixture of 80% DMF and 20% MeOH, compound (22) ($2^{nd}$ compound) (11.7 eq) at a concentration of 10 mM in DMSO.

Method

Bioconjugation reaction 3.

Denaturing HRMS Analysis According to Method 1

The results are shown in Table 17 below.

TABLE 17

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | n.o.[2] | | 14 | 72585 | 100 | 23439 |
| MAR 1 | 83 | 147259 | 86 | 74674 | n.o.[2] | |
| MAR 2 | 17 | 149352 | n.o.[2] | | n.o.[2] | |
| MAR 3 | n.o.[2] | | n.o.[2] | | n.o.[2] | |
| Average MAR | 1.17 | | 1.00 | | 0.00 | |

[1]molecular mass of the deglycosylated species
[2]not observed

HRMS analysis allowed determining an average MAR of 1.17 for LHHL species and an average MAR of 1.00 for LH species. LHH, HH, H and L species were not observed. No mass increment corresponding to compound (20) is observed: the trastuzumab-compound (20) conjugate has been entirely converted.

SDS-PAGE Gel Analysis Under Denaturing Non-Reducing and Reducing Conditions

The results are shown in Table 18 below.

TABLE 18

| Species | DTT | LHHL | LHH | HH | LH | H | L |
|---|---|---|---|---|---|---|---|
| Optical | – | 97 | n.o.[1] | no[1] | 3 | n.o.[1] | n.o.[1] |
| density (%) | + | 75 | n.o.[1] | n.o.[1] | 8 | 10 | 7 |

[1]not observed

Analysis on SDS-PAGE gel allowed determining under reducing conditions a reconstruction of 75% and under non-reducing conditions an average MAR of 1.19.

Example 13: MMAE 3-(2,6-bis(bromomethyl)isonicotinamido)-2-((2,6bis(bromomethyl)isonicotinamido)methyl)propamido-N-hexanamide-valine-citrulline-p-aminobenzoyl carbamate (23)

(23)

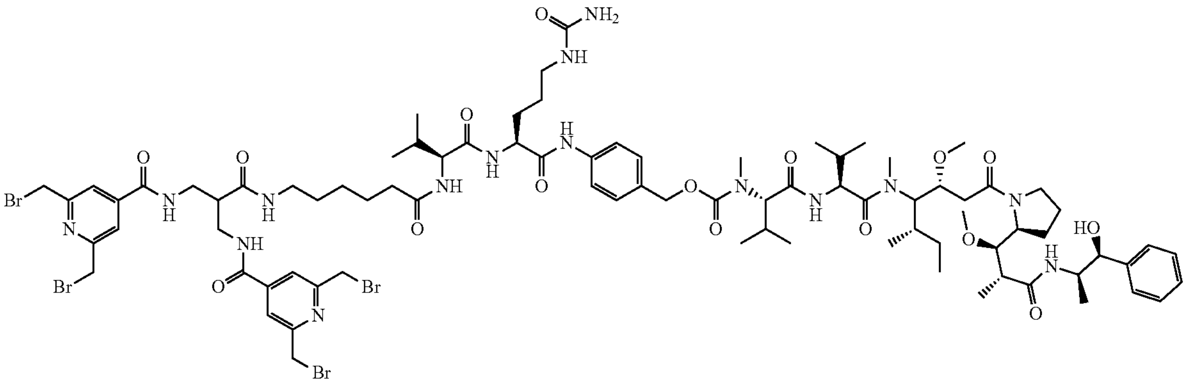

Under an inert atmosphere, in the dark and under anhydrous conditions, 3-(2,6-bis(bromomethyl)isonicotinamido)-2-((2,6-bis(bromomethyl)isonicotinamido)methyl)-propanoic acid (17) (12.0 mg; 0.017 mmol; 1.5 eq) was suspended in anhydrous MeCN (1.3 mL) then EEDQ (34.2 mg; 0.138 mmol; 12.0 eq) was added. The activation medium was stirred under argon at 25° C. for 30 min. A solution of MMAE 6-aminohexanamide-valine-citrulline-p-aminobenzoyl carbamate trifluoroacetic acid salt (6) (15.5 mg; 0.012 mmol; 1.0 eq), dissolved in anhydrous DMF (1.1 mL) in the presence of DIPEA (8.0 μL; 0.046 mmol; 4.0 eq), was added to the activation medium. Then DIPEA (8.0 μL; 0.046 mmol; 4.0 eq) was added to the reaction medium. The reaction medium was stirred under argon in the dark and at 0.25° C. for 1 h 30. The mixture was diluted with DMF (1 mL) and purified by semi-preparative high-pressure liquid chromatography ($t_R$=27.35 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% B over 37 min then 100% B over 6 min at 17.1 mL/min) to give (23) (13.9 mg; 63%) in the form of a white solid.

$^1$H NMR (300 MHz, DMSO) δ 9.99 (s; 1H); 8.91 (t; J=5.6 Hz; 2H); 8.32 (s; 1H); 8.10 (d; J=7.8 Hz; 1H); 7.98-7.89 (m; 2H); 7.87-7.82 (m; 4H); 7.73 (d; J=8.3 Hz; 1H); 7.67-7.51 (m; 3H); 7.41-7.22 (m; 6H); 7.18 (t; J=7.1 Hz; 1H); 5.97 (t; J=5.0 Hz; 1H); 5.42 (s; 2H); 5.02 (dd; 3=29.8; 10.6 Hz; 1H); 4.79 (d; J=11.7 Hz; 1H); 4.72 (s; 8H); 4.67-4.57 (m; 1H); 4.53-4.32 (m; 2H); 4.32-4.14 (m; 2H); 4.09-3.87 (m; 2H); 3.78 (d; J=8.6 Hz; 3H); 3.62-3.53 (m; 2H); 3.21 (dd; 1=14.9; 6.2 Hz; 5H); 3.12 (s; 1H); 3.08-2.93 (m; 3H); 2.86 (d; J=10.4 Hz; 3H); 2.18-2.02 (m; 3H); 2.02-1.87 (m; 2H); 1.86-1.62 (m; 2H); 1.61-1.45 (m; 2H); 1.43-1.26 (m; 6H); 1.15 (dd; J=13.5; 7.3 Hz; 1H); 1.01 (dt; J=15.2; 7.6 Hz; 5H); 0.91-0.67 (m; 25H).

HRMS (ESI): neutral mass calculated for $C_{84}H_{123}N_{15}O_{16}Br_4$ [M]: 1913.6006; observed 1913.6059.

Example 14: Trastuzumab—Compound (23) Conjugate

Reagents

Bioconjugation buffer 2, 5 mg/mL trastuzumab in bioconjugation buffer, reducing agent 2 (8.0 eq), compound (23) (5.0 eq) at a concentration of 0.4 mM in a mixture of 80% DMF and 20% MeOH.

Method

Bioconjugation reaction 1.

Denaturing HRMS Analysis According to Method 1

The results are shown in Table 19 below.

TABLE 19

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 100 | 74184 |
| MAR 2 | 100 | 148367 | n.o.[2] | |
| MAR 3 | n.o.[2] | | n.o.[2] | |
| Average MAR | 2.00 | | 1.00 | |

[1]molecular mass of the deglycosylated species
[2]not observed

HRMS analysis allowed determining an average MAR of 2.00 for LHHL species and an average MAR of 1.00 for LH species. LHH, HH, H and L species were not observed.

SDS-PAGE Gel Analysis Under Denaturing Non-Reducing and Reducing Conditions

The results are shown in Table 20 below.

TABLE 20

| Species | DTT | LHHL | LHH | HH | LH | H | L |
|---|---|---|---|---|---|---|---|
| Optical density (%) | − | 68 | n.o.[1] | n.o.[1] | 32 | n.o.[1] | n.o.[1] |
| | + | 61 | n.o.[1] | 5 | 27 | 6 | 2 |

[1]not observed

Analysis on SDS-PAGE gel allowed determining under reducing conditions a reconstruction of 61% and under non-reducing conditions an average MAR of 2.00.

Example 15: Methyl 3,5-bis(2,6-bis(bromomethyl)isonicotinamido)benzoate (26)

General reaction scheme

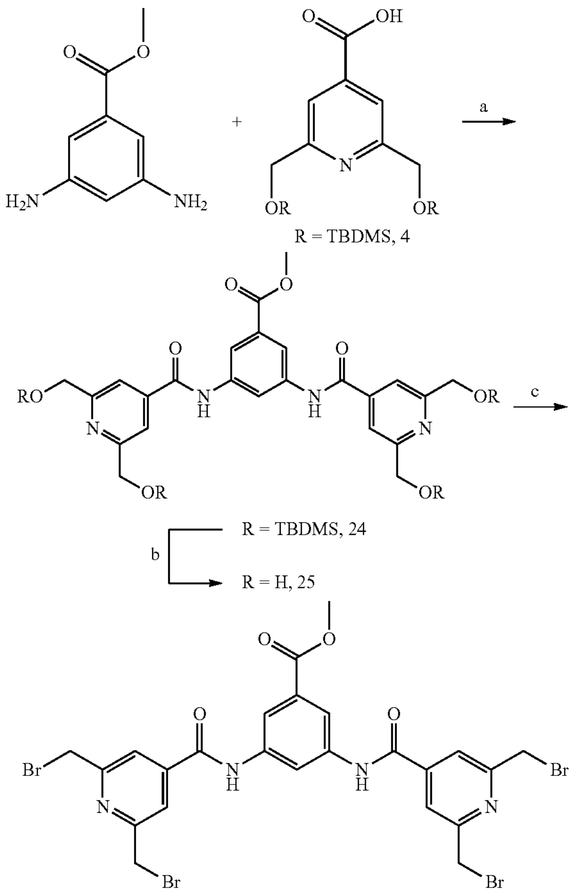

26 a HATU, 2,6-lutidine, DMF, 20 h, RT;
b TBAF, THF, 21 h, RT;
c $PBr_3$, MeCN, DMF, 7 h, 45° C.

Step 1: Methyl 3,5-bis(2,6-bis(((tert-butyldimethylsilyl)oxy)methyl)-isonicotinamido)benzoate (24)

(24)

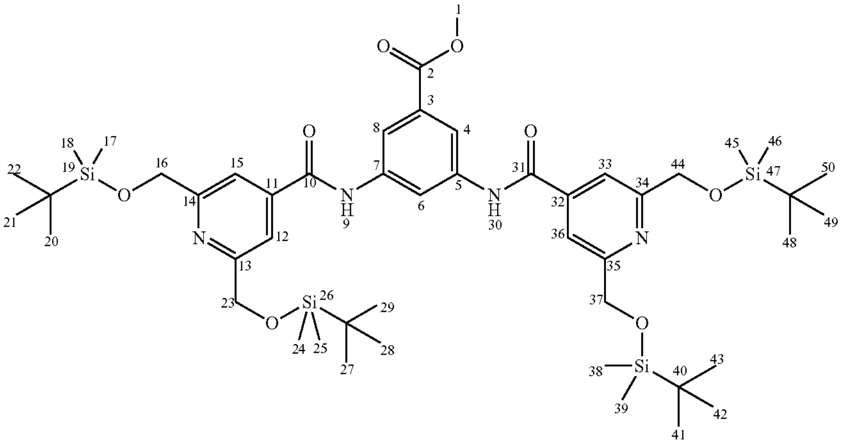

2,6-Bis(((tert-butyldimethylsilyl)oxy)methyl)isonicotinic acid (4) (1.39 g; 3.376 mmol; 2.5 eq) was suspended in peptide DMF (8.0 mL), then HATU (1.54 g; 4.050 mmol; 3.0 eq) and 2,6-lutidine (0.63 mL; 5.439 mmol; 4.0 eq) were added. The activation solution was stirred under argon at RT (25° C.) for 45 min. Then a solution of methyl 3,5-diamino-benzoate (225 mg; 1.354 mmol; 1.0 eq), dissolved in peptide DMF (1.0 mL) was added. The reaction medium was stirred at RT (25° C.) for 20 h. The reaction mixture was taken up in AcOEt and concentrated under reduced pressure. The crude was purified by flash chromatography (cyclohexane/AcOEt, 85:15) to give (24) (778 mg; 60%) in the form of an off-white solid.

$^1$H NMR (300 MHz, DMSO) δ 10.91 (s; $2H_{9,30}$); 8.66 (t; J=2.0 Hz; $1H_6$); 8.21 (d; J=2.0 Hz; $2H_{4,8}$); 7.80 (s; $4H_{12,15,33,36}$); 4.82 (S; $8H_{16,23,37,44}$); 3.90 (s; 3H1); 0.93 (s; $36H_{20-22,27-29,41-43,48-50}$); 0.12 (s; $24H_{17,18,24,25,38,39,45,46}$).

$^{13}$C NMR (75 MHz, $CDCl_3$) δ 166.4 ($1C_2$); 165.1 (2C10, 31); 162.1 ($4C_{13,14,34,35}$); 143.3 (2C5,7); 138.7 ($2C_{11,32}$); 132.0 ($1C_3$); 117.5 ($2C_{4,5}$); 116.1 ($1C_6$); 115.5 ($4C_{12,15,33,36}$); 66.0 ($4C_{16,23,37,44}$); 52.6 ($1C_1$); 26.1 ($12C_{20-22,27-29,41-43,48-50}$); 18.6 ($4C_{19,26,40,47}$); −5.2 ($8C_{17,18,24,25,38,39,45,46}$).

HRMS (ESI): m/z calculated for $C_{48}H_{81}N_4O_8Si_4$ $[M+H]^+$: 953.5126; observed 953.5121.

Step 2: Methyl 3,5-bis(2,6-bis(hydroxymethyl)isonicotinamido)benzoate (25)

Methyl 3,5-bis(2,6-bis(((tert-butyldimethylsilyl)oxy)methyl)isonicotinamido)benzoate (24) (119 mg; 0.125 mmol; 1.0 eq) was dissolved in anhydrous THF (560 μL) and a solution of 1 M TBAF in THF (580 μL; 0.580 mmol; 4.6 eq) was added. The reaction medium was stirred under argon at RT for 21 h. The THF was evaporated under reduced pressure and the residue was taken up in DMSO (3.0 mL) and purified by semi-preparative high-pressure liquid chromatography ($t_R$=10.6 mi; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried outwit 0.1% of TEA (by volume) in water (solvent A), and MeCN (solvent B); gradient 5 to 60% of B over 34 min then 100% of B over 5 min at 17.1 mL/min) to give (25) (62 mg; 100%) in the form of a pale yellow solid.

$^1$H NMR (300 MHz, DMSO) δ 10.89 (s; $2H_{9,20}$); 8.73 (t; 3=2.0 Hz; $1H_6$); 8.22 (d; 3=2.0 Hz; $2H_{4,8}$); 7.88 (s; $4H_{12,15,23,2}$); 4.64 (s; $8H_{16,18,27,29}$); 3.90 (s; $3H_1$).

$^{13}$C NMR (75 MHz, DMSO) δ 165.9 (1C2); 164.8 ($2C_{1,21}$); 162.0 ($4C_{13,14,24,25}$) 143.0 ($2C_{5,7}$); 139.4 ($2C_{11,22}$); 130.3 ($1C_3$); 117.0 ($3C_{4,6,8}$); 116.3 ($4C_{11,12,15,23,26}$); 64.1 ($4C_{13,14,24,25}$); 52.4 ($1C_1$).

HRMS (ESI): neutral mass calculated for $C_{24}H_{24}N_4O_8$ [M]: 496.1594; observed 496.1597.

(25)

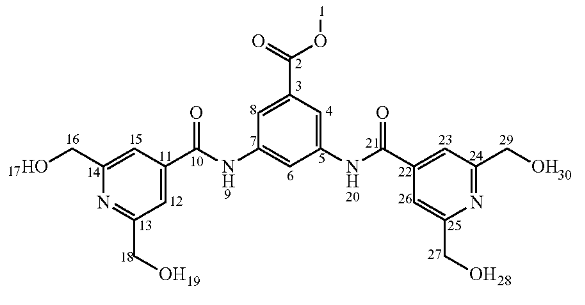

Step 3: methyl 3,5-bis(2,6-bis(bromomethyl) isonicotinamido)benzoate (26)

(26)

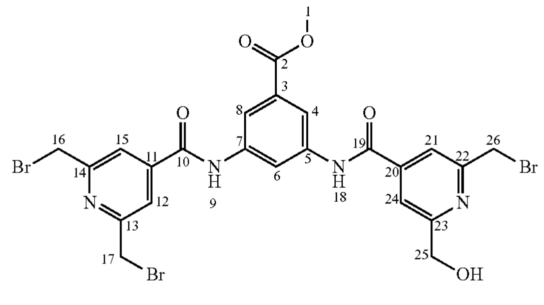

Methyl 3,5-bis(2,6-bis(((tert-butyldimethylsilyl)oxy)methyl)isonicotinamido)benzoate (25) (64 mg; 0.129 mmol; 1.0 eq) was suspended in anhydrous MeCN (5 mL) then $PBr_3$ (74 μL; 0.780 mmol; 6.0 eq) was added dropwise. The suspension was stirred under argon at 45° C. for 4 h. After returning to RT, 1 mL of anhydrous DMF was added, then the solution was stirred under argon at 45° C. for 3 h. The reaction medium was neutralized with water (10 mL) and extracted with AcOEt (3×30 mL). The combined organic phases were washed with a saturated NaCl solution, dried on $MgSO_4$, filtered and concentrated under reduced pressure. The product was purified by flash chromatography ($SiO_2$, DCM/AcOEt, 80:20) to give (26) (41 mg; 43%) in the form of a white solid.

$^1H$ NMR (300 MHz, DMSO) δ 10.89 (s; $2H_{9,18}$); 8.72 (s; $1H_6$); 8.19 (s; $2H_{4,8}$); 8.00 (s; $4H_{12,15,21,24}$); 4.79 (S; $8H_{16,17,25,26}$); 3.90 (s; $3H_1$).

$^{13}C$ NMR (75 MHz, DMSO) δ 165.8 ($1C_2$); 163.5 ($2C_{10,19}$); 157.6 ($4C_{13,14,22,23}$); 144.1 ($2C_{5,7}$); 139.2 ($2C_{11,20}$); 130.4 ($1C_3$); 121.2 ($4C_{12,15,21,24}$); 117.0 ($2C_{4,8}$); 116.6 ($1C_6$); 52.4 ($1C_1$); 34.0 ($4C_{16,17,25,26}$).

HRMS (ESI): neutral mass calculated for $C_{24}H_{20}Br_4N_4O_4$ [M]: 743.8218; observed 743.8207.

Example 16: Trastuzumab—Compound (26) Conjugate

Reagents

Bioconjugation buffer 1, 5 mg/mL trastuzumab in bioconjugation buffer, reducing agent 1 (8.0 eq), compound (26) (12.0 eq) at a concentration of 1 mM in a mixture of 20% DMF and 80% MeOH.

Method

Bioconjugation reaction 1.

Denaturing HRMS Analysis According to Method 1

The results are shown in Table 21 below.

TABLE 21

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | n.o.[2] | | n.o.[2] | | 100 | 23424 |
| MAR 1 | n.o.[2] | | 100 | 73014 | n.o.[2] | |
| MAR 2 | 64 | 146027 | n.o.[2] | | n.o.[2] | |
| MAR 3 | 36 | 146456 | n.o.[2] | | n.o.[2] | |
| Average MAR | 2.36 | | 1.00 | | 0 | |

[1]molecular mass of the deglycosylated species
[2]not observed

HRMS analysis allowed determining an average MAR of 2.36 for LHHL species and an average MAR of 1.00 for LH species. LHH, HH and H species were not observed SDS-PAGE Gel Analysis Under Denaturing Non-Reducing and Reducing Conditions The results are shown in Table 22 below.

TABLE 22

| Species | DTT | LHHL | LHH | HH | LH | H | L |
|---|---|---|---|---|---|---|---|
| Optical density (%) | – | 83 | n.o.[1] | n.o.[1] | 16 | 1 | n.o.[1] |
| | + | 78 | n.o.[1] | n.o.[1] | 18 | 4 | n.o.[1] |

[1]not observed

Analysis on SDS-PAGE gel allowed determining under reducing conditions a reconstruction of 78% and under non-reducing conditions an average MAR of 2.30.

Example 17: 3,5-bis(2,6-bis(bromomethyl)isonicotinamido)benzoic acid (28)

General reaction scheme

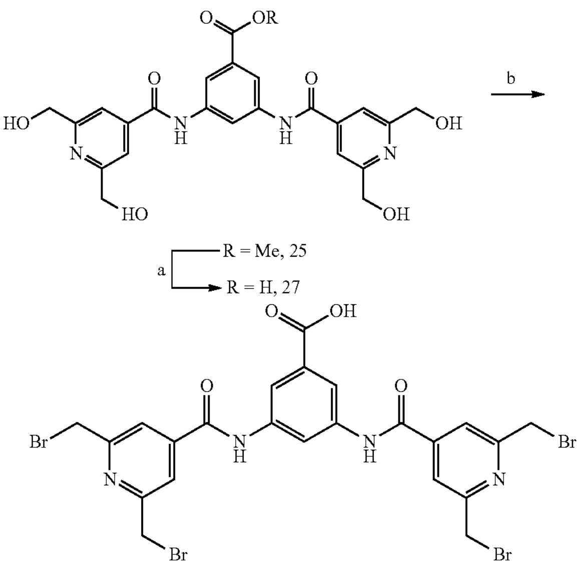

28 a LiOH, THF, $H_2O$, 43 h, RT;
b $PBr_3$, DMF, 3 h 30, 0° C. then RT.

Step 1: 3,5-bis(2,6-bis(hydroxymethyl)isonicotinamido)benzoic acid (27)

(27)

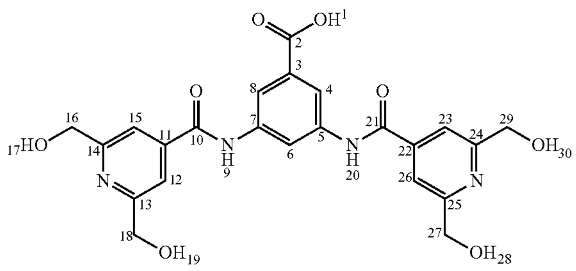

Methyl 3,5-bis(2,6-bis(hydroxymethyl)isonicotinamido)benzoate (25) (312 mg; 0.628 mmol; 1.0 eq) was suspended in THF (35 mL) and a solution of hydrated LiOH (42 mg; 1.754 mmol; 2.8 eq) in water (17.5 mL) was added. The reaction medium was stirred at RT (25° C.) for 43 h. The medium was acidified with an aqueous solution of 1N HCl to pH 1 and the THF was evaporated under reduced pressure. The aqueous residue was purified by semi-preparative high-pressure liquid chromatography ($t_R$=10.9 min; on the Gilson PLC 2050 system [ARMEN V2 (pump) and ECOM TOY-DAD600 (UV detector)] UV detection at 254 nm at 25° C.;

Waters XBridge™ column C-18; 5 μm (250 mm×19.00 mm); elution carried out with 0.1% TFA (by volume) in water (solvent A), and MeCN (solvent B); gradient 5 to 60% of B over 40 min then 100% of B over 5 min at 17.1 mL/min) to give (27) (252 mg; 83%) in the form of a pale yellow solid.

$^{1}$H NMR (300 MHz, DMSO) δ 10.83 (s; $2H_{9,20}$); 8.67 (t; J=1.7 Hz; $1H_{6}$); 8.18 (d; J=2.0 Hz; $2H_{4,8}$); 7.86 (s; $4H_{12,15,23,26}$); 5.56 (t; J=5.8 Hz; $4H_{17,19,28,30}$); 4.63 (d; J=5.7 Hz; $8H_{16,18,27,29}$).

$^{13}$C NMR (75 MHz, DMSO) δ 167.0 ($1C_{2}$); 164.8 ($2C_{10,21}$); 162.0 ($4C_{13,14,24,25}$); 143.0 ($2C_{5,7}$); 139.3 ($2C_{11,22}$); 131.5 ($1C_{3}$); 117.3 ($2C_{4,8}$); 116.7 ($1C_{6}$); 116.3 ($4C_{12,15,23,26}$); 64.1 ($4C_{16,18,27,29}$).

HRMS (ESI): neutral mass calculated for $C_{23}H_{22}N_{4}O_{8}$ [M]: 482.1438; observed 482.1447.

Step 2: 3,5-bis(2,6-bis(bromomethyl) isonicotinamido)benzoic acid (28)

(28)

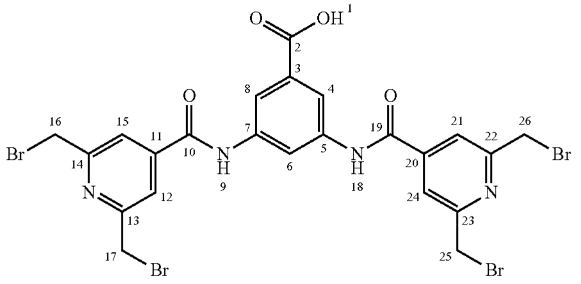

3,5-bis(2,6-bis(hydroxymethyl)isonicotinamido)benzoic acid (27) (20 mg; 0.041 mmol; 1.0 eq) was suspended in anhydrous DMF (1.3 mL) at 0° C. then $PBr_{3}$ (32 μL; 0.337 mmol; 8.2 eq) was added dropwise. The suspension was stirred under argon at RT (25° C.) for 3 h 30. The reaction medium was neutralized with water (1.5 mL), the white precipitate formed was filtered, rinsed with water and with n-pentane to give (28) (24 mg; 81%) in the form of a white solid.

$^{1}$H NMR (300 MHz, $CD_{3}OD$) δ 8.59 (t; J=2.1 Hz; $1H_{6}$); 8.21 (d; J=2.1 Hz; $2H_{4,8}$); 7.97 (s; $4H_{12,15,21,24}$); 4.69 (s; $8H_{16,17,25,26}$).

$^{13}$C NMR (75 MHz, $CD_{3}OD$) δ 167.0 ($1C_{2}$); 165.8 (2C10,19); 159.6 ($4C_{13,14,22,23}$); 146.3 ($2C_{5,7}$); 140.2 ($2C_{11,20}$); 133.3 ($1C_{3}$); 122.2 ($4C_{12,15,21,24}$); 119.6 ($2C_{4,8}$); 118.8 ($1C_{6}$); 33.3 ($4C_{16,17,25,26}$).

HRMS (ESI): neutral mass calculated for $C_{23}H_{18}Br_{4}N_{4}O_{4}$ [M]: 729.8062; observed 729.8069.

Example 18: Trastuzumab—Compound (28) Conjugate

Reagents

Bioconjugation buffer 1, 5 mg/mL trastuzumab in bioconjugation buffer, reducing agent 1 (12.0 eq), compound (28) (12.0 eq) at a concentration of 1 mM in a mixture of 20% DMF and 80% MeOH.

Method

Bioconjugation reaction 1.

Denaturing HRMS Analysis According to the Method 1

The results are shown in Table 23 below.

TABLE 23

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | n.o.[2] | | n.o.[2] | | 100 | 23405 |
| MAR 1 | n.o.[2] | | 100 | 73001 | n.o.[2] | |
| MAR 2 | 73 | 146001 | n.o.[2] | | n.o.[2] | |
| MAR 3 | 27 | 146414 | n.o.[2] | | n.o.[2] | |
| Average MAR | 2.27 | | 1.00 | | 0.00 | |

[1]molecular mass of the deglycosylated species
[2]not observed

HRMS analysis allowed determining an average MAR of 2.27 for LHHL species and an average MAR of 1.00 for LH species. LHH, HH and H species were not observed.

SDS-PAGE Gel Analysis Under Denaturing Non-Reducing and Reducing Conditions

The results are shown in Table 24 below.

TABLE 24

| Species | DTT | LHHL | LHH | HH | LH | H | L |
|---|---|---|---|---|---|---|---|
| Optical density (%) | − | 58 | n.o.[1] | 2 | 28 | 6 | 6 |
| | + | 56 | n.o.[1] | 3 | 33 | 4 | 4 |

[1]not observed

Analysis on SDS-PAGE gel allowed determining under reducing conditions a reconstruction of 56% and under non-reducing conditions an average MAR of 2.19.

Example 19: Trastuzumab—Compound (28) Conjugate

Reagents

Bioconjugation buffer 1, 5 mg/mL trastuzumab in bioconjugation buffer, reducing agent 1 (12.0 eq), compound (28) (12.0 eq) at a concentration of 1 mM in a mixture of 20% DMF and 80% MeOH.

Method

Bioconjugation reaction 2.

Denaturing HRMS Analysis According to Method 1

The results are shown in Table 25 below.

TABLE 25

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | n.o.[2] | | n.o.[2] | | 100 | 23405 |
| MAR 1 | 60 | 145586 | 100 | 73001 | n.o.[2] | |
| MAR 2 | 40 | 145600 | n.o.[2] | | n.o.[2] | |
| MAR 3 | n.o.[2] | | n.o.[2] | | n.o.[2] | |
| Average MAR | 1.40 | | 1.00 | | 0.00 | |

[1]molecular mass of the deglycosylated species
[2]not observed

HRMS analysis allowed determining an average MAR of 1.40 for the LHHL species and an average MAR of 1.00 for the LH species. LHH, HH and H species were not observed.

SDS-PAGE Gel Analysis Under Denaturing Non-Reducing and Reducing Conditions

The results are shown in Table 26 below.

TABLE 26

| Species | DTT | LHHL | LHH | HH | LH | H | L |
|---|---|---|---|---|---|---|---|
| Optical | – | 82 | n.o.[1] | 1 | 4 | 10 | 3 |
| density | + | 60 | n.o.[1] | 2 | 12 | 14 | 12 |
| (%) | | | | | | | |

[1]not observed

Analysis on SDS-PAGE gel allowed determining under reducing conditions a reconstruction of 60% and under non-reducing conditions an average MAR of 1.43.

Example 20: Methyl 6-(3,5-bis(2,6-bis(bromomethyl)isonicotinamido)benzamido)-hexanoate (30)

General reaction scheme

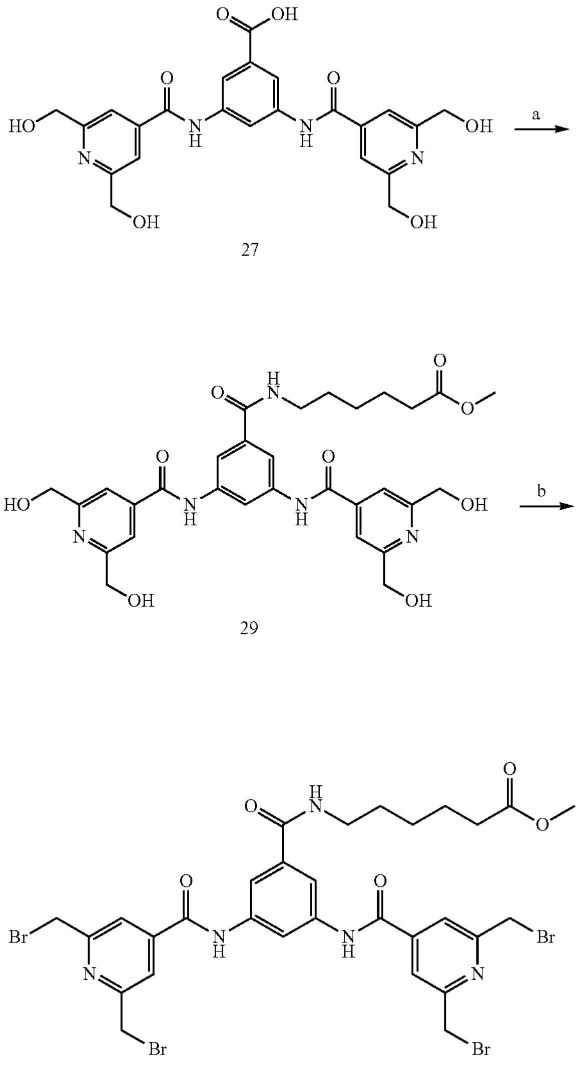

27, 29, 30 a $NH_2(CH_2)_5CO_2CH_3$•HCl, HATU, 2,6-lutidine, DMF, 25 h, 0° C. then RT;
b $PBr_3$, DMF, 2 h, 45° C.

Step 1: Methyl 6-(3,5-bis(2,6-bis(hydroxymethyl)isonicotinamido)benzamido)-hexanoate (29)

(29)

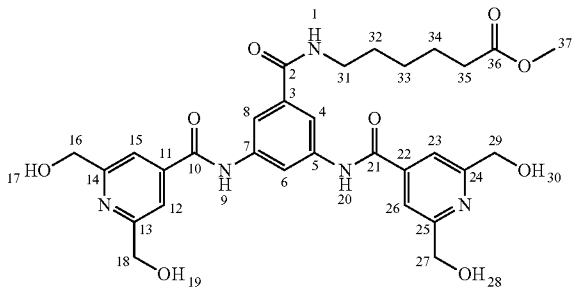

3,5-bis(2,6-bis(hydroxymethyl)isonicotinamido)benzoic acid (27) (98 mg; 0.203 mmol; 1.0 eq) was suspended in anhydrous DMF (8.0 mL) under argon at 0° C., then HATU (116 mg; 0.305 mmol; 1.5 eq) and 2,6-lutidine (110 μL; 0.950 mmol; 4.7 eq) were added. The activation solution was stirred under argon at 0° C. for 15 min. Then methyl 6-aminohexanoate hydrochloride (44 mg; 0.242 mmol; 1.2 eq) was added. The reaction medium was stirred under argon at RT (25° C.) for 25 h. The reaction mixture was concentrated under reduced pressure and purified by semi-preparative high-pressure liquid chromatography ($t_R$=16.4 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 5 to 60% B over 40 min then 100% B over 5 min at 17.1 mL/min) to give (29) (110 mg; 89%) in the form of a pale yellow solid.

$^1$H NMR (300 MHz, DMSO) δ 10.80 (s; $2H_{9,20}$); 8.49 (t; J=1.8 Hz; $1H_6$); 8.48-8.41 (m; $1H_1$); 7.94 (d; J=1.9 Hz; $2H_{4,8}$); 7.87 (s; $4H_{12,15,23,26}$); 4.64 (s; $8H_{16,18,27,29}$); 3.58 (s; $3H_{37}$); 3.30-3.20 (m; $2H_{31}$); 2.32 (t; J=7.4 Hz; $2H_{35}$); 1.64-1.47 (m; $4H_{32,34}$); 1.40-1.26 (m; 2H33).

$^{13}$C NMR (75 MHz, DMSO) δ 173.4 (1C36); 166.3 ($1C_2$); 164.4 ($2C_{10,21}$); 161.5 ($4C_{13,14,24,25}$); 143.9 ($2C_{5,7}$); 138.8 ($2C_{11,22}$); 136.2 ($1C_3$); 116.9 ($4C_{12,15,23,26}$); 115.9 ($2C_{4,5}$); 115.7 ($1C_6$); 63.5 ($4C_{16,18,27,29}$); 51.2 ($1C_{37}$); 38.9 under DMSO ($1C_{31}$); 33.3 ($1C_{35}$); 28.8 ($1C_{32}$); 26.0 ($1C_{33}$); 24.2 ($1C_{34}$).

HRMS (ESI): neutral mass calculated for $C_{30}H_{35}N_5O_9$ [M]: 609.2435; observed 609.2429.

Step 2: Methyl 6-(3,5-bis(2,6-bis(bromomethyl) isonicotinamido)benzamido)-hexanoate (30)

(30)

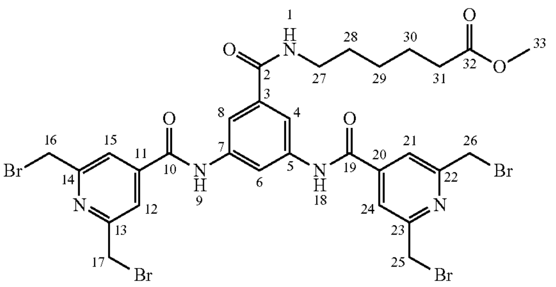

Methyl 6-(3,5-bis(2,6-bis(hydroxymethyl)isonicotinamido)benzamido)hexanoate (29) (22 mg; 0.036 mmol; 1.0 eq) was dissolved in anhydrous DMF (1.4 mL) then $PBr_3$ (21 μL; 0.221 mmol; 6.2 eq) was added dropwise. The suspension was stirred under argon at 45° C. for 50 min. The viscous cream-white reaction medium was suspended by adding anhydrous DMF (1.4 mL). The white suspension obtained was stirred at 45° C. for 1 h 10. After returning to RT, the reaction medium was neutralized with water and extracted with AcOEt (3×30 mL). The combined organic phases were washed with a saturated NaCl solution, dried on $MgSO_4$, filtered and concentrated under reduced pressure. The product was purified by flash chromatography ($SiO_2$, dichloromethane/ethyl acetate, 70:30) then by semi-preparative high-pressure liquid chromatography ($t_R$=24.3 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% B over 32 min then 100% B over 6 min at 17.1 mL/min) to give (30) (9 mg; 29%) in the form of a white solid.

$^1H$ NMR (300 MHz, DMSO) δ 10.89 (s; $2H_{9,18}$); 8.95 (s; 1H1); 8.64 (t; J=1.8 Hz; $1H_6$); 7.98 (s; $4H_{12,15,21,24}$); 7.77 (d; J=2.0 Hz; $2H_{4,5}$); 4.79 (s; $8H_{16,17,25,26}$); 3.75 (t; 3=7.2 Hz; $2H_{27}$); 3.57 (s; $3H_{33}$); 2.32 (t; J=7.4 Hz; $2H_{31}$); 1.63-1.51 (m; $4H_{28,30}$); 1.38-1.28 (m; $2H_{29}$).

$^1H$ NMR (300 MHz, $CDCl_3$) δ 9.13-9.02 (m; $2H_{9,18}$); 8.94 (s; 1H1); 8.49 (t; J=1.9 Hz; $1H_6$); 7.82 (s; $4H_{12,15,21,24}$); 7.64 (d; J=1.6 Hz; $2H_{4,8}$); 4.57 (s; $8H_{16,17,25,26}$); 3.84 (t; J=6.4 Hz; $2H_{27}$); 3.56 (s; $3H_{33}$); 2.33 (t; J=7.1 Hz; $2H_{31}$); 1.72-1.54 (m; $4H_{28,30}$); 1.43-1.28 (m; $2H_{29}$).

$^{13}C$ NMR (75 MHz, $CDCl_3$) δ 175.0 ($1C_{32}$); 171.7 ($1C_2$); 163.8 (2C10,19); 158.3 ($4C_{13,14,22,23}$); 143.9 ($2C_{5,7}$); 139.0 ($2C_{11,20}$); 135.4 ($1C_3$); 120.6 ($4C_{12,15,21,24}$); 116.9 ($2C_{4,8}$); 115.6 ($1C_6$); 51.9 ($1C_{33}$); 40.6 ($1C_{27}$); 34.06 ($1C_{31}$); 32.9 ($4C_{16,17,25,26}$); 27.6 ($1C_{28}$); 26.3 ($1C_{29}$); 24.7 ($1C_{30}$).

HRMS (ESI): neutral mass calculated for $C_{30}H_{31}Br_4N_5O_5$ [M]: 856.9059; observed 856.9080.

Example 21: Trastuzumab—Compound (30) Conjugate

Reagents

Bioconjugation buffer 1, 5 mg/mL trastuzumab in bioconjugation buffer, reducing agent 1 (12.0 eq), compound (30) (12.0 eq) at a concentration of 1 mM in a mixture of 20% DMF and 80% MeOH.

Method

Bioconjugation reaction 1.

Denaturing HRMS analysis according to method 1

The results are shown in Table 27 below.

TABLE 27

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | n.o.[2] | | n.o.[2] | | 100 | 23439 |
| MAR 1 | n.o.[2] | | 100 | 73128 | n.o.[2] | |
| MAR 2 | 100 | 146255 | n.o.[2] | | n.o.[2] | |
| MAR 3 | n.o.[2] | | n.o.[2] | | n.o.[2] | |
| Average MAR | 2.00 | | 1.00 | | 0.00 | |

[1]molecular mass of the deglycosylated species
[2]not observed

HRMS analysis allowed determining an average MAR of 2.00 for LHHL species and an average MAR of 1.00 for LH species. LHH, HH and H species were not observed.

SDS-PAGE Gel Analysis Under Denaturing Non-Reducing and Reducing Conditions

The results are shown in Table 28 below.

TABLE 28

| Species | DTT | LHHL | LHH | HH | LH | H | L |
|---|---|---|---|---|---|---|---|
| Optical density (%) | − | 56 | n.o.[1] | 2 | 27 | 5 | 10 |
| | + | 54 | n.o.[1] | 2 | 24 | 7 | 13 |

[1]not observed

Analysis on SDS-PAGE gel allowed determining under reducing conditions a reconstruction of 54% and under non-reducing conditions an average MAR of 2.00.

Example 22: 6-(3,5-bis(2,6-bis(bromomethyl)isonicotinamido)-benzamido)hexanoic acid (32)

General reaction scheme

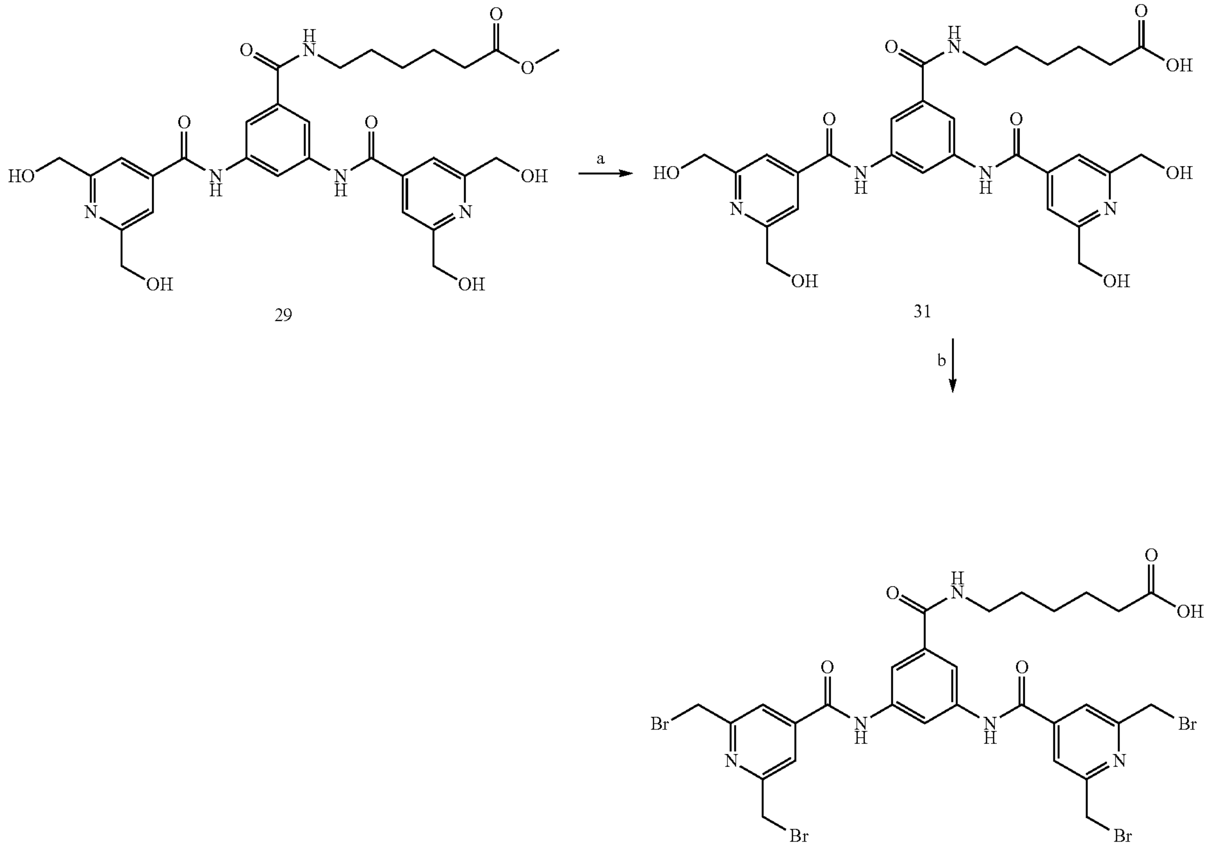

29 31 32 a LiOH, THF, $H_2O$, 25 h, RT;
b $PBr_3$, MeCN, 5 h, 45° C.

Step 1: 6-(3,5-bis(2,6-bis(hydroxymethyl)isonicotinamido)benzamido)-hexanoic acid (31)

(31)

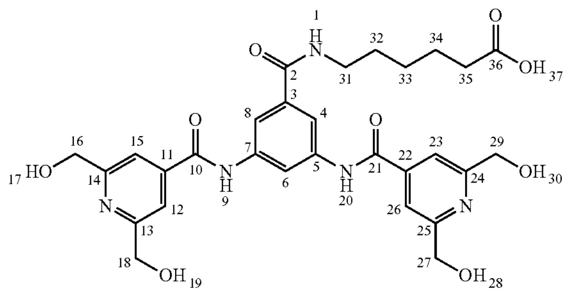

Methyl 6-(3,5-bis(2,6-bis(hydroxymethyl)isonicotinamido)benzamido)hexanoate (29) (110 mg; 0.180 mmol; 1.0 eq) was suspended in THF (9 mL) and a solution of 0.1 M LiOH (10.8 mg; 0.451 mmol; 2.5 eq) in water (4.5 mL) was added. The reaction medium was stirred at RT (25° C.) for 25 h. The medium was acidified with an aqueous solution of 1N HCl to pH 1 and the THF was evaporated under reduced pressure. The aqueous residue was purified by semi-preparative high-pressure liquid chromatography ($t_R$=13.4 min; on the Gilson PLC 2050 system [ARMEN V2 (pump) and ECOM TOYDAD600 (UV detector)] UV detection at 254 nm at 25° C.; Waters XBridge™ column C-18; 5 μm (250 mm×19.00 mm); elution carried out with 0.1% TFA (by volume) in water (solvent A), and MeCN (solvent B); gradient 5 to 60% of B over 40 min then 100% of B over 5 min at 17.1 mL/min) to give (31) (84 mg; 79%) in the form of a pale yellow solid.

$^1H$ NMR (300 MHz, DMSO) δ 10.82 (s; $2H_{9,20}$); 8.53-8.48 (m; $1H_6$); 8.48-8.42 (m; 1H1); 7.93 (d; J=1.6 Hz; $2H_{4,8}$); 7.90 (s; $4H_{12,15,23,26}$); 4.66 (s; $8H_{16,15,27,29}$); 3.31-3.19 (m; 2H31); 2.22 (t; J=7.3 Hz; $2H_{35}$); 1.62-1.46 (m; $4H_{32,34}$); 1.40-1.26 (m; $2H_{33}$).

$^{13}C$ NMR (75 MHz, DMSO) δ 174.5 ($1C_{36}$); 166.2 ($1C_2$); 164.5 ($2C_{10,21}$); 161.6 ($4C_{13,14,24,25}$); 143.5 ($2C_{5,7}$); 138.8 ($2C_{11,22}$); 136.1 ($1C_3$); 116.6 ($4C_{12,15,23,26}$); 115.8 ($2C_{4,5}$); 115.7 ($1C_6$); 63.7 ($4C_{16,18,27,29}$); 38.9 under DMSO ($1C_{31}$); 33.7 ($1C_{35}$); 28.8 ($1C_{32}$); 26.0 ($1C_{33}$); 24.3 ($1C_{34}$).

HRMS (ESI): neutral mass calculated for $C_{29}H_{33}N_5O_9$ [M]: 595.2278; observed 595.2271.

Step 2: 6-(3,5-bis(2,6-bis(bromomethyl)isonicotinamido)benzamido)-hexanoic acid (32)

(32)

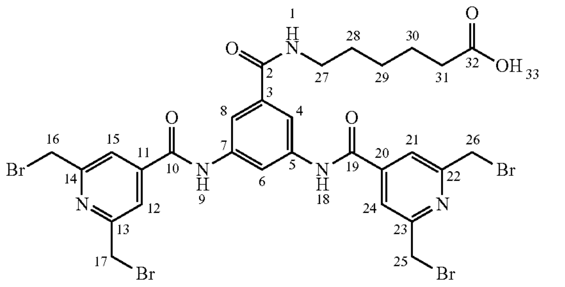

6-(3,5-bis(2,6-bis(hydroxymethyl)isonicotinamido)benzamido)hexanoic acid (31) (48.7 mg; 0.082 mmol; 1.0 eq) was suspended in anhydrous MeCN (4 mL) then $PBr_3$ (47 μL; 0.495 mmol; 6.0 eq) was added dropwise. The suspension was stirred under argon at 45° C. for 3 h 10. After returning to RT, additional $PBr_3$ (24 μL; 0.253 mmol; 3.1 eq) was added dropwise and the suspension was stirred under argon at 45° C. for 1 h 45. After cooling to 0° C., the reaction medium was neutralized with water and concentrated under reduced pressure. The aqueous residue (1 mL) was diluted in anhydrous DMF (3.5 mL) and the product was purified by semi-preparative high-pressure liquid chromatography ($t_R$=19.9 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% of TFA (by volume) in water (solvent A), and MeCN (solvent B); gradient 20 to 100% of B over 32 min then 100% of B over 6 min at 17.1 mL/min) to give (32) (6.0 mg; 9%) in the form of a white solid.

$^1$H NMR (300 MHz, DMSO) δ 12.00 (s; $1H_{33}$); 10.84 (s; $2H_{9,18}$); 8.64-8.36 (m; $2H_{1,6}$); 8.03 (s; $4H_{12,15,21,24}$); 7.93 (d; J=1.8 Hz; $2H_{4,8}$); 4.90 (s; $8H_{16,17,25,26}$); 3.28-3.20 (m; $2H_{27}$); 2.21 (t; $^3$=7.4 Hz; $2H_{31}$); 1.63-1.47 (m; $4H_{28,30}$); 1.43-1.26 (m; $2H_{29}$).

HRMS (ESI): neutral mass calculated for $C_{24}H_{29}Br_4N_5O_5$ [M]: 743.8218; observed 743.8207.

Example 23: MMAE 3,5-bis(2,6-bis(bromomethyl) isonicotinamido)benzamido —N-hexanamide-valine-citrulline-p-aminobenzoyl carbamate (33)

(33)

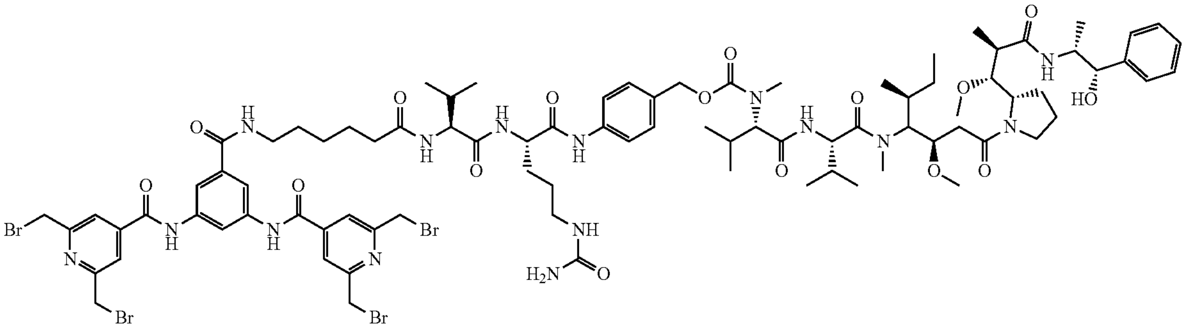

Under an inert atmosphere, in the dark and under anhydrous conditions, 3,5-bis(2,6-bis(bromomethyl)isonicotinamido)benzoic acid (28) (10.0 mg; 0.0136 mmol; 2.0 eq) was suspended in anhydrous MeCN (536 μL) EEDQ (10.0 mg; 0.0404 mmol; 6.0 eq) was added. The activation medium was stirred under argon at 25° C. for 1 h 30. A solution of MMAE 6-aminohexanamide-valine-citruiline-p-aminobenzoyl carbamate trifluoroacetic acid salt (6) (9.0 mg; 0.0067 mmol; 1.0 eq), dissolved in anhydrous DMF (134 μL) in the presence of DIPEA (4.7 μL; 0.0270 mmol; 4.0 eq), was added in the middle of activation. The reaction medium obtained was stirred at 25° C. for 2 h. The mixture was diluted by 2 with DMF and purified by semi-preparative high-pressure liquid chromatography ($t_R$=22.6 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% B over 32 min then 100% B over 6 min at 17.1 mL/min) to give (33) (6.0 mg; 46%) in the form of a white solid.

$^1$H NMR (300 MHz, DMSO) δ 10.82 (s; 2H); 10.06-9.91 (m; 1H); 8.57-8.44 (m; 2H); 8.18-8.03 (m; 2H); 8.00 (s; 4H); 7.93 (d; J=1.9 Hz; 2H); 7.92-7.76 (m; 2H); 7.70-7.53 (m; 3H); 7.39-7.21 (m; 7H); 7.21-7.10 (m; 1H); 6.01-5.92 (m; 1H); 5.61-5.22 (m; 6H); 5.15-4.96 (m; 3H); 4.79 (s; 8H); 4.54-4.45 (m; 2H); 4.45-4.33 (m; 3H); 4.30-4.15 (m; 3H); 4.12-3.89 (m; 4H); 3.26-2.91 (m; 9H); 2.91-2.80 (m; 4H); 2.23-2.06 (m; 1H); 2.05-1.88 (m; 1H); 1.86-1.63 (m; 2H); 1.53 (s; 4H); 1.38-1.18 (m; 3H); 1.08-0.93 (m; 9H); 0.92-0.68 (m; 27H).

HRMS (ESI): neutral mass calculated for $C_{87}H_{121}Br_4N_{15}O_{16}$ [M]:1947.5849; observed 1947.5891.

Example 24: 2-(2-(2-(2-(4-(methyltetrazinylphenoxy)ethoxy)ethoxy)ethoxy)-ethyl)carbamoylpropane-1,3-diyl(2,6-bis(bromomethyl)isonicotinamide) (34)

(34)

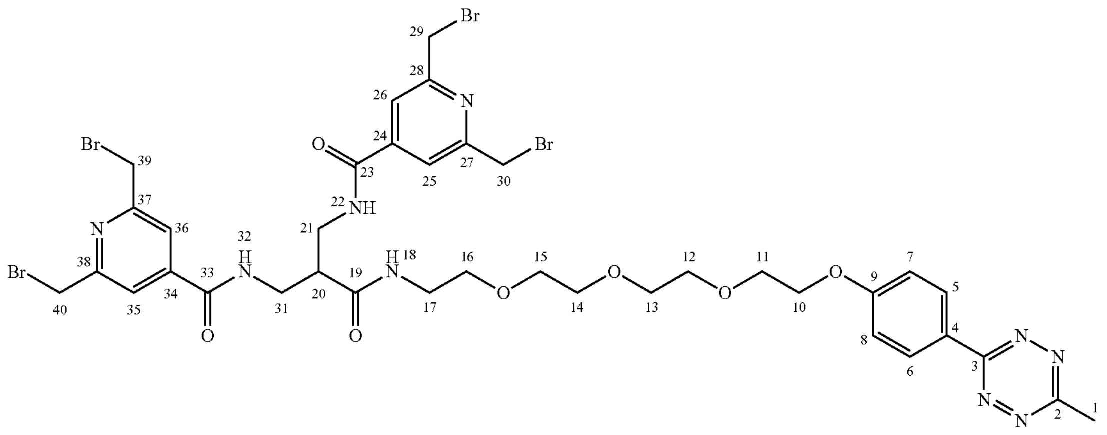

Under an inert atmosphere, in the dark and under anhydrous conditions, 3-(2,6-bis(bromomethyl)isonicotinamido)-2-((2,6-bis(bromomethyl)isonicotinamido)methyl)-propanoic acid (17) (11.5 mg; 0.016 mmol; 2.2 eq) was suspended in anhydrous MeCN (1.1 mL) then EEDQ (32.5 mg; 0.131 mmol; 17.5 eq) was added. The activation medium was stirred under argon at 25° C. for 30 min. A solution of 4-methyltetrazinylphenoxy-3,6,9,12-tetraoxa-pentadecan-15-amine (3.0 mg; 0.008 mmol; 1.0 eq), dissolved in anhydrous DMF (1 mL) in the presence of anhydrous DIPEA (13.1 μL; 0.075 mmol; 10.0 eq), was added to the activation medium. The reaction medium obtained was stirred under argon at 25° C. for 1 hour. The mixture was purified by semi-preparative high-pressure liquid chromatography ($t_R$=24.85 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% B over 32 min then 100% B over 6 min at 17.1 mL/min) to give (34) (4.4 mg; 54%) in the form of a pink lyophilisate.

$^1$H NMR (300 MHz, $CD_3OD$) δ 8.44 (d; J=9.0 Hz, $2H_{5,6}$); 7.83 (s; $4H_{25,26,35,36}$); 7.11 (d; J=9.0 Hz; $2H_{7,8}$); 4.63 (s; $8H_{29,30,39,40}$); 4.21 (m; $2H_{10}$); 3.64 (m; $2H_{11}$); 3.38-3.67 (m; $21H_{12,13,14,15,16,17,20,21,31}$); 3.01 (s, $3H_1$).

HRMS (ESI): m/z calculated for $C_{37}H_{44}Br_4N_9O_7$ $[M+H]^+$: 1042.0088; observed 1042.0090.

Example 25: MMAE 1-trans-cyclooctenyl-1-oxo-5,8,11,14-tetraoxa-2-azahetaptadecan-17-amide-valine-citrulline-p-aminobenzoyl carbamate (35)

(35)

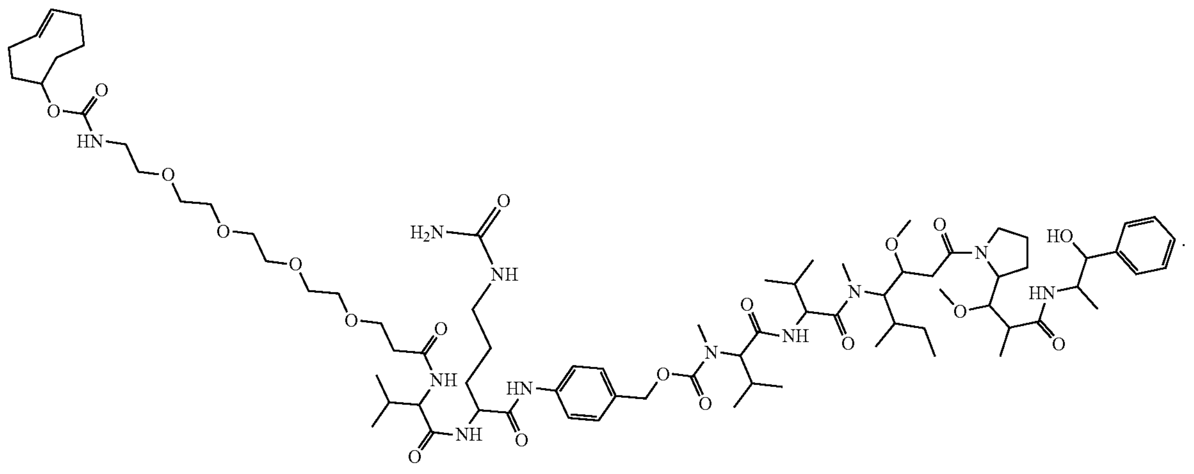

1-trans-cyclooctenyl-1-oxo-5,8,11,14-tetraoxa-2-azahetaptadecan-17-oic acid (5.5 mg; 0.013 mmol; 1.6 eq) was dissolved in anhydrous DMF (200 μL). The reaction medium was cooled to 0° C., then HATU (12.7 mg; 0.033 mmol; 4.1 eq) and 2,6-lutidine (5.6 μL; 0.049 mmol; 5.2 eq) were added. The activation solution was stirred under argon at 0° C. for 15 min. A solution of MMAE valine-citrulline-p-aminobenzoyl carbamate trifluoroacetic acid salt (10.0 mg; 0.008 mmol; 1.0 eq), solubilized in anhydrous DMF (200 μL), was added to the activation medium. The reaction medium was placed under stirring, under argon at RT for 16 h. The mixture was purified by semi-preparative high-pressure liquid chromatography ($t_R$=23.51 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% B over 32 min then 100% B over 6 min at 17.1 mL/min) to give (35) (11.1 mg; 95%) in the form of a white lyophilisate.

$^1$H NMR (300 MHz, $CD_3OD$) δ 7.61 (d; 2H); 7.21-7.40 (m; 10H); 5.34-5.55 (m; 6H); 5.16-5.18 (m; 2H); 4.49-4.55 (m; 6H); 4.17-4.26 (m; 6H); 3.73-3.77 (m; 4H); 3.49-3.55 (m; 4H); 3.08-3.11 (m; 3H); 2.92-2.95 (m; 5H); 2.46-2.57 (m; 5H); 2.32-2.35 (m; 3H); 1.67-2.28 (m; 21H); 1.34-1.59 (m; 6H); 1.17-1.29 (m; 6H); 1.13-1.16 (m; 8H); 0.85-0.97 (m; 25H)

HRMS (ESI): neutral mass calculated for $C_{78}H_{27}N_{11}O_{19}$ [M]: 1521.9310; observed 1521.9261.

Example 26: Trastuzumab—Compound (34) Conjugate

Reagents

Bioconjugation buffer 1, 5 mg/mL trastuzumab in bioconjugation buffer, reducing agent 1 (7.0 eq), compound (34) (10.6 eq) at a concentration of 1 mM in a mixture of 80% DMF and 20% MeOH.

Method

Bioconjugation reaction 2.

Denaturing HRMS Analysis According to Method 2

The results are shown in Table 29 below.

TABLE 29

| | LHHL | | LH | |
|---|---|---|---|---|
| | Intensity (%) | MM (Da)[1] | Intensity (%) | MM (Da)[1] |
| MAR 0 | n.o.[2] | | 23 | 72586 |
| MAR 1 | 100 | 145895 | 77 | 73312 |
| MAR 2 | n.o.[2] | | n.o.[2] | |
| MAR 3 | n.o.[2] | | n.o.[2] | |
| Average MAR | 1.00 | | 0.77 | |

[1]molecular mass of the deglycosylated species
[2]not observed

HRMS analysis allowed determining an average MAR of 1.00 for LHHL species and 0.77 for LH species. LHH, HH, H and L species were not observed.

SDS-PAGE Gel Analysis Under Denaturing Non-Reducing and Reducing Conditions

The results are shown in Table 30 below.

TABLE 30

| Species | DTT | LHHL | LHH | HH | LH | H | L |
|---|---|---|---|---|---|---|---|
| Optical density (%) | − | 96 | n.o.[1] | n.o.[1] | 4 | n.o.[1] | n.o.[1] |
| | + | 61 | n.o.[1] | n.o.[1] | 12 | 10 | 16 |

[1]not observed

Analysis on SDS-PAGE gel allowed determining under reducing conditions a reconstruction of 61% and under non-reducing conditions an average MAR of 1.02.

Example 27: Trastuzumab—Compound (34)—Compound (35) Conjugate

Reagents

Bioconjugation buffer 1, 5 mg/mL trastuzumab in bioconjugation buffer, reducing agent 1, compound (34) (1$^{st}$ compound) (10.6 eq) at a concentration of 1 mM in a mixture of 80% DMF and 20% MeOH, compound (35) ($2^{nd}$ compound) (11.7 eq) at a concentration of 10 mM in DMSO.

Method

Bioconjugation reaction 3.

Denaturing HRMS Analysis According to Method 2

The results are shown in Table 31 below.

TABLE 31

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | 100 | 147391 | 100 | 74804 |
| MAR 2 | n.o.[2] | | n.o.[2] | |
| MAR 3 | n.o.[2] | | n.o.[2] | |
| Average MAR | 1.00 | | 1.00 | |

[1]molecular mass of the deglycosylated species
[2]not observed

HRMS analysis allowed determining an average MAR of 1.00 for LHHL species and an average MAR of 1.00 for LH species. LHH, HH, H and L species were not observed. The mass increment is correct.

SDS-PAGE Gel Analysis in Denaturing Non-Reducing and Reducing Conditions

The results are shown in Table 32 below.

TABLE 32

| Species | DTT | LHHL | LHH | HH | LH | H | L |
|---|---|---|---|---|---|---|---|
| Optical density (%) | − | 84 | n.o.[1] | n.o.[1] | 6 | n.o.[1] | 10 |
| | + | 58 | n.o.[1] | n.o.[1] | 10 | 17 | 15 |

[1]not observed

Analysis on SDS-PAGE gel allowed determining under reducing conditions a reconstruction of 58% and under non-reducing conditions an average MAR of 1.07.

Example 28: Trastuzumab—Compound (34) Conjugate

Reagents

Bioconjugation buffer 1, 5 mg/mL trastuzumab in bioconjugation buffer, reducing agent 1 (8.0 eq), compound (34) (12.0 eq) at a concentration of 3 mM in a mixture of 20% DMF and 80% MeOH.

Method

Bioconjugation reaction 1.

Denaturing HRMS Analysis According to Method 2

The results are shown in Table 33 below.

TABLE 33

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 100 | 74755 |
| MAR 2 | 100 | 149517 | n.o.[2] | |
| MAR 3 | n.o.[2] | | n.o.[2] | |
| Average MAR | 2.00 | | 1.00 | |

[1]molecular mass of the non-deglycosylated species
[2]not observed

HRMS analysis allowed determining an average MAR of 2.00 for LHHL species and 1.00 for LH species. LHH, HH, H and L species were not observed.

SDS-PAGE Gel Analysis Under Denaturing Non-Reducing and Reducing Conditions

The results are shown in Table 34 below.

TABLE 34

| Species | DTT | LHHL | LHH | HH | LH | H | L |
|---|---|---|---|---|---|---|---|
| Optical density (%) | − | 70 | n.o.[1] | n.o.[1] | 30 | n.o.[1] | n.o.[1] |
| | + | 66 | n.o.[1] | n.o.[1] | 28 | n.o.[1] | 6 |

[1]not observed

Analysis on SDS-PAGE gel allowed determining under reducing conditions a reconstruction of 66% and under non-reducing conditions an average MAR of 2.00.

Example 29: Trastuzumab—Compound (34)—Compound (35) Conjugate

Reagents

Bioconjugation buffer 1, 5 mg/mL trastuzumab in bioconjugation buffer, reducing agent 1, compound (34) ($1^{st}$ compound) (8.0 eq) at a concentration of 3 mM in a mixture of 20% DMF and 80% MeOH, compound (35) ($2^{nd}$ compound) (8.8 eq) at a concentration of 10 mM in DMSO.

Method

Bioconjugation reaction 3.

Denaturing HRMS Analysis According to Method 2

The results are shown in Table 35 below.

TABLE 35

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 100 | 74805 |
| MAR 2 | 100 | 149610 | n.o.[2] | |
| MAR 3 | n.o.[2] | | n.o.[2] | |
| Average MAR | 2.00 | | 1.00 | |

[1]molecular mass of the deglycosylated species
[2]not observed

HRMS analysis allowed determining an average MAR of 2.00 for LHHL species and an average MAR of 1.00 for LH species. LHH, HH, H and L species were not observed.

SDS-PAGE Gel Analysis Under Denaturing Non-Reducing Conditions

The results are shown in Table 36 below.

TABLE 36

| Species | DTT | LHHL | LHH | HH | LH | H | L |
|---|---|---|---|---|---|---|---|
| Optical density (%) | − | 75 | n.o.[1] | n.o.[1] | 25 | n.o.[1] | n.o.[1] |
| | + | 69 | n.o.[1] | n.o.[1] | 26 | n.o.[1] | 5 |

[1]not observed

Analysis on SDS-PAGE gel allowed determining under reducing conditions a reconstruction of 69% and under non-reducing conditions an average MAR of 2.00.

Example 30: 2-(2-(2-(trans-cyclooctenylcarbamoyl)ethoxy)ethoxy)ethyl)-carbamoylpropane-1,3-diyl(2,6-bis(bromomethyl)isonicotinamide) (36)

(36)

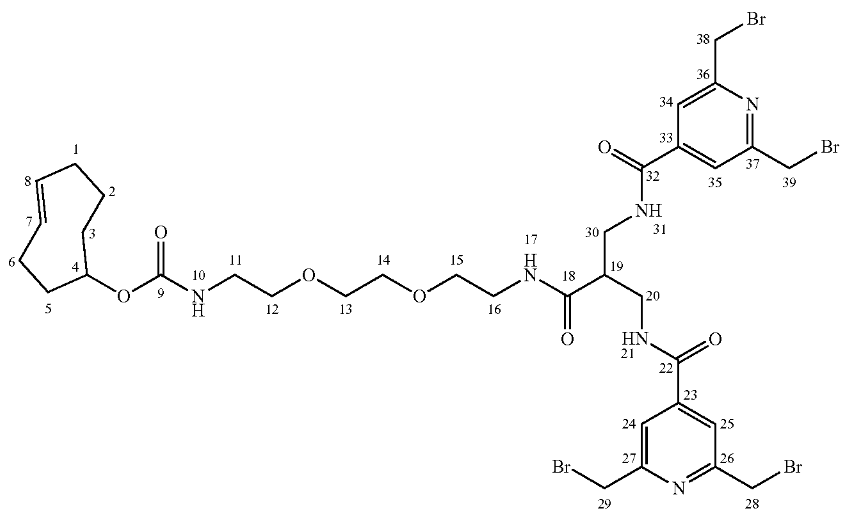

Under an inert atmosphere, in the dark and under anhydrous conditions, 3-(2,6-bis(bromomethyl)isonicotinamido)-2-((2,6-bis(bromomethyl)isonicotinamido)methyl)-propanoic acid (17) (14.7 mg; 0.021 mmol; 2.2 eq) was suspended in anhydrous MeCN (1.4 mL) then EEDQ (39.2 mg; 0.159 mmol; 16.4 eq) was added. The activation medium was stirred under argon at 25° C. for 30 min. A solution of trans-cyclooctenyl(2-(2-(2-aminoethoxy)ethoxy)ethyl)carbamate (2.9 mg; 0.010 mmol; 1.0 eq), dissolved in anhydrous DMF (1.25 mL) in the presence of anhydrous DIPEA (17.0 μL; 0.098 mmol; 10.1 eq), was added to the activation medium. The reaction medium obtained was stirred under argon at 25° C. for 1 h. The mixture was purified by semi-preparative high-pressure liquid chromatography ($t_R$=37.49 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% B over 32 min then 100% B over 6 min at 17.1 mL/min) to give (36) (5.1 mg; 54%) in the form of a white lyophilisate.

$^1$H NMR (300 MHz, $CD_3OD$) δ 7.83 (s; $4H_{24,25,34,35}$); 5.35-5.60 (m; $2H_{7,8}$); 4.6 (s; $8H_{28,29,38,39}$); 4.23 (m; $1H_4$); 3.14-3.65 (m; $17H_{11,12,13,14,15,16,19,20,30}$); 1.44-1.92 (m, $10H_{1,2,3,5,6}$).

HRMS (ESI): m/z calculated for $C_{35}H_{47}Br_4N_6O_7$ $[M+H]^+$: 979.0234; observed 979.0229.

Example 31: MMAE 4-methyleteatrazinylphenoxy-3,6,9,12-tetraoxapentadecan-15-amide-valine-citrulline-p-aminobenzoyl carbamate (37)

(37)

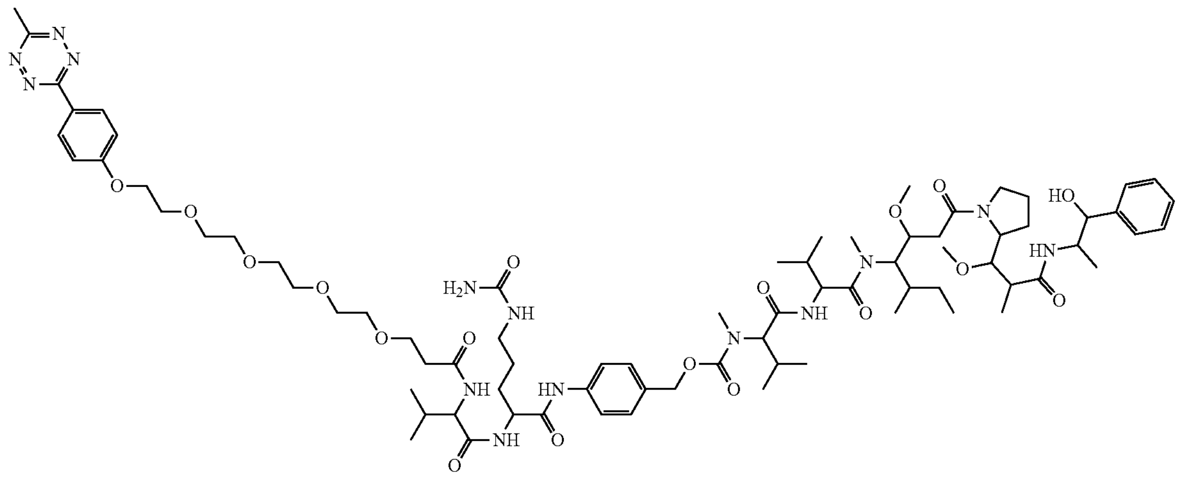

4-Methyleteatrazinylphenoxy-3,6,9,12-tetraoxapentadecan-15-oic acid (4.5 mg; 0.011 mmol; 1.3 eq) was dissolved in anhydrous DMF (200 μL). The reaction medium was cooled to 0° C., then HATU (12.2 mg; 0.032 mmol; 3.9 eq) and 2,6-lutidine (5.6 μL; 0.049 mmol; 6.0 eq) were added. The activation solution was stirred under argon at 0° C. for 15 min. A solution of MMAE valine-citrulline-p-aminobenzoyl carbamate trifluoroacetic acid salt (10.1 mg; 0.008 mmol; 1.0 eq), solubilized in anhydrous DMF (200 μL), was added to the activation medium. The reaction medium was placed under stirring, under argon at RT for 16 h. The mixture was purified by semi-preparative high-pressure liquid chromatography ($t_R$=23.21 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% B over 32 min then 100% B over 6 min at 17.1 mL/min) to give (37) (7.1 mg; 56%) in the form of a pink lyophilisate.

$^1$H NMR (300 MHz, $CD_3OD$) δ 8.51 (d; 2H); 7.61 (d; 2H); 7.31-7.39 (m; 7H); 7.18 (d; 2H); 4.20-4.28 (m; 6H); 3.90 (m, 2H); 3.56-3.74 (m; 17H); 2.93-2.96 (m; 4H); 2.47-2.55 (m; 7H); 1.60-2.23 (m; 18H); 1.50-1.60 (m; 4H); 1.31-1.42 (m; 10H); 1.12-1.19 (m; 7H); 0.88-0.99 (m; 32H) HRMS (ESI): m/z calculated for $C_{78}H_{122}N_{14}O_{18}$ [M+2H] $^{2}$+: 771.4525; observed 771.4524.

Example 32: Trastuzumab—Compound (36) Conjugate

Reagents

Bioconjugation buffer 1, 5 mg/mL trastuzumab in bioconjugation buffer, reducing agent 1 (7.0 eq), compound (36) (3.0 eq) at a concentration of 0.25 mM in a mixture of 80% DMF and 20% MeOH.

Method

Bioconjugation reaction 2.

Denaturing HRMS Analysis According to Method 2

The results are shown in Table 37 below.

TABLE 37

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | 82% | 148726 | 100% | 74692 |
| MAR 2 | 18% | 149387 | n.o.[2] | |
| MAR 3 | n.o.[2] | | n.o.[2] | |
| Average MAR | 1.18 | | 1.0 | |

[1]molecular mass of the non-deglycosylated species
[2]not observed

HRMS analysis allowed determining an average MAR of 1.18 for LHHL species and 1.0 for LH species. LHH, HH, H and L species were not observed.

SDS-PAGE Gel Analysis Under Denaturing Non-Reducing and Reducing Conditions

The results are shown in Table 38 below.

TABLE 38

| Species | DTT | LHHL | LHH | HH | LH | H | L |
|---|---|---|---|---|---|---|---|
| Optical density (%) | − | 79 | n.o.[1] | n.o.[1] | 5 | n.o.[1] | 16 |
| | + | 66 | n.o.[1] | n.o.[1] | 21 | 3 | 10 |

[1]not observed

Analysis on SDS-PAGE gel allowed determining under reducing conditions a reconstruction of 66% and under non-reducing conditions an average MAR of 1.23.

Example 33: Trastuzumab—Compound (36)—Compound (37) Conjugate

Reagents

Bioconjugation buffer 1, 5 mg/mL trastuzumab in bioconjugation buffer, reducing agent 1, compound (36) (1$^{st}$ compound) (3.0 eq) at a concentration of 0.25 mM in a mixture of 80% DMF and 20% MeOH, compound (37) (2$^{nd}$ compound) (3.3 eq) at a concentration of 10 mM in DMSO.

Method

Bioconjugation reaction 3.

Denaturing HRMS Analysis According to Method 2

The results are shown in. Table 39 below.

TABLE 39

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | 80% | 150241 | 100% | 76206 |
| MAR 2 | 20% | 152421 | n.o.[2] | |
| MAR 3 | n.o.[2] | | n.o.[2] | |
| Average MAR | 1.20 | | 1.00 | |

[1]molecular mass of the non-deglycosylated species
[2]not observed

HRMS analysis allowed determining an average MAR of 1.20 for the LHHL species and an average MAR of 1.00 for the LH species. LHH, HH, H and L species were not observed.

SDS-PAGE Gel Analysis Under Denaturing Non-Reducing Conditions

The results are shown in Table 40 below.

TABLE 40

| Species | DTT | LHHL | LHH | HH | LH | H | L |
|---|---|---|---|---|---|---|---|
| Optical density (%) | − | 81 | n.o.[1] | n.o.[1] | 14 | n.o.[1] | 5 |
| | + | 63 | n.o.[1] | n.o.[1] | 25 | n.o.[1] | 12 |

[1]not observed

Analysis on SDS-PAGE gel allowed determining under reducing conditions a reconstruction of 63% and under non-reducing conditions an average MAR of 1.32.

Example 34: Panitumumab—Compound (36) Conjugate

Reagents

Bioconjugation Buffer 1, 5 mg/mL panitumumab in bioconjugation buffer, reducing agent 1 (10.6 eq), compound (36) (18.0 eq) at a concentration of 3 mM in a mixture of 20% DMF and 80% MeOH.

Method

Bioconjugation reaction 1.

Denaturing HRMS Analysis According to Method 2

The results are shown in Table 41 below.

TABLE 41

| | LHHL | | LH | |
|---|---|---|---|---|
| | Intensity (%) | MM (Da)[1] | Intensity (%) | MM (Da)[1] |
| MAR 0 | 2% | 146942 | n.o.[2] | |
| MAR 1 | 98% | 147602 | 100 | 74137 |
| MAR 2 | n.o.[2] | | n.o.[2] | |
| MAR 3 | n.o.[2] | | n.o.[2] | |
| Average MAR | 0.98 | | 1.00 | |

[1]molecular mass of the non-deglycosylated species
[2]not observed

HRMS analysis allowed determining an average MAR of 0.98 for LHHL species and 1.00 for LH species. LHH, HH, H and L species were not observed.

SDS-PAGE Gel Analysis in Denaturing Non-Reducing and Reducing Conditions

The results are shown in Table 42 below.

TABLE 42

| Species | DTT | LHHL | LHH | HH | LH | H | L |
|---|---|---|---|---|---|---|---|
| Optical | − | 97 | n.o.[1] | n.o.[1] | 3 | n.o.[1] | n.o.[1] |
| density (%) | + | 61 | n.o.[1] | n.o.[1] | 39 | n.o.[1] | n.o.[1] |

[1]not observed

Analysis on SDS-PAGE gel allowed determining under reducing conditions a reconstruction of 61% and under non-reducing conditions an average MAR of 1.01.

Example 35: Trastuzumab—Compound (36) Conjugate

Reagents

Bioconjugation buffer 1, 5 mg/mL trastuzumab in bioconjugation buffer, reducing agent 1 (8.0 eq), compound (36) (12.0 eq) at a concentration of 3 mM in a mixture of 30% DMF and 70% MeOH.

Method

Bioconjugation reaction 1.

Denaturing HRMS Analysis According to Method 2

The results are shown in Table 43 below.

TABLE 43

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 100 | 74692 |
| MAR 2 | 100 | 149389 | n.o.[2] | |
| MAR 3 | n.o.[2] | | n.o.[2] | |
| Average MAR | 2.00 | | 1.00 | |

[1]molecular mass of the non-deglycosylated species
[2]not observed

HRMS analysis allowed determining an average MAR of 2.00 for LHHL species and 1.00 for LH species. LHH, HH, H and L species were not observed.

SDS-PAGE Gel Analysis Under Denaturing Non-Reducing and Reducing Conditions

The results are shown in Table 44 below.

TABLE 44

| Species | DTT | LHHL | LHH | HH | LH | H | L |
|---|---|---|---|---|---|---|---|
| Optical | − | 64 | n.o.[1] | n.o.[1] | 31 | n.o.[1] | 5 |
| density (%) | + | 60 | n.o.[1] | n.o.[1] | 38 | n.o.[1] | 2 |

[1]not observed

Analysis on SDS-PAGE gel allowed determining under reducing conditions a reconstruction of 60% and under non-reducing conditions an average MAR of 2.00.

Example 36: Trastuzumab—Compound (36)—Compound (37) Conjugate

Reagents

Bioconjugation buffer 1, 5 mg/mL trastuzumab in bioconjugation buffer, reducing agent 1 (8.0 eq), compound (36) ($1^{st}$ compound) (12.0 eq) at a concentration of 3 mM in a mixture of 30% DMF and 70% MeOH, compound (37) ($2^{nd}$ compound) (13.2 eq) at a concentration of 10 mM in DMSO.

Method

Bioconjugation reaction 4.

Denaturing HRMS Analysis According to Method 2

The results are shown in Table 45 below.

TABLE 45

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 100 | 76208 |
| MAR 2 | 100 | 152418 | n.o.[2] | |
| MAR 3 | n.o.[2] | | n.o.[2] | |
| Average MAR | 2.00 | | 1.00 | |

[1]molecular mass of the non-deglycosylated species
[2]not observed

HRMS analysis allowed determining an average MAR of 2.00 for LHHL species and an average MAR of 1.00 for LH species. LHH, HH, H and L species were not observed.

SDS-PAGE Gel Analysis Under Denaturing Non-Reducing and Reducing Conditions

The results are shown in Table 46 below.

TABLE 46

| Species | DTT | LHHL | LHH | HH | LH | H | L |
|---|---|---|---|---|---|---|---|
| Optical | − | 66 | n.o.[1] | n.o.[1] | 34 | n.o.[1] | n.o.[1] |
| density (%) | + | 62 | n.o.[1] | n.o.[1] | 33 | n.o.[1] | 5 |

[1]not observed

Analysis on SDS-PAGE gel allowed determining under reducing conditions a reconstruction of 62% and under non-reducing conditions an average MAR of 2.00.

Example 37: 4-{2-azatricyclo[10.4.0.04-9]hexadeca-1(12),4(9),5,7,13,15-hexaen-10-yn-2-yl}-N-(2-{2-[2-(3-{[2,6-bis(bromomethyl)pyridin-4-yl]formamido}-2-({[2,6-bis(bromomethyl)pyridin-4-yl]formamido}methyl)-propanamido)ethoxy]ethoxy}ethyl)-4-oxobutanamide (38)

(38)

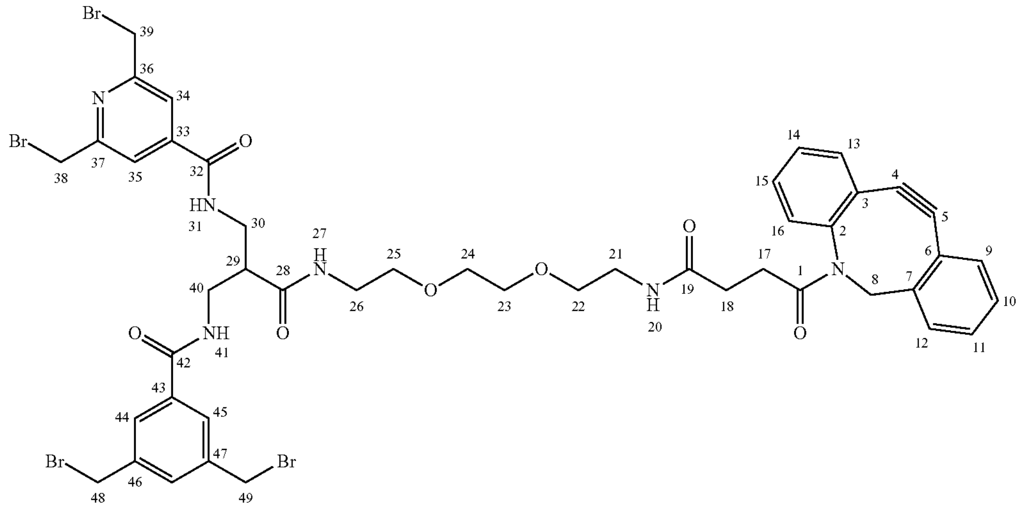

Under an inert atmosphere, in the dark and under anhydrous conditions, 3-(2,6-bis(bromomethyl)isonicotinamido)-2-((2,6-bis(bromomethyl)isonicotinamido)methyl)-propanoic acid (17) (17.7 mg; 0.025 mmol; 2.1 eq) was suspended in anhydrous MeCN (1.69 mL) then EEDQ (48.2 mg; 0.195 mmol; 16.5 eq) was added. The activation medium was stirred under argon at 25° C. for 30 min. A solution of N-{2-[2-(2-aminoethoxy)ethoxy]ethyl}-4-{2-azatricyclo[10.4.0.0$^{4,9}$]hexadeca-1(12),4(9),5,7,13,15-hexaen-10-yn-2-yl}-4-oxobutanamide (6.5 mg; 0.012 mmol; 1.0 eq), dissolved in anhydrous DMF (1.43 mL) in the presence of anhydrous DIPEA (20.8 μL; 0.119 mmol; 10.1 eq), was added to the activation medium. The reaction medium obtained was stirred under argon at 25° C. for 1 h. The mixture was purified by semi-preparative high-pressure liquid chromatography ($t_R$=34.84 min; on the Gilson PLC 2050 system [ARMEN V2 (pump) and ECOM TOY-DAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% B over 32 min then 100% B over 6 min at 17.1 mL/min) to give (38) (5.1 mg; 36%) in the form of a white lyophilisate.

$^1$H NMR (300 MHz, $CD_3OD$) δ 8.83 (t; J=5.7 Hz; 1H); 8.12 (t; J=5.5 Hz; 1H); 7.81 (s; 4H); 7.65-7.52 (m; 2H); 7.48-7.40 (m; 2H); 7.35-7.18 (m; 3H); 5.10 (d; J=14.0 Hz; 1H); 4.63 (s; 8H); 3.68 (d; J=13.9 Hz; 1H); 3.64-3.56 (m; 4H); 3.54-3.42 (m, 4H); 3.43-3.33 (m; 6H); 3.18 (m; 2H); 3.02 (p; J=6.0 Hz; 1H); 2.68 (dt, J=16.2 and 7.4 Hz; 1H); 2.43-2.28 (m; 1H); 2.25-2.11 (m; 1H); 2.06-1.91 (m; 1H).

HRMS (ESI): m/z calculated for $C_{45}H_{48}Br_4N_7O_7[M+H]^+$: 1114.0343; observed 1114.0351.

Example 38: Trastuzumab—Compound (38) Conjugate

Reagents

Bioconjugation buffer 1, 5 mg/mL trastuzumab in bioconjugation buffer, reducing agent 1 (7.0 eq), compound (38) (10.6 eq) at a concentration of 1 mM in a mixture of 80% DMF and 20% MeOH.

Method

Bioconjugation reaction 2.

Denaturing HRMS Analysis According to Method 2

The results are shown in Table 47 below.

TABLE 47

| | LHHL | |
|---|---|---|
| | Intensity (%) | MM (Da)[1] |
| MAR 0 | n.o.[2] | |
| MAR 1 | 93 | 146051 |
| MAR 2 | 7 | 146830 |
| MAR 3 | n.o.[2] | |
| Average MAR | 1.07 | |

[1]molecular mass of the deglycosylated species

[2]not observed

HRMS analysis allowed determining an average MAR of 1.07 for the LHHL species. LHH, HH, LH, H and L species were not observed.

SDS-PAGE Gel Analysis Under Denaturing Non-Reducing and Reducing Conditions

The results are shown in Table 48 below.

TABLE 48

| Species | DTT | LHHL | LHH | HH | LH | H | L |
|---|---|---|---|---|---|---|---|
| Optical | – | 95 | n.o.[1] | n.o.[1] | n.o.[1] | n.o.[1] | 5 |
| density (%) | + | 93 | n.o.[1] | n.o.[1] | n.o.[1] | n.o.[1] | 7 |

[1]not observed

Analysis on SDS-PAGE gel allowed determining under reducing conditions a reconstruction of 93% and under non-reducing conditions an average MAR of 1.07.

Example 39: Trastuzumab—Compound (38)—Compound (22) Conjugate

Reagents

Bioconjugation buffer 1, 5 mg/mL trastuzumab in bioconjugation buffer, reducing agent 1, compound (38) (1$^{st}$ compound) (10.6 eq) at a concentration of 1 mM in a mixture of 80% DMF and 20% MeOH, compound (22) (2$^{nd}$ compound) (11.7 eq) at a concentration of 10 mM in DMSO.

Method

Bioconjugation reaction 3.

Denaturing HRMS Analysis According to Method 2

The results are shown in Table 49 below.

TABLE 49

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | 100 | 147233 | 100 | 74645 |
| MAR 2 | n.o.[2] | | n.o.[2] | |
| MAR 3 | n.o.[2] | | n.o.[2] | |
| Average MAR | 1.00 | | 1.00 | |

[1]molecular mass of the deglycosylated species
[2]not observed

HRMS analysis allowed determining an average MAR of 1.00 for LHHL species and an average MAR of 1.00 for LH species. LHH, HH, H and L species were not observed.

SDS-PAGE Gel Analysis Under Denaturing Non-Reducing and Reducing Conditions

The results are shown in Table 50 below.

TABLE 50

| Species | DTT | LHHL | LHH | HH | LH | H | L |
|---|---|---|---|---|---|---|---|
| Optical | – | 87 | n.o.[1] | n.o.[1] | n.o.[1] | 7 | 6 |
| density (%) | + | 77 | n.o.[1] | n.o.[1] | 14 | 1 | 8 |

[1]not observed

Analysis on SDS-PAGE gel allowed determining under reducing conditions a reconstruction of 77% and under non-reducing conditions an average MAR of 1.00.

Example 40: Trastuzumab—Compound (38)—Commercial Compound AF488 Conjugate

Reagents

Bioconjugation buffer 1, 5 mg/mL trastuzumab in bioconjugation buffer, reducing agent 1, compound (38) (1st compound) (10.6 eq) at a concentration of 1 mM in a mixture of 80% DMF and 20% MeOH, commercial compound (AF488, marketed by ThermoFisher Scientific) (2$^{nd}$ compound) (11.7 eq) at a concentration of 10 mM in DMSO.

(AF488)

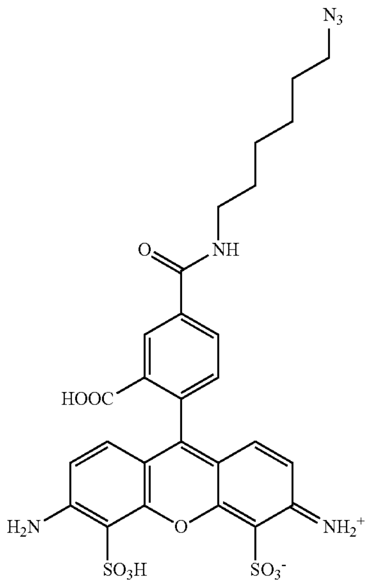

Method

Bioconjugation reaction 3.

Denaturing HRMS Analysis According to Method 2

The results are shown in Table 51 below.

TABLE 51

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | 73 | 149521 | 100 | 75486 |
| MAR 2 | 27 | 150978 | n.o.[2] | |
| MAR 3 | n.o.[2] | | n.o.[2] | |
| Average MAR | 1.27 | | 1.00 | |

[1]molecular mass of the non-deglycosylated species
[2]not observed

HRMS analysis allowed determining an average MAR of 1.27 for LHHL species and an average MAR of 1.00 for LH species. LHH, HH, H and L species were not observed.

SDS-PAGE Gel Analysis Under Denaturing Non-Reducing and Reducing Conditions

The results are shown in Table 52 below.

TABLE 52

| Species | DTT | LHHL | LHH | HH | LH | H | L |
|---|---|---|---|---|---|---|---|
| Optical | – | 98 | n.o.[1] | n.o.[1] | 2 | n.o.[1] | n.o.[1] |
| density (%) | + | 94 | n.o.[1] | n.o.[1] | 6 | n.o.[1] | n.o.[1] |

[1]not observed

Analysis on SDS-PAGE gel allowed determining under reducing conditions a reconstruction of 94% and under non-reducing conditions an average MAR of 1.28.

Example 41: Trastuzumab—Compound (38) Conjugate

Reagents

Bioconjugation buffer 1, 5 mg/mL trastuzumab in bioconjugation buffer, reducing agent 1 (7.0 eq), compound (38) (12.0 eq) at a concentration of 3 mM in a mixture of 20% DMF and 80% MeOH.

Method

Bioconjugation reaction 2.

Denaturing HRMS Analysis According to Method 2

The results are shown in Table 53 below.

TABLE 53

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 100 | 73392 |
| MAR 2 | 100 | 146789 | n.o.[2] | |
| MAR 3 | n.o.[2] | | n.o.[2] | |
| Average MAR | 2.00 | | 1.00 | |

[1]molecular mass of the deglycosylated species
[2]not observed

HRMS analysis allowed determining an average MAR of 2.00 for LHHL species and 1.00 for LH species. LHH, HH, H and L species were not observed.

SDS-PAGE Gel Analysis Under Denaturing Non-Reducing and Reducing Conditions

The results are shown in Table 54 below.

TABLE 54

| Species | DTT | LHHL | LHH | HH | LH | H | L |
|---|---|---|---|---|---|---|---|
| Optical | − | 86 | n.o.[1] | n.o.[1] | 14 | n.o.[1] | n.o.[1] |
| density (%) | + | 84 | n.o.[1] | n.o.[1] | 16 | n.o.[1] | n.o.[1] |

[1]not observed

Analysis on SDS-PAGE gel allowed determining under reducing conditions a reconstruction of 84% and under non-reducing conditions an average MAR of 2.00.

Example 42: Trastuzumab—Compound (38)—Compound (22) Conjugate

Reagents

Bioconjugation buffer 1, 5 mg/mL trastuzumab in bioconjugation buffer, reducing agent 1, compound (38) (1st compound) (12.0 eq) at a concentration of 3 mM in a mixture of 20% DMF and 80% MeOH, compound (22) ($2^{nd}$ compound) (13.2 eq) at a concentration of 10 mM in DMSO.

Method

Bioconjugation reaction 3.

Denaturing HRMS Analysis According to Method 2

The results are shown in Table 55 below.

TABLE 55

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 100 | 74649 |
| MAR 2 | 100 | 149324 | n.o.[2] | |
| MAR 3 | n.o.[2] | | n.o.[2] | |
| Average MAR | 2.00 | | 1.00 | |

[1]molecular mass of the deglycosylated species
[2]not observed

HRMS analysis allowed determining an average MAR of 2.00 for LHHL species and an average MAR of 1.00 for LH species. LHH, HH, H and L species were not observed.

SDS-PAGE Gel Analysis Under Denaturing Non-Reducing and Reducing Conditions

The results are shown in Table 56 below.

TABLE 56

| Species | DTT | LHHL | LHH | HH | LH | H | L |
|---|---|---|---|---|---|---|---|
| Optical | − | 86 | n.o.[1] | n.o.[1] | 14 | n.o.[1] | n.o.[1] |
| density (%) | + | 89 | n.o.[1] | n.o.[1] | 11 | n.o.[1] | n.o.[1] |

[1]not observed

Analysis on SDS-PAGE gel allowed determining under reducing conditions a reconstruction of 89% and under non-reducing conditions an average MAR of 2.00.

Example 43: N,N'-(2-((2-(2-(2-(2-azidoethoxy)ethoxy)ethoxy)ethyl)-carbamoyl)propane-1,3-diyl) bis(2,6-bis(bromomethyl)isonicotinamide) (39)

(39)

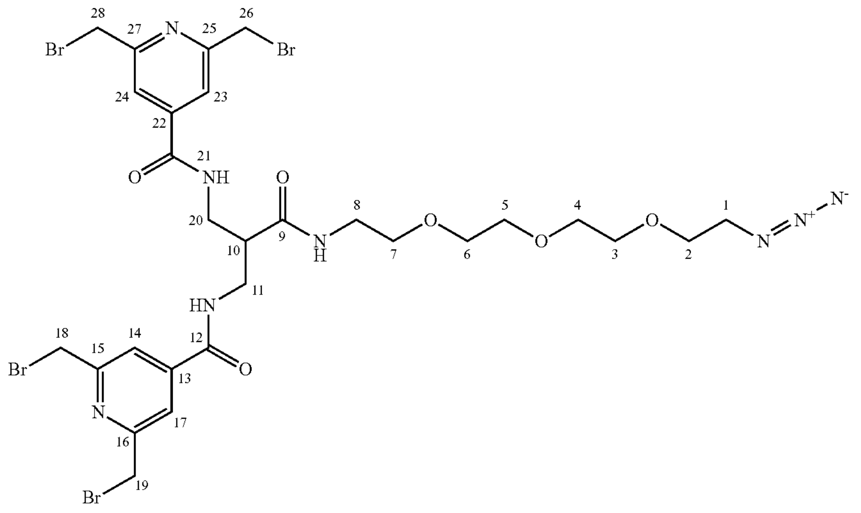

Under an inert atmosphere, in the dark and under anhydrous conditions, 3-(2,6-bis(bromomethyl)isonicotinamido)-2-((2,6-bis(bromomethyl)isonicotinamido)methyl)-propanoic acid (17) (15.6 mg; 0.022 mmol; 1.5 eq) was suspended in anhydrous MeCN (800 μL) then EEDQ (33.6 mg; 0.136 mmol; 9.3 eq) was added. The activation medium was stirred under argon at 25° C. for 30 min. A solution of 2-(2-(2-(2-azidoethoxy)ethoxy) ethoxy)ethan-1-amine (3.2 mg; 0.015 mmol; 1.0 eq), dissolved in anhydrous DMF (500 μL) in the presence of anhydrous DIPEA (20.0 μL; 0.115 mmol; 7.8 eq), was added to the activation medium. The reaction medium obtained was stirred under argon at 25° C. for 1 h. The mixture was purified by semi-preparative high-pressure liquid chromatography ($t_R$=26.18 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% B over 32 min then 100% B over 6 min at 17.1 mL/min) to give (39) (3.9 mg; 30%) in the form of a white lyophilisate.

$^1$H NMR (300 MHz, $CD_3OD$) δ 7.86 (s; $4H_{14,17,23,24}$); 4.97 (s; $8H_{18,19,26,28}$); 3.58-3.72 (m; $16H_{1,2,3,4,5,6,7,8}$); 3.43 (m; $2H_{11,20}$); 3.03 (m; $1H_{10}$).

HRMS (ESI): m/z calculated for $C_{25}H_{37}Br_4N_8O_6$ $[M+H]^+$: 896.9564; observed 896.9546.

Example 44: (4-{2-[2-(6-{2-azatricyclo[10.4.0.0$^{4,9}$] hexadeca-1(1$^2$),4(9),5,7,13,15-hexaen-10-yn-2-yl}-6-oxohexanamido)-3-methylbutanamido]-5-(carbamoylamino)pentanamido}phenyl)methyl N-{1-[(1-{[l-(2-{2-[(1-hydroxy-1-phenylpropan-2-yl)carbamoyl]-1-methoxy-2-methylethyl}pyrrolidin-1-yl)-3-methoxy-5-methyl-1-oxoheptan-4-yl](methyl) carbamoyl}-2-methylpropyl)carbamoyl]-2-methylpropyl}-N-methylcarbamate (40)

6-{2-azatricyclo[10.4.0.0$^4$-9]hexadeca-1(12),4(9),5,7,13,15-hexaen-10-yn-2-yl}-6-oxohexanoic acid (2.0 mg; 0.006 mmol; 1.5 eq) was dissolved in anhydrous DMF (100 μL). The reaction medium was stirred at RT, and HATU (3.0 mg; 0.008 mmol; 2.0 eq) and 2,6-lutidine (1.2 μL; 0.010 mmol; 2.5 eq) were added. The activation solution was stirred under argon at 21° C. for 10 min. A solution of MMAE valine-citrulline-p-aminobenzoyl carbamate trifluoroacetic acid salt (5.0 mg; 0.004 mmol; 1.0 eq), solubilized in anhydrous DMF (100 μL), was added to the activation medium. The reaction medium was stirred, under argon at RT for 1 h 30. The mixture was purified by semi-preparative high-pressure liquid chromatography ($t_R$=25.30 min; on the Gilson PLC 2050 system [ARMEN V2 (pump) and ECOM TOY-DAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% of B over 16 min then 100% of B over 4 min at 17.1 mL/min) to give (40) (3.3 mg; 57%) in the form of a white lyophilisate.

$^1$H NMR (300 MHz, $CD_3OD$) δ 9.14 (s; 1H); 7.61 (m; 3H); 7.39-7.50 (m; 12H); 6.26-6.65 (m; 2H); 4.85-4.95 (m; 4H); 4.63-4.85 (m; 2H); 4.15 (s; 1H); 3.99 (s; 3H); 3.83 (s; 1H); 3.64-3.71 (m; 2H); 3.39 (m; 7H); 2.75-3.30 (m; 16H); 2.17 (m; 2H); 2.04 (m; 3H); 1.49-2.02 (m; 13H); 1.35 (s; 4H); 1.24 (m; 5H); 0.77-1.22 (m; 32H).

HRMS (ESI): neutral mass calculated for $C_{79}H_{112}N_{11}O_{14}$ $[M+H]^+$: 1438.8335; observed 1438.8330.

Example 45: Trastuzumab—Compound (39) Conjugate

Reagents

Bioconjugation buffer 1, 5 mg/mL trastuzumab in bioconjugation buffer, reducing agent 2 (8.0 eq), compound (39) (12.0 eq) at a concentration of 3 mM in a mixture of 20% DMF and 80% MeOH.

(40)

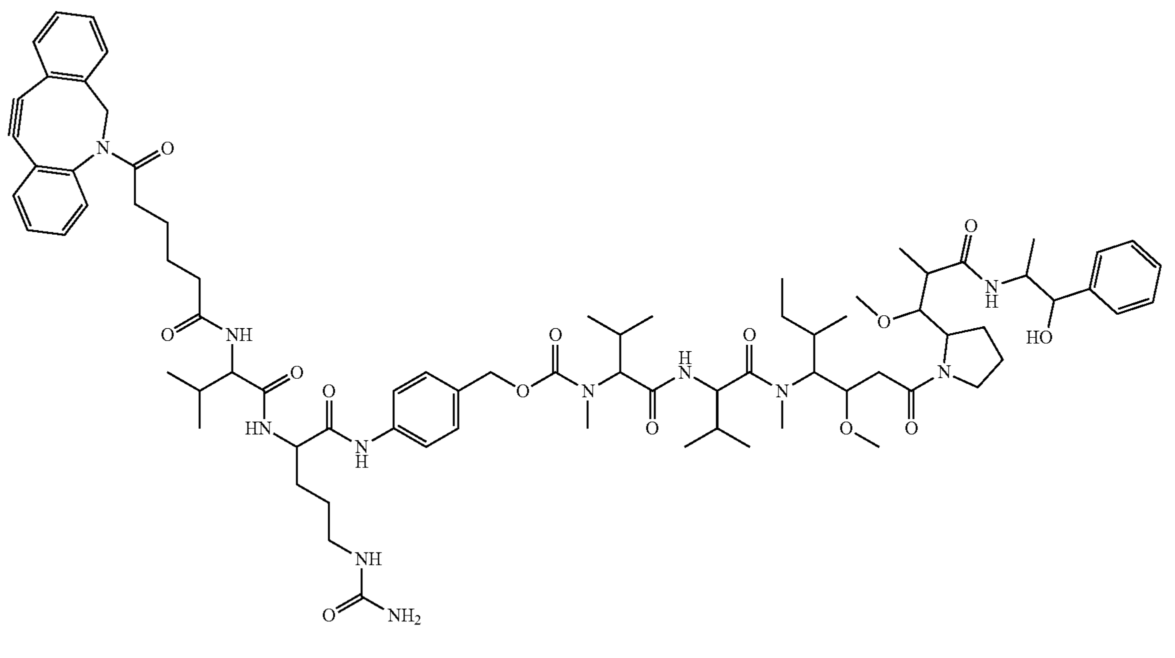

Method

Bioconjugation reaction 1.

Denaturing HRMS Analysis According to Method 2

The results are shown in Table 57 below.

TABLE 57

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 100 | 74610 |
| MAR 2 | 100 | 149228 | n.o.[2] | |
| MAR 3 | n.o.[2] | | n.o.[2] | |
| Average MAR | 2.00 | | 1.00 | |

[1]molecular mass of the non-deglycosylated species

[2]not observed

HRMS analysis allowed determining an average MAR of 2.00 for LHHL species and 1.00 for LH species. LHH, HH, H and L species were not observed.

SDS-PAGE Gel Analysis Under Denaturing Non-Reducing and Reducing Conditions

The results are shown in Table 58 below.

TABLE 58

| Species | DTT | LHHL | LHH | HH | LH | H | L |
|---|---|---|---|---|---|---|---|
| Optical | − | 71 | n.o.[1] | n.o.[1] | 29 | n.o.[1] | n.o.[1] |
| density (%) | + | 66 | n.o.[1] | n.o.[1] | 29 | n.o.[1] | 5 |

[1]not observed

Analysis on SDS-PAGE gel allowed determining under reducing conditions a reconstruction of 66% and under non-reducing conditions an average MAR of 2.00.

Example 46: Trastuzumab—Compound (39)—Compound (40) Conjugate

Reagents

Bioconjugation buffer 1, 5 mg/mL trastuzumab in bioconjugation buffer, reducing agent 1 (8.0 eq), compound (39) ($1^{st}$ compound) (12.0 eq) at a concentration of 3 mM in a mixture of 20% DMF and 80% MeOH, compound (40) ($2^{nd}$ compound) (13.2 eq) at a concentration of 10 mM in DMSO.

Method

Bioconjugation reaction 4

Denaturing HRMS Analysis According to Method 2

The results are shown in Table 59 below.

TABLE 59

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 (39)[3] | 2 | 148639 | n.o.[2] | |
| MAR 1 | 17 | 150086 | 100 | 76049 |
| MAR 2 | 81 | 152101 | n.o.[2] | |
| MAR 3 | n.o.[2] | | n.o.[2] | |
| Average MAR | 1.81 | | 1.00 | |

[1]molecular mass of the non-deglycosylated species

[2]not observed

[3]intermediate compound trastuzumab - compound (39) not clicked with compound (40)

HRMS analysis allowed determining an average MAR of 1.81 for the LHHL species and an average MAR of 1.00 for the LH species. LHH, HH, H and L species were not observed.

SDS-PAGE Gel Analysis Under Denaturing Non-Reducing and Reducing Conditions

The results are shown in Table 60 below.

TABLE 60

| Species | DTT | LHHL | LHH | HH | LH | H | L |
|---|---|---|---|---|---|---|---|
| Optical | − | 68 | n.o.[1] | n.o.[1] | 24 | n.o.[1] | 8 |
| density (%) | + | 63 | n.o.[1] | n.o.[1] | 28 | n.o.[1] | 9 |

[1]not observed

Analysis on SDS-PAGE gel allowed determining under reducing conditions a reconstruction of 63% and under non-reducing conditions an average MAR of 1.84.

Example 47: bicyclo[6.1.0]non-4-yn-9-ylmethyl (4-((2,6-bis(bromomethyl)isonicotinamido)methyl)-1-(2,6-bis(bromomethyl)pyridin-4-yl)-1,5-dioxo-9,12,15,18-tetraoxa-2,6-diazaicosan-20-yl)carbamate (41)

(41)

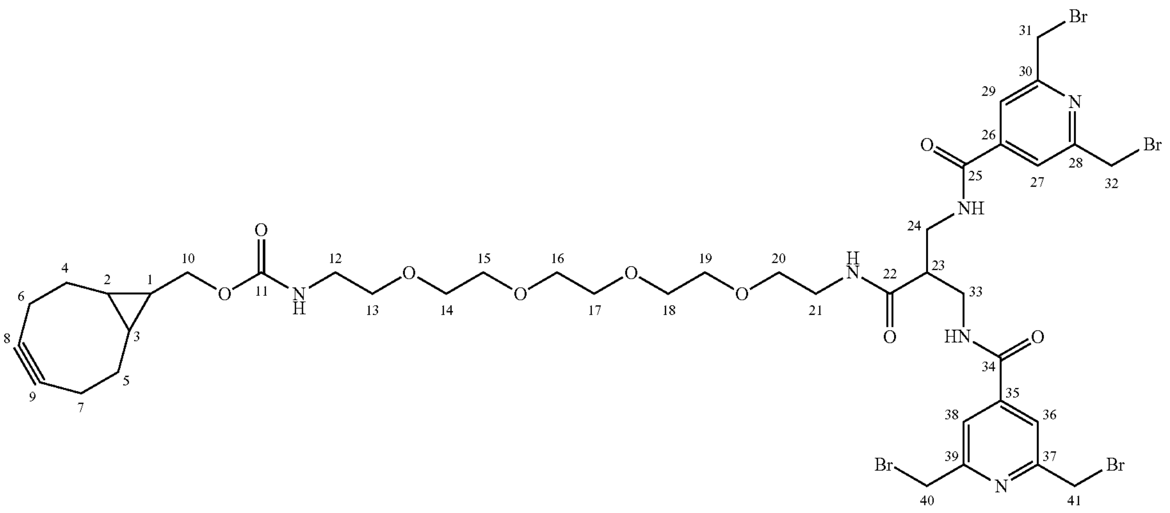

Under an inert atmosphere, in the dark and under anhydrous conditions, 3-(2,6-bis(bromomethyl)isonicotinamido)-2-((2,6-bis(bromomethyl)isonicotinamido)methyl)-propanoic acid (17) (8.3 mg; 0.012 mmol; 1.6 eq) was suspended in anhydrous MeCN (1.4 mL) then EEDQ (30.3 mg; 0.123 mmol; 17.0 eq) was added. The activation medium was stirred under argon at 25° C. for 30 min. A solution of bicyclo[6.1.0]non-4-yn-9-ylmethyl (14-amino-3,6,9,12-tetraoxatetradecyl)carbamate (3.8 mg; 0.007 mmol; 1.0 eq), dissolved in anhydrous DMF (1 mL) in the presence of anhydrous DIPEA (15.0 μL; 0.086 mmol; 11.9 eq), was added to the activation medium. The reaction medium obtained was stirred under argon at 25° C. for 1 hour. The mixture was purified by semi-preparative high-pressure liquid chromatography ($t_R$=22.64 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out in water (solvent A), and MeCN (solvent B); gradient 20 to 100% of B on 32 min then 100% B over 6 min at 17.1 mL/min) to give (41) (3.2 mg; 68%) in the form of a white lyophilisate.

$^1H$ NMR (300 MHz, $CD_3OD$) δ 7.87 (s; $4H_{27,29,36,38}$); 4.67 (s; $8H_{31,32,40,41}$); 4.13 (d; J=8.1 Hz; $1H_1$); 3.50-3.68 (m; $25H_{12,13,14,15,16,17,18,19,20,21,23,24,33}$); 2.02-2.25 (m; $8H_{4,5,6,7}$); 1.3-1.35 (m; $3H_{1,2,3}$).

HRMS (ESI): m/z calculated for $C_{41}H_{55}Br_4N_6O_9[M+H]^+$: 1091.0759; observed 1091.0758.

Example 48: Trastuzumab—Compound (41) Conjugate

Reagents

Bioconjugation buffer 1, 5 mg/mL trastuzumab in bioconjugation buffer, reducing agent 1 (7.0 eq), compound (41) (10.6 eq) at a concentration of 1 mM in a mixture of 80% DMF and 20% MeOH.

Method

Bioconjugation reaction 2.

Denaturing HRMS Analysis According to Method 2

The results are shown in Table 61 below.

TABLE 61

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | 95 | 148836 | 100 | 74806 |
| MAR 2 | 5 | 149616 | n.o.[2] | |
| MAR 3 | n.o.[2] | | n.o.[2] | |
| Average MAR | 1.05 | | 1.00 | |

[1]molecular mass of the non-deglycosylated species
[2]not observed

HRMS analysis allowed determining an average MAR of 1.05 for the LHHL species and 1.00 for the LH species. LHH, HH, H and L species were not observed.

SDS-PAGE Gel Analysis Under Denaturing Non-Reducing and Reducing Conditions

The results are shown in Table 62 below.

TABLE 62

| Species | DTT | LHHL | LHH | HH | LH | H | L |
|---|---|---|---|---|---|---|---|
| Optical | − | 88 | n.o.[1] | n.o.[1] | n.o.[1] | n.o.[1] | 12 |
| density (%) | + | 87 | n.o.[1] | n.o.[1] | 4 | n.o.[1] | 9 |

[1]not observed

Analysis on SDS-PAGE gel allowed determining under reducing conditions a reconstruction of 87% and under non-reducing conditions an average MAR of 1.05.

Example 49: Trastuzumab—Compound (41)—Compound (22) Conjugate

Reagents

Bioconjugation buffer 1, 5 mg/mL trastuzumab in bioconjugation buffer, reducing agent 1, compound (41) (1st compound) (10.6 eq) at a concentration of 1 mM in a mixture of 80% DMF and 20% MeOH, compound (22) ($2^{nd}$ compound) (11.7 eq) at a concentration of 10 mM in DMSO.

Method

Bioconjugation reaction 3.

Denaturing HRMS Analysis According to Method 2

The results are shown in Table 63 below.

TABLE 63

| | LHHL | | LH | |
|---|---|---|---|---|
| | Intensity (%) | MM (Da)[1] | Intensity (%) | MM (Da)[1] |
| MAR 0 | n.o.[2] | | 51 | 74032 |
| MAR 1 (41)[3] | 6 | 148841 | n.o.[2] | n.o.[2] |
| MAR 1 | 78 | 150099 | 49 | 76067 |
| MAR 2 | 16 | 152139 | n.o.[2] | |
| MAR 3 | n.o.[2] | | n.o.[2] | |
| Average MAR | 1.16 | | 0.49 | |

[1]molecular mass of the non-deglycosylated species
[2]not observed
[3]intermediate compound trastuzumab - compound (41) not clicked with compound (22)

HRMS analysis allowed determining an average MAR of 1.16 for the LHHL species and an average MAR of 0.49 for the LH species. LHH, HH, H and L species were not observed.

SDS-PAGE Gel Analysis Under Denaturing Non-Reducing and Reducing Conditions

The results are shown in Table 64 below.

TABLE 64

| Species | DTT | LHHL | LHH | HH | LH | H | L |
|---|---|---|---|---|---|---|---|
| Optical | − | 85 | n.o.[1] | n.o.[1] | 7 | 2 | 6 |
| density (%) | + | 70 | n.o.[1] | n.o.[1] | 8 | 12 | 10 |

[1]not observed

Analysis on SDS-PAGE gel allowed determining under reducing conditions a reconstruction of 70% and under non-reducing conditions an average MAR of 1.07.

Example 50: Trastuzumab—Compound (41)—Commercial Compound AF488 Conjugate

Reagents

Bioconjugation buffer 1, 5 mg/mL trastuzumab in bioconjugation buffer, reducing agent 1, compound (41) ($1^t$ compound) (10.6 eq) at a concentration of 1 mM in a mixture of 80% DMF and 20% MeOH, commercial compound (AF488) ($2^{nd}$ compound) (11.7 eq) at a concentration of 10 mM in DMSO.

(AF488)

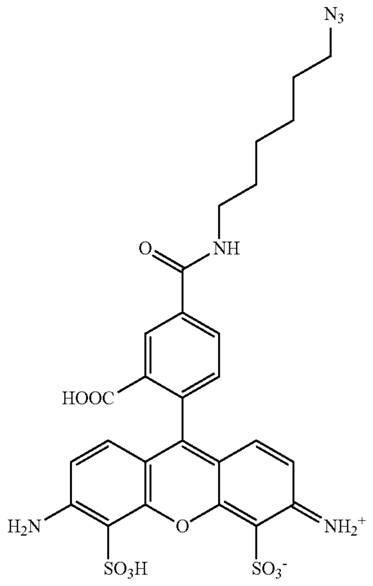

The results are shown in Table 66 below.

TABLE 66

| Species | DTT | LHHL | LHH | HH | LH | H | L |
|---|---|---|---|---|---|---|---|
| Optical | – | 85 | n.o.[1] | 3 | 9 | n.o.[1] | 3 |
| density (%) | + | 69 | n.o.[1] | 9 | 10 | 8 | 5 |

[1]not observed

Analysis on SDS-PAGE gel allowed determining under reducing conditions a reconstruction of 69% and under non-reducing conditions an average MAR of 1.30.

Example 51: Trastuzumab—Compound (41)—Commercial Compound $N_3$-Cap-Val-Cit-PAB-C6- Amanitine Conjugate Reagents Bioconjugation buffer 1, 5 mg/mL trastuzumab in bioconjugation buffer, reducing agent 1, compound (41) (1st compound) (10.6 eq) at a concentration of 1 mM in a mixture of 80% DMF and 20% MeOH, commercial compound ($N_3$—Cap-Val-Cit-PAB-C6- amanitine, obtained from the company Levena Biopharma) (2nd compound) (12.7 eq) at a concentration of 10 mM in DMSO.

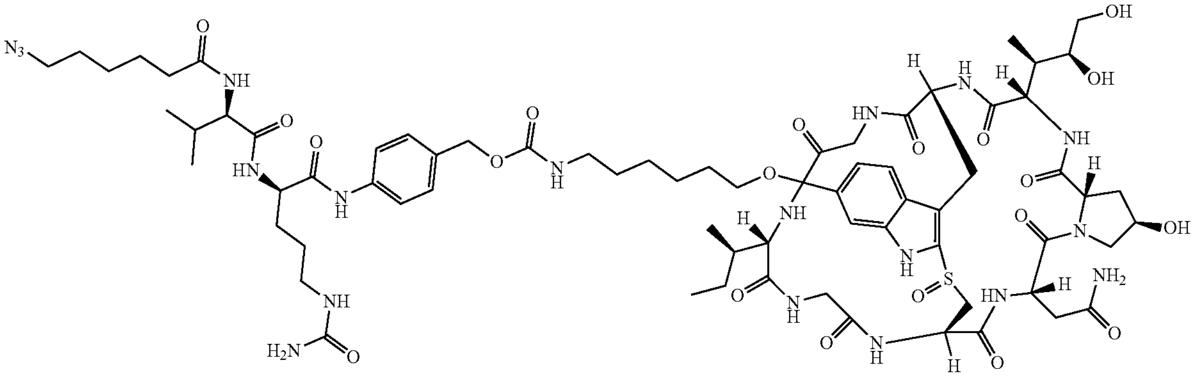 [SMILES: CC[C@@H](C)[C@@H]1NC2(OCCCCCCNC(=O)OCc3ccc(NC(=O)[C@@H](CCCNC(N)=O)NC(=O)[C@H](NC(=O)CCCCCN=[N+]=[N-])C(C)C)cc3)C(=O)CNC(=O)[C@H]3Cc4c([nH]c5cc2ccc45)S(=O)C[C@@H](NC(=O)CNC1=O)C(=O)N[C@@H](CC(N)=O)C(=O)N1C[C@H](O)C[C@H]1C(=O)N[C@@H]([C@@H](C)[C@H](O)CO)C(=O)N3]

($N_3$-Cap-Val-Cit-PAB-C6- amanitine)

Method

Bioconjugation reaction 3.

Denaturing HRMS Analysis According to Method 2

The results are shown in Table 67 below.

TABLE 67

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | n.o.[2] | | 5 | 74032 | 100 | 23439 |
| MAR 1 | 61 | 150395 | 95 | 76367 | n.o.[2] | |
| MAR 2 | 39 | 152747 | n.o.[2] | | n.o.[2] | |
| MAR 3 | n.o.[2] | | n.o.[2] | | n.o.[2] | |
| Average MAR | 1.39 | | 0.95 | | 0 | |

[1]molecular mass of the non-deglycosylated species
[2]not observed

HRMS analysis allowed determining an average MAR of 1.39 for the LHHL species and an average MAR of 0.95 for the LH species. LHH, HH and H species were not observed.

Method

Bioconjugation reaction 3.

Denaturing HRMS Analysis According to Method 2

The results are shown in Table 65 below.

TABLE 65

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | n.o.[2] | | 14 | 74032 | 100 | 23438 |
| MAR 1 | 74 | 149494 | 86 | 75463 | n.o.[2] | |
| MAR 2 | 26 | 150928 | n.o.[2] | | n.o.[2] | |
| MAR 3 | n.o.[2] | | n.o.[2] | | n.o.[2] | |
| Average MAR | 1.26 | | 0.86 | | 0 | |

[1]molecular mass of the non-deglycosylated species
[2]not observed

HRMS analysis allowed determining an average MAR of 1.26 for the LHHL species and an average MAR of 0.86 for the LH species. LHH, HH and H species were not observed.

SDS-PAGE Gel Analysis in Denaturing Non-Reducing and Reducing Conditions

SDS-PAGE Gel Analysis Under Denaturing Non-Reducing and Reducing Conditions

The results are shown in Table 68 below.

TABLE 68

| Species | DTT | LHHL | LHH | HH | LH | H | L |
|---|---|---|---|---|---|---|---|
| Optical | – | 86 | n.o.[1] | [2]n.o.[1] | 9 | 3 | 2 |
| density (%) | + | 72 | n.o.[1] | 4 | 14 | 8 | 2 |

[1]not observed

Analysis on SDS-PAGE gel allowed determining under reducing conditions a reconstruction of 72% and under non-reducing conditions an average MAR of 1.44.

Example 52: Trastuzumab—Compound (41) Conjugate

Reagents

Bioconjugation buffer 1, 5 mg/mL trastuzumab in bioconjugation buffer, reducing agent 1 (8.0 eq), compound (41) (12.0 eq) at a concentration of 3 mM in a mixture of 20% DMF and 80% MeOH.

Method

Bioconjugation reaction 1.

Denaturing HRMS Analysis According to Method 2

The results are shown in Table 69 below.

TABLE 69

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 100 | 74804 |
| MAR 2 | 100 | 149612 | n.o.[2] | |
| MAR 3 | n.o.[2] | | n.o.[2] | |
| Average MAR | 2.00 | | 1.00 | |

[1]molecular mass of the non-deglycosylated species
[2]not observed

HRMS analysis allowed determining an average MAR of 2.00 for LHHL species and 1.00 for LH species. LHH, HH, H and L species were not observed.

SDS-PAGE Gel Analysis Under Denaturing Non-Reducing and Reducing Conditions

The results are shown in Table 70 below.

TABLE 70

| Species | DTT | LHHL | LHH | HH | LH | H | L |
|---|---|---|---|---|---|---|---|
| Optical | – | 70 | n.o.[1] | n.o.[1] | 28 | n.o.[1] | 2 |
| density (%) | + | 62 | n.o.[1] | n.o.[1] | 32 | n.o.[1] | 6 |

[1]not observed

Analysis on SDS-PAGE gel allowed determining under reducing conditions a reconstruction of 62% and under non-reducing conditions an average MAR of 2.00.

Example 53: Trastuzumab—Compound (41)—Compound (22) Conjugate

Reagents

Bioconjugation buffer 1, 5 mg/mL trastuzumab in bioconjugation buffer, reducing agent 1 (8.0 eq), compound (41) ($1^{st}$ compound) (12.0 eq) at a concentration of 3 mM in a mixture of 20% DMF and 80% MeOH, compound (22) ($2^{nd}$ compound) (13.2 eq) at a concentration of 10 mM in DMSO.

Method

Bioconjugation reaction 4.

Denaturing HRMS analysis according to method 2

The results are shown in Table 71 below.

TABLE 71

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 100 | 76068 |
| MAR 2 | 100 | 152138 | n.o.[2] | |
| MAR 3 | n.o.[2] | | n.o.[2] | |
| Average MAR | 2.00 | | 1.00 | |

[1]molecular mass of the non-deglycosylated species
[2]not observed

HRMS analysis allowed determining an average MAR of 2.00 for LHHL species and an average MAR of 1.00 for LH species. LHH, HH, H and L species were not observed.

SDS-PAGE Gel Analysis Under Denaturing Non-Reducing and Reducing Conditions

The results are shown in Table 72 below.

TABLE 72

| Species | DTT | LHHL | LHH | HH | LH | H | L |
|---|---|---|---|---|---|---|---|
| Optical | – | 73 | n.o.[1] | n.o.[1] | 22 | n.o.[1] | 5 |
| density (%) | + | 56 | n.o.[1] | n.o.[1] | 37 | n.o.[1] | 7 |

[1]not observed

Analysis on SDS-PAGE gel allowed determining under reducing conditions a reconstruction of 56% and under non-reducing conditions an average MAR of 2.00.

Example 54: Trastuzumab—Compound (41)—Commercial Compound AF488 Conjugate

Reagents

Bioconjugation buffer 1, 5 mg/mL trastuzumab in bioconjugation buffer, reducing agent 1 (8.0 eq), compound (41) ($1^{st}$ compound) (12.0 eq) at a concentration of 3 mM in a mixture of 20% DMF and 80% MeOH, compound (AF488) ($2^{nd}$ compound) (13.2 eq) at a concentration of 10 mM in DMSO.

(AF488)

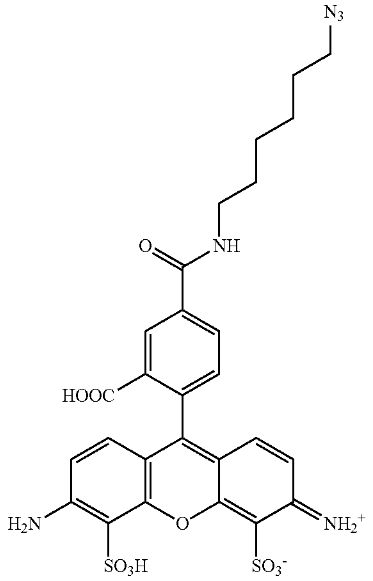

The results are shown in Table 74 below.

TABLE 74

| Species | DTT | LHHL | LHH | HH | LH | H | L |
|---|---|---|---|---|---|---|---|
| Optical | – | 64 | n.o.[1] | n.o.[1] | 29 | 3 | 4 |
| density | + | 55 | n.o.[1] | n.o.[1] | 42 | 2 | 1 |
| (%) | | | | | | | |

[1]not observed

Analysis on SDS-PAGE gel allowed determining under reducing conditions a reconstruction of 55% and under non-reducing conditions an average MAR of 2.00.

Example 55: Trastuzumab—Compound (41)—Commercial Compound $N_3$-Cap-Val-Cit-PAB-C6- Amanitine Conjugate Reagents Bioconjugation buffer 1, 5 mg/mL trastuzumab in bioconjugation buffer, reducing agent 1 (8.0 eq), compound (41) (1st compound) (12.0 eq) at a concentration of 3 mM in a mixture of 20% DMF and 80% MeOH, commercial compound ($N_3$—Cap-Val-Cit-PAB-C6-amanitine) (2nd compound) (13.2 eq) at a concentration of 10 mM in DMSO.

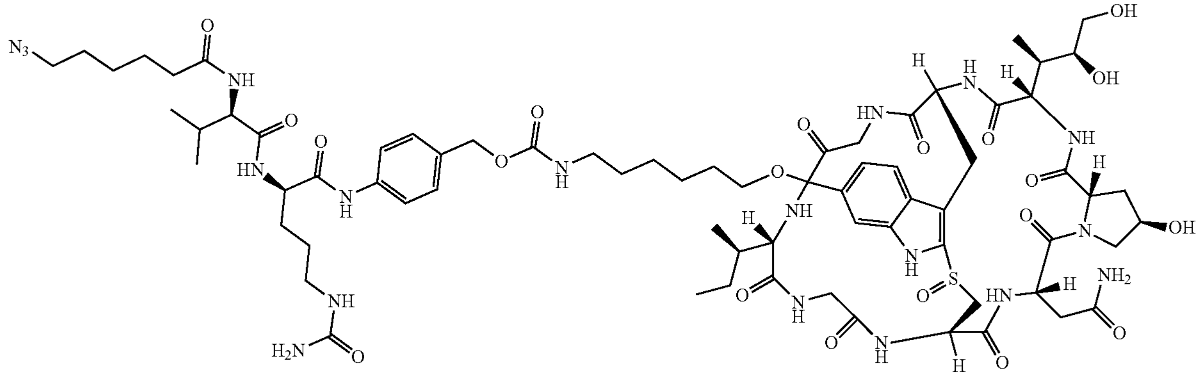 [SMILES: CC[C@@H](C)[C@@H]1NC2(OCCCCCCNC(=O)OCc3ccc(NC(=O)[C@@H](CCCNC(N)=O)NC(=O)[C@H](NC(=O)CCCCCN=[N+]=[N-])C(C)C)cc3)C(=O)CNC(=O)[C@H]3Cc4c([nH]c5cc2ccc45)S(=O)C[C@@H](NC(=O)CNC1=O)C(=O)N[C@@H](CC(N)=O)C(=O)N1C[C@H](O)C[C@H]1C(=O)N[C@@H]([C@@H](C)[C@H](O)CO)C(=O)N3]

Method

Bioconjugation reaction 4.

Denaturing HRMS Analysis According to Method 2

The results are shown in Table 73 below.

TABLE 73

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | n.o.[2] | | n.o.[2] | | 100 | 23438 |
| MAR 1 | n.o.[2] | | 100 | 75463 | n.o.[2] | |
| MAR 2 | 100 | 150928 | n.o.[2] | | n.o.[2] | |
| MAR 3 | n.o.[2] | | n.o.[2] | | n.o.[2] | |
| Average MAR | 2.00 | | 1.00 | | 0 | |

[1]molecular mass of the non-deglycosylated species
[2]not observed

HRMS analysis allowed determining an average MAR of 2.00 for LHHL species and an average MAR of 1.00 for LH species. LHH, HH and H species were not observed.

SDS-PAGE Gel Analysis Under Denaturing Non-Reducing and Reducing Conditions ($N_3$-Cap-Val-Cit-PAB-C6- amanitine)

Method

Bioconjugation reaction 4.

Denaturing HRMS Analysis According to Method 2

The results are shown in Table 75 below.

TABLE 75

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 100 | 76367 |
| MAR 2 | 100 | 152735 | n.o.[2] | |
| MAR 3 | n.o.[2] | | n.o.[2] | |
| Average MAR | 2.00 | | 1.00 | |

[1]molecular mass of the non-deglycosylated species
[2]not observed

HRMS analysis allowed determining an average MAR of 2.00 for LHHL species and an average MAR of 1.00 for LH species. LHH, HH, H and L species were not observed.

SDS-PAGE Gel Analysis Under Denaturing Non-Reducing and Reducing Conditions

The results are shown in Table 76 below.

TABLE 76

| Species | DTT | LHHL | LHH | HH | LH | H | L |
|---|---|---|---|---|---|---|---|
| Optical density (%) | – | 55 | n.o.[1] | 1 | 39 | 4 | 1 |
| | + | 52 | n.o.[1] | 2 | 38 | 7 | 1 |

[1]not observed

Analysis on SDS-PAGE gel allowed determining under reducing conditions a reconstruction of 52% and under non-reducing conditions an average MAR of 2.00.

Example 56: MMAE 2-amino-3-sulfopropanamido-valine-citrulline-p-aminobenzoyl carbamate, TFA Salt (42)

medium was stirred, under argon at RT for 15 h 40. Piperidine (80 μL, 20% v/v) was added and the reaction medium was stirred under argon at RT for 2 h. The mixture was purified by semi-preparative high-pressure liquid chromatography ($t_R$=13.07 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% B over 32 min then 100% B over 6 min at 17.1 mL/min) to give (42) (4.7 mg; 42%) in the form of a white lyophilisate.

(42)

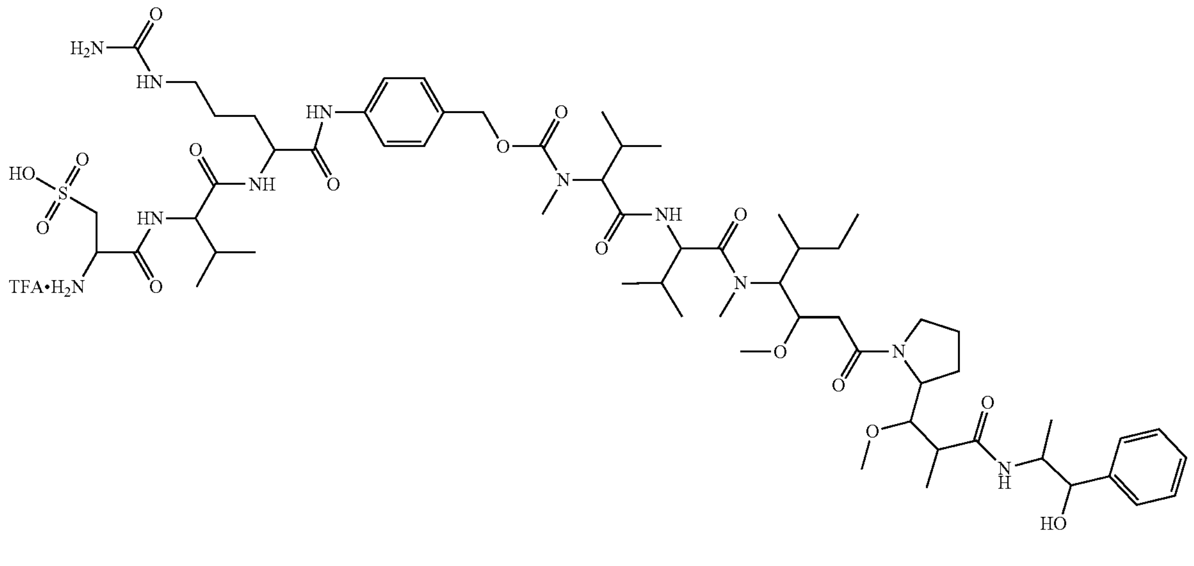

2-({[(9H-fluoren-9-yl)methoxy]carbonyl}amino)-3-sulfopropanoic acid (4.9 mg; 0.013 mmol; 1.6 eq) was dissolved in anhydrous DMF (200 μL). The reaction medium was cooled to 0° C., then HATU (15.2 mg; 0.040 mmol; 5.0 eq) and 2,6-lutidine (5.6 μL; 0.049 mmol; 6.0 eq) were added. The activation solution was stirred under argon at 0° C. for 5 min. A solution of MMAE valine-citrulline-p-aminobenzoyl carbamate trifluoroacetic acid salt (10.0 mg; 0.008 mmol; 1.0 eq), solubilized in anhydrous DMF (200 μL), was added to the activation medium. The reaction $^1$H NMR (300 MHz, DMSO) δ (ppm) 9.86 (s; 1H); 8.76 (d; J=8.2 Hz; 1H); 8.24 (d; J=7.6 Hz; 1H); 8.18-8.06 (m; 3H); 7.90 (d; J=8.9 Hz; 1H); 7.72-7.54 (m; 3H); 7.35-7.21 (m; 7H); 7.22-7.11 (m; 1H); 6.03-5.87 (m; 1H); 5.54-5.35 (m; 1H); 5.14-4.93 (m; 2H); 4.46 (dd; J=16.1; 6.1 Hz; 1H); 4.39-4.14 (m; 3H); 4.11-3.91 (m; 2H); 3.24 (d; J=4.8 Hz; 7H); 3.19 (d; J=7.8 Hz; 5H); 3.12 (s; 2H); 3.10-2.92 (m; 6H); 2.91-2.82 (m; 4H); 2.46-2.42 (m; 6H); 2.16-2.03 (m; 2H); 1.09-0.94 (m; 8H); 0.95-0.68 (m; 30H).

HRMS (ESI): m/z calculated for $C_{61}H_{100}N_{11}O_{16}S$ $[M+H]^+$: 1274.7065; observed 1274.7064.

Example 57: MMAE 3-(2,6-bis(bromomethyl)isonicotinamido)-2-((2,6bis(bromomethyl)isonicotinamido)methyl)propanamido)-3-sulfopropanamido-valine-citrulline-p-aminobenzoyl carbamate (43)

(43)

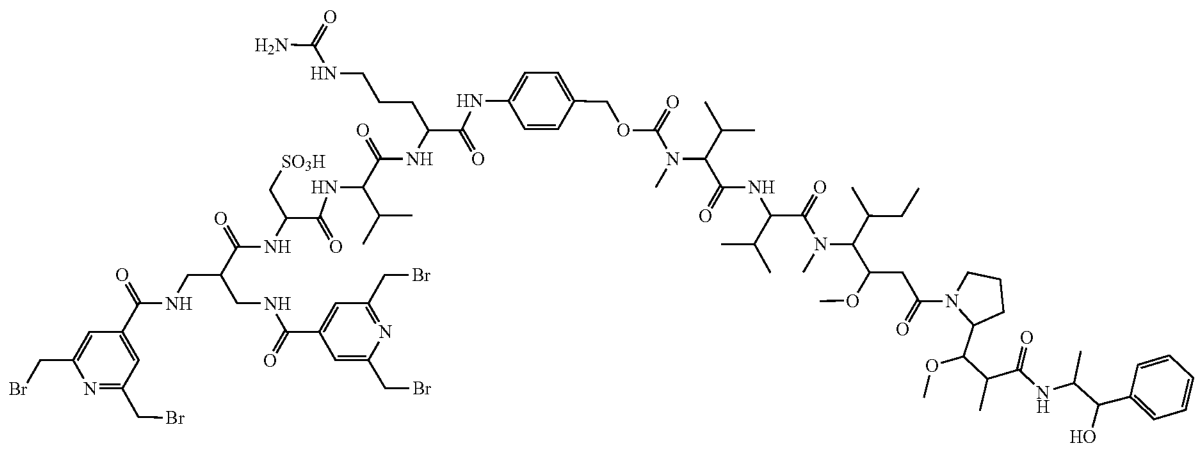

Under an inert atmosphere, in the dark and under anhydrous conditions, 3-(2,6-bis(bromomethyl)isonicotinamido)-2-((2,6-bis(bromomethyl)isonicotinamido)methyl)-propanoic acid (17) (4.5 mg; 0.0064 mmol; 1.9 eq) was suspended in anhydrous MeCN (371 μL) then EEDQ (12.6 mg; 0.051 mmol; 15.0 eq) was added. The activation medium was stirred under argon at 25° C. for 40 min. A solution of (42) (4.7 mg; 0.0034 mmol; 1.0 eq), dissolved in anhydrous DMF (68 μL) in the presence of anhydrous DIPEA (5.9 μL; 0.034 mmol; 10.0 eq), was added to the activation medium. The reaction medium obtained was stirred under argon at 25° C. for 3 h. The mixture was purified by semi-preparative high-pressure liquid chromatography ($t_R$=31.11 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 30 to 80% B over 49 min then 100% B over 5 min at 17.1 mL/min) to give (43) (4.1 mg; 62%) in the form of a white lyophilisate.

$^1$H NMR (300 MHz, $CD_3OD$) δ 7.88-7.84 (m; 2H); 7.81 (d; J=1.5 Hz; 2H); 7.57 (d; J=8.0 Hz; 2H); 7.41-7.35 (m; 2H); 7.35-7.25 (m; 2H); 7.25-7.12 (m; 3H); 5.14-4.94 (m; 5H); 4.65 (s; 8H); 4.62-4.49 (m; 5H); 4.32 (t; J=7.4 Hz; 1H); 4.28-4.11 (m; 4H); 4.11-3.80 (m; 1H); 3.79-3.59 (m; 5H); 3.45-3.37 (m; 4H); 3.34 (d; J=1.2 Hz; 8H); 3.26 (s; 2H); 3.25-3.16 (m; 2H); 3.12-3.01 (m; 2H); 3.00-2.84 (m; 3H); 2.58-2.40 (m; 2H); 2.34-2.09 (m; 2H); 2.07-1.74 (m; 3H); 1.74-1.51 (m; 1H); 1.49-1.23 (m; 10H); 1.22-1.07 (m; 7H); 1.07-0.71 (m; 30H).

HRMS (ESI): m/z calculated for $C_{81}H_{18}Br_4N_{15}O_{19}S[M+H]^+$: 1952.5177; observed 1952.5090.

Example 58: Trastuzumab—Compound (43) Conjugate

Reagents

Bioconjugation buffer 1, 5 mg/mL trastuzumab in bioconjugation buffer, reducing agent 1 (7.0 eq), compound (43) (10.6 eq) at a concentration of 1 mM in a mixture of 80% DMF and 20% MeOH.

Method

Bioconjugation reaction 2.

Denaturing HRMS Analysis According to Method 2

The results are shown in Table 77 below.

TABLE 77

| | LHHL | | LH | |
|---|---|---|---|---|
| | Intensity (%) | MM (Da)[1] | Intensity (%) | MM (Da)[1] |
| MAR 0 | n.o.[2] | | 39% | 74029 |
| MAR 1 | 100% | 149703 | 61% | 75664 |
| MAR 2 | n.o.[2] | | n.o.[2] | |
| MAR 3 | n.o.[2] | | n.o.[2] | |
| Average MAR | 1.00 | | 0.61 | |

[1]molecular mass of the non-deglycosylated species

[2]not observed

HRMS analysis allowed determining an average MAR of 1.00 for the LHHL species and of 0.61 for the LH species. LHH, HH, H and L species were not observed.

SDS-PAGE Gel Analysis Under Denaturing Non-Reducing and Reducing Conditions

The results are shown in Table 78 below.

TABLE 78

| Species | DTT | LHHL | LHH | HH | LH | H | L |
|---|---|---|---|---|---|---|---|
| Optical density (%) | − | 85 | n.o.[1] | n.o.[1] | 7 | n.o.[1] | 8 |
| | + | 60 | n.o.[1] | n.o.[1] | 15 | 15 | 10 |

[1]not observed

Analysis on SDS-PAGE gel allowed determining under reducing conditions a reconstruction of 60% and under non-reducing conditions an average MAR of 1.02.

Example 59: Trastuzumab—Compound (43) Conjugate

Reagents

Bioconjugation buffer 1, 5 mg/mL trastuzumab in bioconjugation buffer, reducing agent 1 (7.0 eq), compound (43) (12.0 eq) at a concentration of 3 mM in a mixture of 20% DMF and 80% MeOH.

Method

Bioconjugation reaction 2.

Denaturing HRMS Analysis According to Method 2

The results are shown in Table 79 below.

TABLE 79

| | LHHL | | LH | |
|---|---|---|---|---|
| | Intensity (%) | MM (Da)[1] | Intensity (%) | MM (Da)[1] |
| MAR 0 | n.o.[2] | | n.o.[2] | |
| MAR 1 | n.o.[2] | | 100 | 75666 |
| MAR 2 | 100% | 151332 | n.o.[2] | |
| MAR 3 | n.o.[2] | | n.o.[2] | |
| MAR medium | 2.00 | | 1.00 | |

[1]molecular mass of the non-deglycosylated species
[2]not observed

HRMS analysis allowed determining an average MAR of 2.00 for LHHL species and 1.00 for LH species. LHH, HH, H and L species were not observed.

SDS-PAGE Gel Analysis Under Denaturing Non-Reducing and Reducing Conditions

The results are shown in Table 80 below.

TABLE 80

| Species | DTT | LHHL | LHH | HH | LH | H | L |
|---|---|---|---|---|---|---|---|
| Optical density (%) | − | 56 | n.o.[1] | n.o.[1] | 34 | n.o.[1] | 10 |
| | + | 54 | n.o.[1] | n.o.[1] | 37 | n.o.[1] | 9 |

[1]not observed

Analysis on SDS-PAGE gel allowed determining under reducing conditions a reconstruction of 54% and under non-reducing conditions an average MAR of 2.00.

Example 60: MMAE amine 3-[2-(2-aminoethoxy) ethoxy]-propanamido-valine-citrulline-p-aminobenzoyl carbamate, TFA salt (44)

(44)

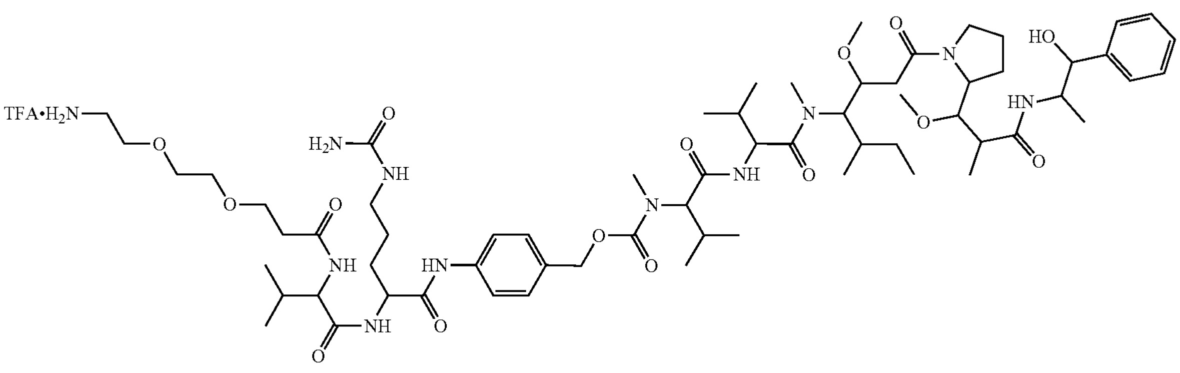

1-(9H-fluoren-9-yl)-3-oxo-2,7,10-trioxa-4-azatridecan-13-oic acid (4.0 mg; 0.010 mmol; 1.2 eq) was dissolved in anhydrous DMF (200 μL). The reaction medium was cooled to 0° C., then HATU (12.5 mg; 0.033 mmol; 4.0 eq) and 2,6-lutidine (5.6 μL; 0.049 mmol; 5.8 eq) were added. The activation solution was stirred under argon at 0° C. for 15 min. A solution of MMAE valine-citrulline-p-aminobenzoyl carbamate trifluoroacetic acid salt (10.3 mg; 0.008 mmol; 1.0 eq), solubilized in anhydrous DMF (200 μL), was added to the activation medium. The reaction medium was placed under stirring, under argon at RT for 16 h. Piperidine (80 μL, 20% v/v) was added and the reaction medium was stirred under argon at RT for 10 min. The mixture was purified by semi-preparative high-pressure liquid chromatography ($t_R$=18.24 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% B over 32 min then 100% B over 6 min at 17.1 mL/min) to give (44) (4.8 mg; 45%) in the form of a white lyophilisate.

$^1$H NMR (300 MHz, $CD_3OD$) δ 8.29 (m; 1H); 7.99-8.05 (m; 2H); 7.61 (m; 2H); 7.28-7.41 (m; 7H); 5.36 (m; 1H); 4.53 (m; 1H); 4.22 (m; 4H); 3.78 (m; 2H); 3.65 (m; 3H); 2.94 (m; 4H); 2.47-2.59 (m, 5H); 2.21 (m; 3H); 1.59-2.18 (m; 11H); 1.41-1.59 (m; 4H); 1.34 (s; 17); 1.02 (m; 7H); 0.80-1.01 (m; 34H).

HRMS (ESI): m/z calculated for $C_{65}H_{109}N_{11}O_{15}$ $[M+2H]^{2+}$: 641.9047; observed 641.9046.

Example 61: MMAE 3-(2,6-bis(bromomethyl)isonicotinamido)-2-((2,6bis(bromomethyl)isonicotinamido)methyl)propanamido)-3-(2-(2-aminoethoxy) ethoxy)propanamido-valine-citrulline-p-aminobenzoyl carbamate (45)

(45)

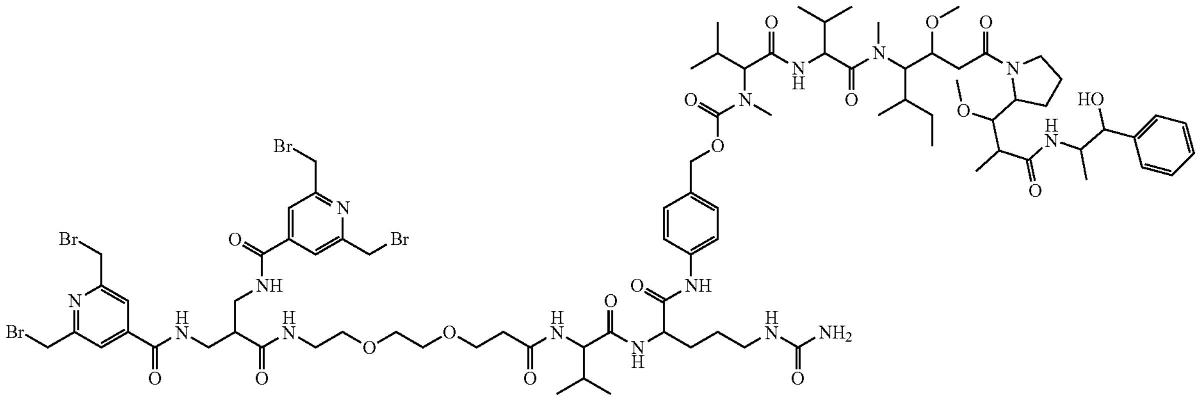

Under an inert atmosphere, in the dark and under anhydrous conditions, 3-(2,6-bis(bromomethyl)isonicotinamido)-2-((2,6-bis(bromomethyl)isonicotinamido)methyl)-propanoic acid (17) (2.8 mg; 0.004 mmol; 2.2 eq) was suspended in anhydrous MeCN (421 μL) then EEDQ (7.7 mg; 0.031 mmol; 17.5 eq) was added. The activation medium was stirred under argon at 25° C. for 30 min. A solution of (44) (2.5 mg; 0.002 mmol; 1.0 eq), dissolved in anhydrous DMF (360 μL) in the presence of anhydrous DIPEA (3.1 μL; 0.018 mmol; 10.0 eq), was added to the activation medium. The reaction medium obtained was stirred under argon at 25° C. for 1 h. The mixture was purified by semi-preparative high-pressure liquid chromatography ($t_R$=32.59 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with 0.1% TFA (by volume) in water (solvent A), and MeCN (solvent B); gradient 20 to 100% B over 32 min then 100% B over 6 min at 17.1 mL/min) to give (45) (2.3 mg; 65%) in the form of a white lyophilisate.

$^1$H NMR (300 MHz, $CD_3OD$) δ 9.83 (s; 1H); 8.90 (m; 2H); 8.33 (m; 1H); 7.78-7.84 (m; 8H); 7.69-7.84 (m; 3H); 7.41-7.68 (m; 6H); 7.20-7.31 (m; 1H); 5.02-5.27 (m; 4H); 4.53 (s; 2H); 4.26 (m; 5H); 3.89 (m; 1H); 3.62-3.86 (m; 10H); 3.10 (m; 5H); 2.93 (m; 4H); 2.51 (m; 4H); 2.24-2.47 (m; 3H); 2.07 (s; 3H); 1.94-2.05 (m; 7H); 1.60 (m; 5H); 1.31 (m; 11H); 1.08-1.25 (m; 8H); 0.71-1.06 (m; 32H).

HRMS (ESI): m/z calculated for $C_{90}H_{127}Br_4N_{13}O_{16}$ $[M+2H]^{2+}$: 980.8123; observed 980.8108.

Example 62: 3-amino-N,N'-bis(2-(2-[2-(2-azidoethoxy)-ethoxy]ethoxy}ethyl)pentanediamide (46)

(46)

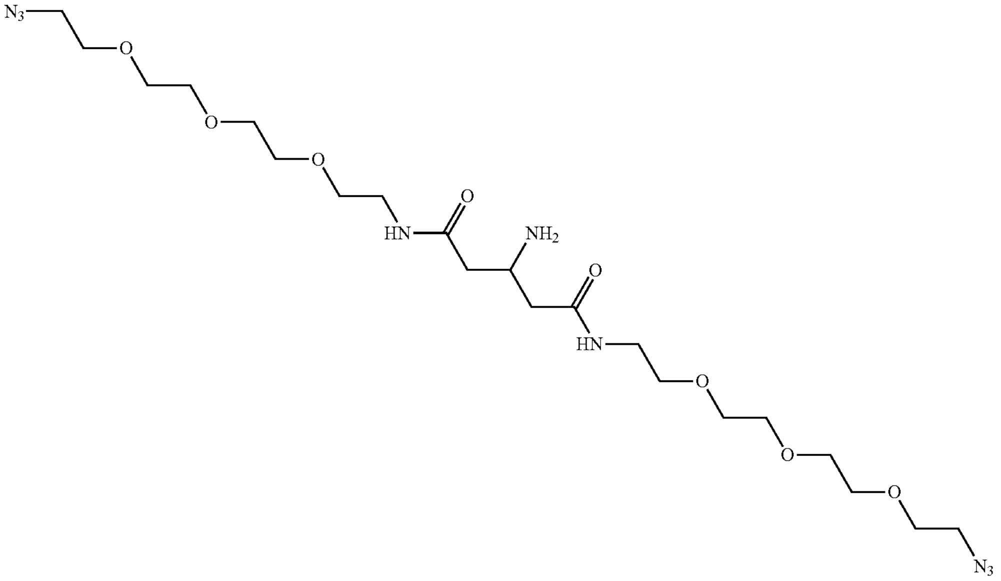

3-({[(9H-fluoren-9-yl)methoxy]carbonyl}amino)pentanedioic acid (10.0 mg; 0.027 mmol; 1.0 eq) was dissolved in peptide DMF (200 μL). The reaction medium was cooled to 0° C., then a solution of HATU (30.9 mg; 0.081 mmol; 3.0 eq) and 2,6-lutidine (18.8 μL; 0.162 mmol; 6.0 eq), solubilized in peptide DMF (150 μL), was added. The activation solution was stirred under argon at 0° C. for 10 min. A solution of 2-(2-(2-(2-azidoethoxy)ethoxy)ethoxy)ethan-1-amine (15.4 mg; 0.070 mmol; 2.6 eq), dissolved in anhydrous DMF (100 μL), was added to the activation medium. The reaction medium was stirred, under argon at RT for 3 h 40. Piperidine (90 μL, 20% v/v) was added and the reaction medium was stirred under argon at RT for 16 h. The mixture was evaporated to dryness then the residue was taken up in peptide DMF (3 mL) and directly purified by semi-preparative high-pressure liquid chromatography ($t_R$=25.47 min; on the Gilson PLC 2050 system [ARMEN V2 (pump), ECOM TOYDAD600 (UV detector), SEDEX FP SAGA (DEDL detector)] UV detection at 254 nm at 25° C. and DEDL at 60° C.; Waters XBridge™ C-18 column; 5 μm (250 mm×19.00 mm); elution carried out with water (solvent A), and MeCN (solvent B); gradient 5 to 10% of B over 20 min then 100% of B over 5 min at 17.1 mL/min) to give (46) (6.2 mg; 42%) in the form of a colorless oil.

$^1$H NMR (300 MHz, DMSO) δ 8.01 (t; J=5.5 Hz; 2H); 3.65-3.56 (m; 5H); 3.56-3.47 (m; 19H); 3.24-3.16 (m; 8H); 2.94-2.87 (m; 1H); 2.23-2.00 (m; 4H).

HRMS (ESI): m/z calculated for $C_{21}H_{42}N_9O_8$ $[M+H]^+$: 548.3151; observed 548.3147.

Example 63: $N^1$-$N^5$-bis(2-(2-(2-(2-azidoethoxy)ethoxy)ethoxy)ethyl)-3-(3-(2,6-bis(bromomethyl)isonicotinamido)-2-((2,6-bis(bromomethyl)isonicotinamido)methyl)propanamido)pentanediamide (47)

(47)

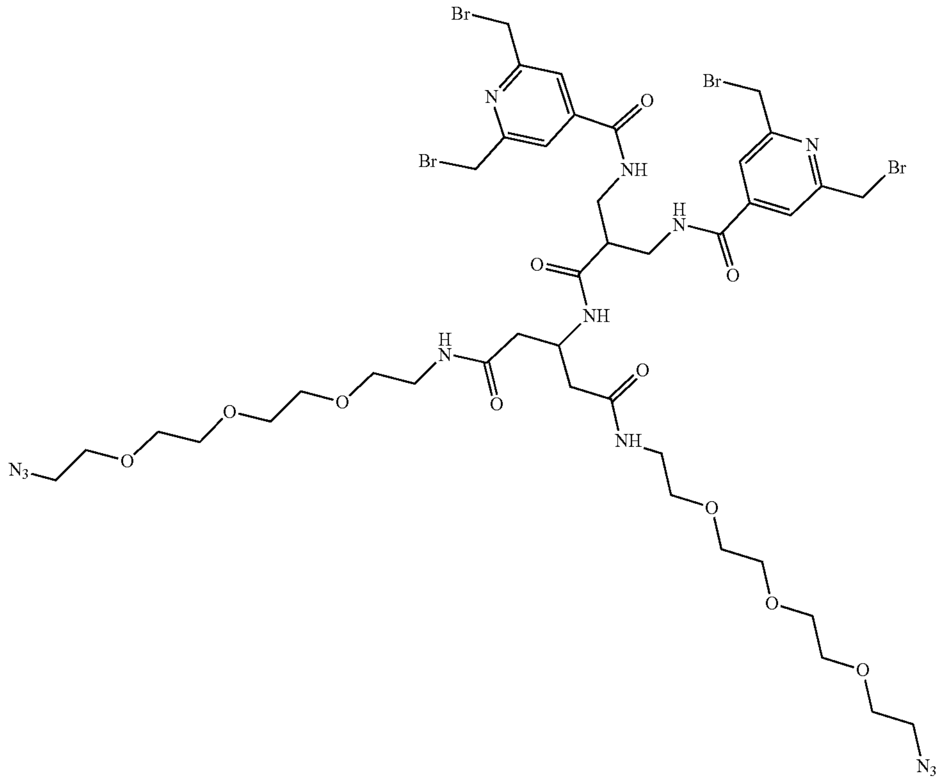

-

Under an inert atmosphere, in the dark and under anhydrous conditions, 3-(2,6-bis(bromomethyl)isonicotinamido)-2-((2,6-bis(bromomethyl)isonicotinamido)methyl)-propanoic acid (17) (16.3 mg; 0.023 mmol; 1.6 eq) was suspended in anhydrous MeCN (400 μL) then EEDQ (6.2 mg; 0.025 mmol; 1.7 eq) was added. The activation medium was stirred under argon at 25° C. for 45 min. A solution of (46) (8.0 mg; 0.0146 mmol; 1.0 eq), dissolved in anhydrous DMF (100 μL) in the presence of anhydrous DIPEA (11.8 μL; 0.068 mmol; 4.7 eq), was added to the activation medium. The reaction medium obtained was stirred under argon at 25° C. for 1 h. The mixture was purified by semi-preparative high-pressure liquid chromatography ($t_R$=18.38 min; on the Gilson PLC 2050 system [ARMEN V2 (pump) and ECOM TOYDAD600 (UV detector)] UV detection at 254 nm at 25° C.; Waters XBridge™ C-18 column; 5 μm (250 mm×19.00 mm); elution carried out with water (solvent A), and MeCN (solvent B); gradient 20 to 78% of B on 22 min then 78% B over 8 min, then 78 to 100% B over 3 min, then 100% B over 4 min at 17.1 mL/min) to give (47) (2.3 mg; 13%) in the form of a colorless film.

$^1$H NMR (300 MHz, $CD_3OD$) δ 7.88 (s; 4H); 4.65 (s; 8H); 4.59 (m; 4H); 3.74-3.53 (m; 30H); 3.49 (t; J=5.4 Hz; 4H); 3.39-3.34 (m; 4H); 2.91 (m; 1H); 2.54-2.33 (m; 4H).

HRMS (ESI): m/z calculated for $C_{41}H_{60}Br_4N_{13}O_{11}$ $[M+H]^+$: 1226.1263; observed 1226,1262.

Example 64: Trastuzumab—Compound (47) Conjugate

Reagents

Bioconjugation buffer 1, 5 mg/mL trastuzumab in bioconjugation buffer, reducing agent 2 (8.0 eq), compound (47) (12.0 eq) at a concentration of 3 mM in a mixture of 20% DMF and 80% MeOH.

Method

Bioconjugation reaction 1.

Denaturing HRMS Analysis According to Method 2

The results are shown in Table 81 below.

TABLE 81

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | n.o.[2] | | n.o.[2] | | 100 | 23439 |
| MAR 1 | 13 | 148979 | 100 | 74940 | n.o.[2] | |
| MAR 2 | 87 | 149882 | n.o.[2] | | n.o.[2] | |
| MAR 3 | n.o.[2] | | n.o.[2] | | n.o.[2] | |
| Average MAR | 1.87 | | 1.00 | | 0 | |

[1]molecular mass of the non-deglycosylated species
[2]not observed

HRMS analysis allowed determining an average MAR of 1.87 for the LHHL species and 1.00 for the LH species. LHH, HH, and H species were not observed.

SDS-PAGE Gel Analysis Under Denaturing Non-Reducing and Reducing Conditions

The results are shown in Table 82 below.

TABLE 82

| Species | DTT | LHHL | LHH | HH | LH | H | L |
|---|---|---|---|---|---|---|---|
| Optical density (%) | − | 60 | n.o.[1] | n.o.[1] | 40 | n.o.[1] | n.o.[1] |
| | + | 55 | n.o.[1] | 3 | 35 | 6 | 1 |

[1]not observed

Analysis on SDS-PAGE gel allowed determining under reducing conditions a reconstruction of 55% and under non-reducing conditions an average MAR of 1.92.

Example 65: Trastuzumab—Compound (47)—Compound (40) Conjugate

Reagents

Bioconjugation buffer 1, 5 mg/mL trastuzumab in bioconjugation buffer, reducing agent 2 (8.0 eq), compound (47) ($1^{st}$ compound) (12.0 eq) at a concentration of 3 mM in a mixture of 20% DMF and 80% MeOH, compound (40) ($2^{nd}$ compound) (30.0 eq) at a concentration of 1 mM in DMSO.

Method

Bioconjugation reaction 4. In this case, the reaction mixture was purified on PD-10 (GE Healthcare) with PBS buffer Gibco© pH 7.4, the concentration of the intermediate trastuzumab-compound (47) conjugate was adjusted to 1.4 mg/mL before adding the compound (40) and the reaction medium was stirred for 22 h.

Denaturing HRMS Analysis According to Method 2

The results are shown in Table 83 below.

TABLE 83

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | n.o.[2] | | n.o.[2] | | 100 | 23405 |
| MAR 1 | 14 | 151858 | 90 | 77817 | n.o.[2] | |
| N.D.[3] | 8 | 154529 | 10 | 76712 | n.o.[2] | |
| MAR 2 | 78 | 155640 | n.o.[2] | | n.o.[2] | |
| MAR 3 | n.o.[2] | | n.o.[2] | | n.o.[2] | |
| Average MAR | 1.70 | | 0.90 | | 0 | |

[1]molecular mass of the non-deglycosylated species
[2]not observed
[3]ND: impurity of undetermined structure HRMS analysis allowed determining an average MAR of 1.70 for the LHHL species and an average MAR of 0.90 for the LH species. LHH, HH, and H species were not observed.

SDS-PAGE Gel Analysis Under Denaturing Non-Reducing and Reducing Conditions

The results are shown in Table 84 below.

TABLE 84

| Species | DTT | LHHL | LHH | HH | LH | H | L |
|---|---|---|---|---|---|---|---|
| Optical density (%) | − | 61 | n.o.[1] | n.o.[1] | 39 | n.o.[1] | n.o.[1] |
| | + | 56 | n.o.[1] | 3 | 36 | 5 | n.o.[1] |

[1]not observed

Analysis on SDS-PAGE gel allowed determining under reducing conditions a reconstruction of 56% and under non-reducing conditions an average MAR of 1.74.

Example 66: Trastuzumab—Compound (47) Conjugate

Reagents

Bioconjugation buffer 1, 5 mg/mL trastuzumab in bioconjugation buffer, reducing agent 1 (7.0 eq), compound (47) (10.6 eq) at a concentration of 1 mM in a mixture of 80% DMF and 20% MeOH.

Method

Bioconjugation reaction 2.

Denaturing HRMS Analysis According to Method 2

The results are shown in Table 85 below.

TABLE 85

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | n.o.[2] | | 15 | 74034 | 45 | 23439 |
| MAR 1 | 87 | 148973 | 85 | 74939 | 55 | 24345 |

TABLE 85-continued

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 2 | 13 | 149885 | n.o.[2] | | n.o.[2] | |
| MAR 3 | n.o.[2] | | n.o.[2] | | n.o.[2] | |
| Average MAR | 1.13 | | 0.85 | | 0.55 | |

[1]molecular mass of the non-deglycosylated species
[2]not observed

HRMS analysis allowed determining an average MAR of 1.13 for the LHHL species and of 0.85 for the LH species. HH and H species were not observed.

SDS-PAGE Gel Analysis Under Denaturing Non-Reducing and Reducing Conditions

The results are shown in Table 86 below.

TABLE 86

| Species | DTT | LHHL | LHH | HH | LH | H | L |
|---|---|---|---|---|---|---|---|
| Optical density (%) | – | 94 | n.o.[1] | n.o.[1] | 6 | n.o.[1] | n.o.[1] |
| | + | 63 | n.o.[1] | 6 | 15 | 13 | 3 |

[1]not observed

Analysis on SDS-PAGE gel allowed determining under reducing conditions a reconstruction of 63% and under non-reducing conditions an average MAR of 1.16.

Example 67: Trastuzumab—Compound (47)—Compound (40) Conjugate

Reagents

Bioconjugation buffer 1, 5 mg/mL trastuzumab in bioconjugation buffer, reducing agent 1, compound (47) ($1^{st}$ compound) (10.6 eq) at a concentration of 1 mM in a mixture of 80% DMF and 20% MeOH, compound (40) ($2^{nd}$ compound) (15.0 eq) at a concentration of 1 mM in DMSO.

Method

Bioconjugation reaction 3. In this case, the reaction mixture was purified on PD-10 (GE Healthcare) with PBS buffer Gibco© pH 7.4, the concentration of the intermediate trastuzumab-compound (47) conjugate is adjusted to 1.5 mg/mL before adding the compound (40) and the reaction medium was stirred for 22 h.

Denaturing HRMS Analysis According to Method 2

The results are shown in Table 87 below.

TABLE 87

| | LHHL | | LH | | L | |
|---|---|---|---|---|---|---|
| | Intensity (%) | MM (Da)[1] | Intensity (%) | MM (Da)[1] | Intensity (%) | MM (Da) |
| MAR 0 | 2 | 148057 | 15 | 74026 | 80 | 23405 |
| N.D.[3] | 10 | 150747 | 5 | 76712 | n.o.[2] | |
| MAR 1 | 73 | 151852 | 80 | 77817 | 20 | 27223 |
| MAR 2 | 15 | 155650 | n.o.[2] | | n.o.[2] | |
| MAR 3 | n.o.[2] | | n.o.[2] | | n.o.[2] | |
| Average MAR | 1.02 | | 0.80 | | 0.20 | |

[1]molecular mass of the non-deglycosylated species
[2]not observed
[3]ND: impurity of undetermined structure HRMS analysis allowed determining an average MAR of 1.02 for the LHHL species and an average MAR of 0.80 for the LH species. LHH, HH, and H species were not observed.

SDS-PAGE Gel Analysis Under Denaturing Non-Reducing and Reducing Conditions

The results are shown in Table 88 below.

TABLE 88

| Species | DTT | LHHL | LHH | HH | LH | H | L |
|---|---|---|---|---|---|---|---|
| Optical density (%) | – | 91 | n.o.[1] | n.o.[1] | 9 | n.o.[1] | n.o.[1] |
| | + | 63 | n.o.[1] | 6 | 15 | 12 | 4 |

[1]not observed

Analysis on SDS-PAGE gel allowed determining under reducing conditions a reconstruction of 63% and under non-reducing conditions an average MAR of 1.07.

The invention claimed is:

1. A compound of formula (II):

(II)

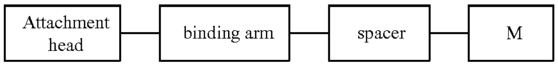

, wherein:

the attachment head is a compound of formula (I), formula (Ia), or formula (Ib):

(I)

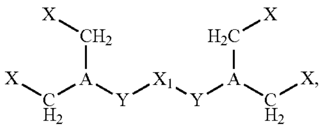

(Ia)

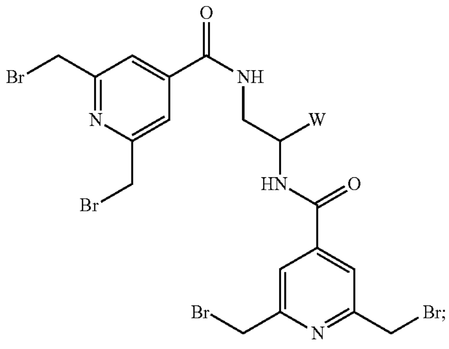

-continued (Ib)

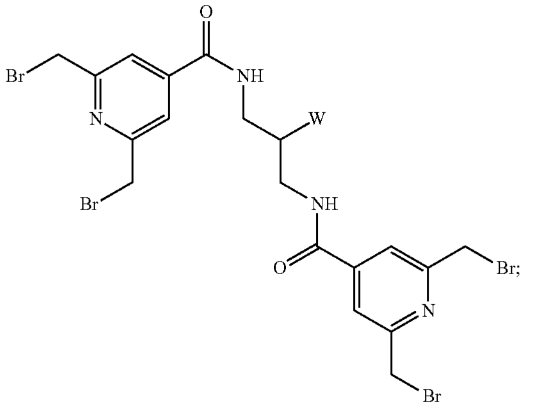

wherein:

each A is the residue of a pyridyl;

each X is a halogen;

each Y is selected from a direct bond, —CO—, and —NH—;

$X_1$ is

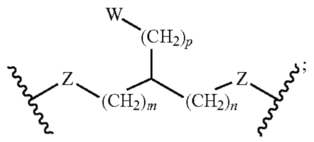

W is $-CONR_3R_4$ or $-NR_3COR_4$;

each Z is independently a direct bond, $-CH_2-$, —O—, —S—, —CO—, —NH—, or $-C(=NR_1)-$;

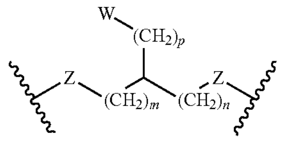

and m, n and p are each, independently of one another, an integer in the range from 0 to 8;

$R_3$ is —H or $-(C_1\text{-}C_6)$alkyl or $-(CH_2)_u-SO_3H$;

$R_4$ is $-(CH_2CH_2O)_qR_5$, $-(CR_cR_d)_rR_5$, $-(CR_cR_d)_r-NHCO-(CH_2CH_2O)_q-R_5$, $-(CR_cR_d)_r-CONH-(CH_2CH_2O)_q-R_5$, $-(CH_2CH_2O)_q-(CH_2)_r-NHCO-(CR_cR_d)_r-R_5$, $-(CH_2CH_2O)_q-(CH_2)_r-CONH-(CR_cR_d)_r-R_5$, $-CH-[(CR_cR_d)_r-CONH-(CR_cR_d)_r-(OCH_2CH_2)_q-R_5]_2$, $-CH-[(CR_cR_d)_r-NHCO-(CR_cR_d)_r-(OCH_2CH_2)_q-R_5]_2$, $-CH-[(CR_cR_d)_r-CONH-(CR_cR_d)_rR_5]_2$, or $-CH-[(CR_cR_d)_r-NHCO-(CR_cR_d)_r-R_5]_2$;

$R_5$ is $-(CH_2)_sR_6$ or $-(CH_2)_sR_7$;

$R_6$ is $-COOR_8$, $-COSR_8$, $-CONR_8R_9$, or $-NR_8COR_9$;

$R_7$ is selected from:

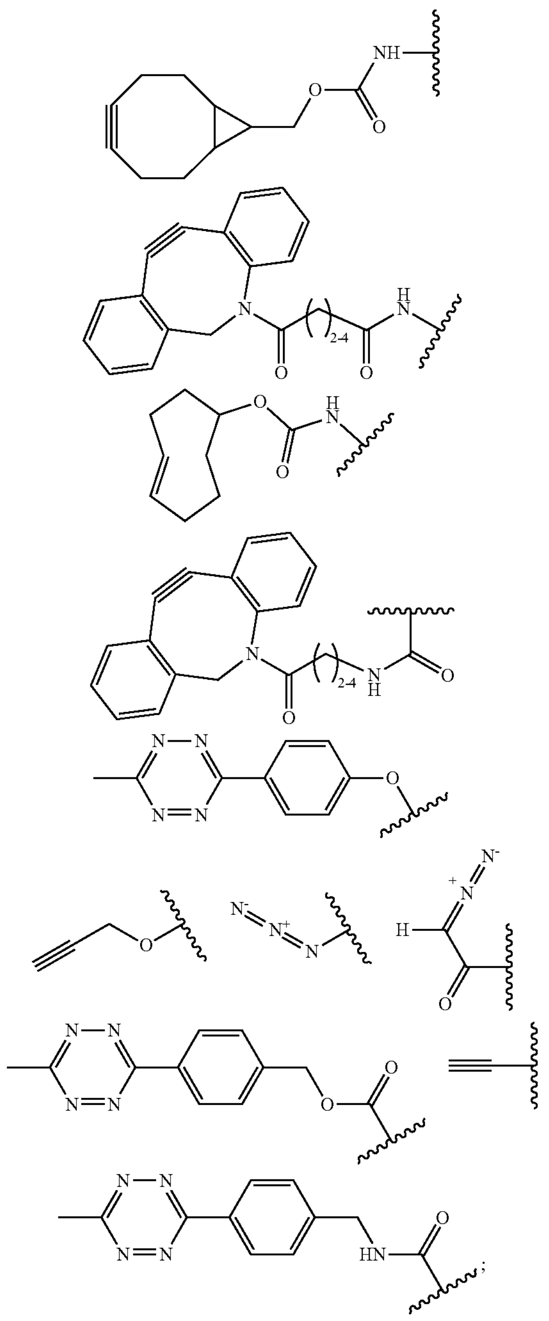

$R_c$ is —H;

each $R_d$ is —H, $-SO_3H$, or $-CH_2-SO_3H$;

$R_8$ is —H or $-(C_1\text{-}C_6)$alkyl;

$R_9$ is —H or $-(C_1\text{-}C_6)$alkyl;

each q is an integer in the range from 1 to 24;

each r is an integer in the range from 1 to 8;

each s is an integer in the range from 0 to 6;

each u is an integer in the range from 1 to 6;

the binding arm is a direct bond; an amino acid residue; or a peptide residue;

the spacer is a direct bond or a group of formula:

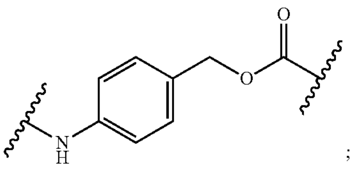 [SMILES: *Nc1ccc(COC(*)=O)cc1]

;

M is a molecule of interest.

2. The compound according to claim 1, wherein a part of formula (II) consisting of the binding arm and the spacer is represented by one of the formulas (III) or (IV):

(III)

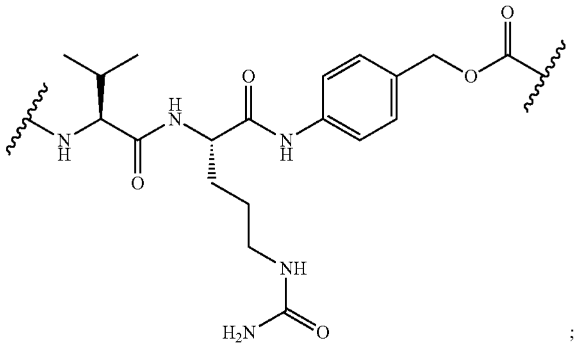

;

(IV)

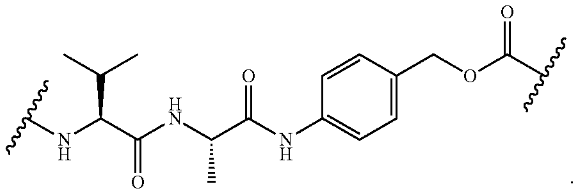

.

3. The compound according to claim 1, wherein the molecule of interest is an active ingredient, a fluorophore, or a cage for radioelements.

4. The compound according to claim 1, wherein the active ingredient is selected from the group consisting of: methotrexate, an immunomodulator, duocarmycin, combretastatin, calicheamicin, monomethylauristatin E (MMAE), monomethylauristatin F (MMAF), maytansin, DM1, DM4, SN38, amanitine and its analogs, pyrrolobenzodiazepine, a pyrrolobenzodiazepine dimer, pyrrolopyridodiazepine, a pyrrolopyridodiazepine dimer, a histone deacetylase inhibitor, a tyrosine kinase inhibitor, and ricin.

5. A conjugate obtained:

(c2) by conjugation between a protein comprising at least two disulfide bridges and a compound of formula (II):

(II)

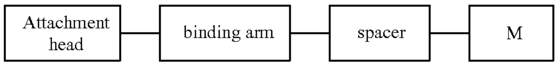

wherein:

the attachment head is a compound of formula (I), formula (Ia), or formula (Ib) as defined in claim 1, the binding arm is a direct bond; an amino acid residue; or a peptide residue;

the spacer is a direct bond or a group of formula:

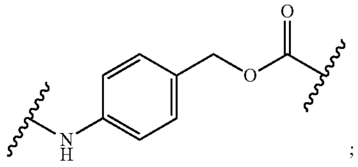 [SMILES: *Nc1ccc(COC(*)=O)cc1]

;

M is a molecule of interest, or (c3) by reaction between:

(i) a protein comprising at least two disulfide bridges, (ii) the compound of formula (I), formula (Ia), or formula (Ib), and (iii) a compound of formula (V):

(V)

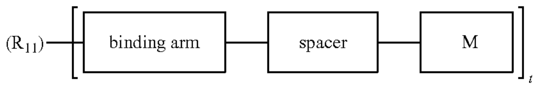

wherein:

$R_{11}$ is $R_7$—$(CH_2)_s$—CO—, $R_7$—$(CH_2)_s$—CONHCH[$CH_2$CO-]2, $R_7$—$(CH_2)_s$—(O—$CH_2$—$CH_2)_q$—CO—, or $R_7$—$(CH_2)_s$—(O—$CH_2$—$CH_2)_q$—CONHCH[$CH_2$CO-$]_2$, $R_7$ is as defined in the compound of formula (I), wherein at least one of $R_7$ and $R_{11}$ comprises a diene moiety, and at least one of $R_7$ and $R_{11}$ comprises a dienophile moiety;

$R_c$, $R_d$, $R_5$, s, and r are as defined for the compound of formula (I);

each q is an integer ranging from 1 to 12;

each s is an integer ranging from 0 to 6;

t is 1 or 2;

the binding arm, the spacer, and M are as defined in the compound of formula (II).

6. The conjugate according to claim 5, wherein the protein comprising at least two disulfide bridges is an antibody or an antibody fragment.

7. The conjugate according to claim 6, having the following structure:

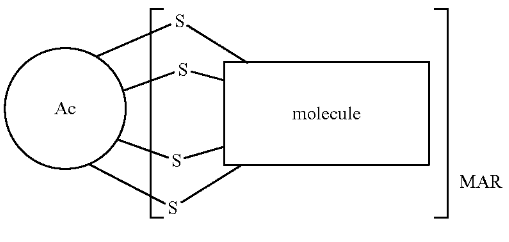

wherein:

Ac is an antibody or antibody fragment;

the molecule is the product of the reaction between:

(i) the compound of formula (I), formula (Ia), or formula (Ib), and (ii) the compound of formula (V); and MAR, which represents the average number of molecule (s) bound to the antibody or the antibody fragment, is comprised in the range from 0.50 to 2.50.

8. The conjugate according to claim 7, wherein MAR=1.00±0.50.

9. The conjugate according to claim 7, wherein MAR=2.00±0.50.

10. A composition comprising one or more conjugate(s) according to claim 5.

11. The conjugate according to claim 5, wherein the molecule of interest is an active ingredient, a fluorophore or a cage for radioelements.

12. The conjugate according to claim 5, wherein the molecule of interest is an active ingredient selected from the group consisting of: methotrexate, an immunomodulator, duocarmycin, combretastatin, calicheamicin, monomethylauristatin E, monomethylauristatin F, maytansin, DM1, DM4, SN38, amanitine and its analogs, pyrrolobenzodiazepine, a pyrrolobenzodiazepine dimer, pyrrolopyridodiazepine, a pyrrolopyridodiazepine dimer, a histone deacetylase inhibitor, a tyrosine kinase inhibitor, and ricin.

13. The conjugate according to claim 12, wherein the active ingredient is amanitine, monomethylauristatin E, pyrrolobenzodiazepine, or a pyrrolobenzodiazepine dimer.

* * * * *